United States Patent
Gilbert et al.

(10) Patent No.: US 11,254,933 B2
(45) Date of Patent: Feb. 22, 2022

(54) CRISPR/CAS TRANSCRIPTIONAL MODULATION

(71) Applicant: THE REGENTS OF THE UNIVERSITY OF CALIFORNIA, Oakland, CA (US)

(72) Inventors: Luke A Gilbert, San Francisco, CA (US); Max Horlbeck, Oakland, CA (US); Martin Kampmann, Oakland, CA (US); Lei S Qi, Oakland, CA (US); Jonathan S Weissman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/326,428

(22) PCT Filed: Jul. 14, 2015

(86) PCT No.: PCT/US2015/040449
§ 371 (c)(1),
(2) Date: Jan. 13, 2017

(87) PCT Pub. No.: WO2016/011080
PCT Pub. Date: Jan. 21, 2016

(65) Prior Publication Data
US 2017/0204407 A1    Jul. 20, 2017

Related U.S. Application Data

(60) Provisional application No. 62/024,373, filed on Jul. 14, 2014.

(51) Int. Cl.
*C12N 15/10* (2006.01)
*C12Q 1/6897* (2018.01)
*C12N 15/63* (2006.01)

(52) U.S. Cl.
CPC ....... *C12N 15/1079* (2013.01); *C12N 15/102* (2013.01); *C12N 15/1082* (2013.01); *C12N 15/63* (2013.01); *C12Q 1/6897* (2013.01)

(58) Field of Classification Search
CPC .................... C12N 15/1079; C12N 2310/20
See application file for complete search history.

(56) References Cited

U.S. PATENT DOCUMENTS

| | | | | |
|---|---|---|---|---|
| 8,697,359 B1* | 4/2014 | Zhang | .................... | C12N 15/85 435/6.1 |
| 2014/0068797 A1* | 3/2014 | Doudna | .............. | C12N 15/102 800/18 |
| 2015/0376586 A1* | 12/2015 | May | ..................... | C12N 15/111 424/93.7 |
| 2016/0289673 A1 | 10/2016 | Huang et al. | | |

FOREIGN PATENT DOCUMENTS

| | | |
|---|---|---|
| WO | 2014/005042 A2 | 1/2014 |
| WO | 2014/093655 A2 | 6/2014 |
| WO | 2014/093701 A1 | 6/2014 |
| WO | 2014/099744 A1 | 6/2014 |

OTHER PUBLICATIONS

Shalem et al. (2014) Genome-Scale CRISPR-Cas9 Knockout Screening in Human Cells. Science, 343:84-8, and supplementary materials.*
Kouzarides, T. (2007) Chromatin Modifications and Their Function. Cell, 128:693-705 (Year: 2007).*
Bendich et al. (2000) Prokaryotic and eukaryotic chromosomes: what's the difference? BioEssays, 22:481-486 (Year: 2000).*
DNA Polymerase II, MeSH Descriptor Data 2018, revised Jul. 8, 2013, obtained at <https://meshb.nlm.nih.gov/record/ui?ui=D004257> on Apr. 13, 2018, 2 pages (Year: 2013).*
DNA Polymerase III, MeSH Descriptor Data 2018, revised Jul. 8, 2013, obtained at <https://meshb.nlm.nih.gov/record/ui?name=DNA%20Polymerase%20III (Year: 2013).*
Mueller-Planitz et al. (2013) Nucleosome sliding mechanisms: new twists in a looped history. Nature Structural & Molecular Biology, 20(9): 1026-1032 (Year: 2013).*
Whitehead et al. (2005) Variation in tissue-specific gene expression among natural populations. Genome Biology, 6(R13): pp. 1-14 (Year: 2005).*
Bassik et al. (2013) A Systematic Mammalian Genetic Interaction Map Reveals Pathways Underlying Ricin Susceptibility. Cell 152: 909-922 (Year: 2013).*
Nielsen et al. (2013) Mechanism of Eukaryotic RNA Polymerase III Transcription Termination. Science, 340:1577-1580, and supplementary materials (Year: 2013).*
Matveeva et al. (2010) Optimization of Duplex Stability and Terminal Asymmetry for shRNA Design. PLoS ONE, 5(4):e10180, pp. 1-9 (Year: 2010).*
Forrest et al. (2014) A promoter-level mammalian expression atlas. Nature, 507:462-471 (Year: 2014).*
Wu et al. (2014) Genome-wide binding of the CRISCRISCRISCRISPR endonuclease Cas9 in mammalian cells. Nature Biotechnology, 32(7):670-676 (Year: 2014).*
Mali et al. (2013) RNA-Guided Human Genome Engineering via Cas9. Science, 339:823-826 (Year: 2013).*
Radzisheuskaya et al. (2016) Optimizing sgRNA position markedly improves the efficiency of CRISPR/dCas9-mediated transcriptional repression. Nucleic Acids Research, 44(18):e141, pp. 1-13 (Year: 2016).*
Dreos et al. (2013) EPD and EPDnew, high-quality promoter resources in the next-generation sequencing era. Nucleic Acids Research, 41:D157-D164 (Year: 2013).*
Wu et al. (2013) Assessing the impact of human genome annotation choice on RNA-seq expression estimates. BMC Bioinformatics, 14(Suppl 11):S8, pp. 1-13 (Year: 2013).*

(Continued)

*Primary Examiner* — Neil P Hammell
(74) *Attorney, Agent, or Firm* — Kilpatrick Townsend & Stockton LLP

(57) ABSTRACT

Methods, compositions, and kits are provided for CRISPR/Cas mediated transcriptional modulation.

17 Claims, 47 Drawing Sheets

Specification includes a Sequence Listing.

(56) References Cited

OTHER PUBLICATIONS

Lei et al., Repurposing CRISPR as an RNA-Guided Platform for Sequence-Specific Control of Gene Expression, Cell, vol. 152, No. 5, Feb. 28, 2013.
Maeder et al., CRISPR RNA-guided activation of endogenous human genes, Nature Methods, vol. 10, No. 10, Jul. 25, 2013.
Mali et al., CAS9 transcriptional activators for target specificity screening and paired nickases for cooperation genome engineering, Nature Biotechnology, vol. 31, No. 9, Aug. 1, 2013.
Farzadfard et al., "Tunable and Multifunctional Eukaryotic Transcription Factors Based on CRISPR/Cas", ACS Synthetic Biology, vol. 2, No. 10, Oct. 18, 2013.
Larson et al., CRISPR interference (CRISPRi) for sequence-specific control of gene expression, Nature Protocols, vol. 8, No. 11, Nov. 1, 2013.
Koike-Yusa et al., "Genome-wide recessive genetic screening in mammalian cells with a lentiviral CRISPR-guide RNA library", Nature Biotechnology, vol. 32, No. 3, Dec. 23, 2013.
Nissim et al., "Multiplexed and Programmable Regulation of Gene Networks with an Integrated RNA and CRISPR/CAS Toolkit in Human Cells", Molecular Cell, vol. 54, No. 4, May 22, 2014.
Kabadi et al., "Engineering synthetic TALE and CRISPR/Cas9 transcription factors for regulating gene expression", Methods, vol. 69, No. 2, Jul. 8, 2014.
Gilbert et al. "Genome-Scale CRISPR-Mediated Control of Gene Repression and Activation", Cell, vol. 159, No. 3, Oct. 1, 2014.
Tanenbaum et al., "A Protein-Tagging System for Signal Amplification in Gene Expression and Fluorescence Imaging", Cell, vol. 159, No. 3, Oct. 9, 2014.
The Partial Supplementary European Search Report from Appln. No. 15822737.1 dated Feb. 20, 2018.
Qi et al., "Repurposing CRISPR as an RNA-Guided Platform for Sequence-Specific Control of Gene Expression," Cell, 152, Feb. 28, 2013, 1173-1183.
Horlbeck et al., "Compact and highly active next-generation libraries for CRISPR-mediated gene repression and activation," eLife, 5, (2016), e19760.
Chen et al., Dynamic Imaging of Genomic Loci in Living Human Cells by an Optimized CRISPR/Cas System, Cell, vol. 155:1479-1491 Dec. 19, 2013.
Horlbeck et al., Compact and Highly Active Next-Generation Libraries for CRISPR-mediated Gene Repression and Activation, eLife, vol. 5, e19760, Sep. 23, 2016.
Horlbeck et al.,Nucleosomes Impede Cas9 Access to DNA In Vivo and In Vitro, eLife; vol. 5, e12677, Mar. 17, 2016.
KONERMANN et al., Optical Control of Mammalian Endogenous Transcription and Epigenetic States, Nature, vol. 500, 472-489, Aug. 22, 2013.
Rogers et al., Context Influences on TALE-DNA Binding Revealed by Quantitative Profiling, Nature Communications, vol. 6:7440, 1-10, Jun. 11, 2015.
Boettcher, Michael, et al., "Choosing the Right Tool for the Job: RNAi, TALEN, or CRISPR," Molecular Cell Review, 58, Elsevier Inc., pp. 575-585, May 21, 2015.
Gilbert, L., et al., "CRISPR Screening From Both Ways," Nature Review Genetics, AOP, vol. 15, Dec. 2014, published online; doi 10.1038/nrg3850; Original Research Paper: Gilbert, L.A., et al., "Genome-Scale CRISPR Mediated Control of Gene Repression and Activation," Cell http://dx.doi.org/10.1016/j.cell.2014.09.029 (2014).
Radzisheuskaya, A., et al., "Optimizing sgRNA Position Markedly Improves the Efficiency of CRISPR/dCas9-mediated Transcriptional Repression," Nucleic Acids Research, 2016, vol. 44, No. 18, pp. 1-13, e141, http://dx.doi.org/10.1093/nar/gkw583.
Zhu, S., et al., "Making Better CRISPR Libraries," eLIFE, 2016; 5:e21863, pp. 1-3, http://dx.doi.org/10.7554/eLife.21863.
Dreos, R. et al., EPD and EPDnew, high-quality promoter resources in the next-generation sequencing era, Nucleic Acids Research, 2013, vol. 41, Database issue D157-D164, https://academic.oup.com/nar/article-abstract/41/D1/D57/1078274.

* cited by examiner

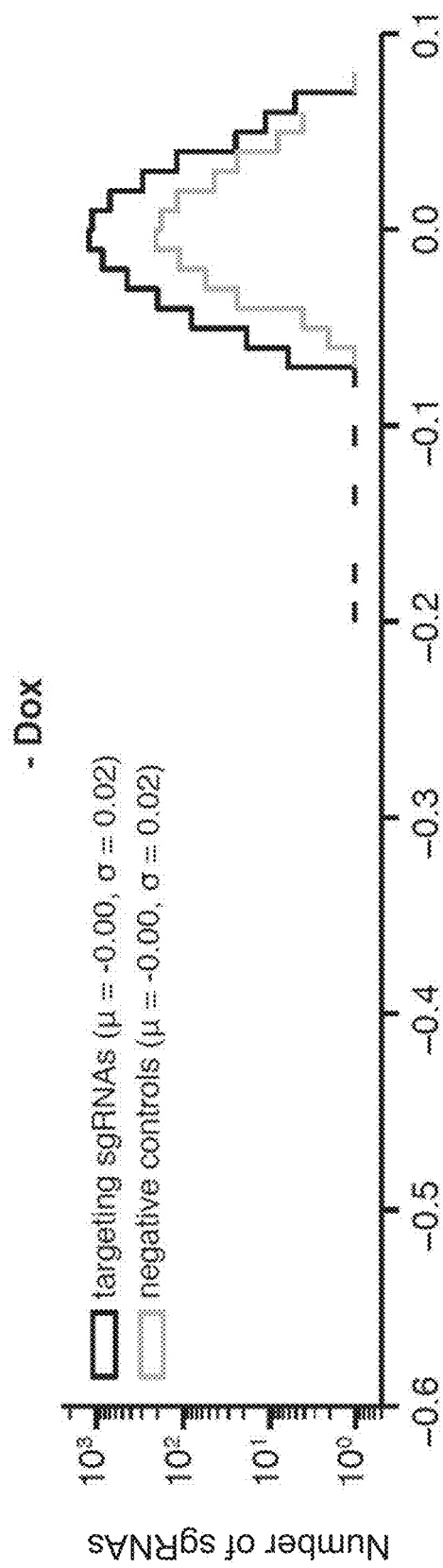
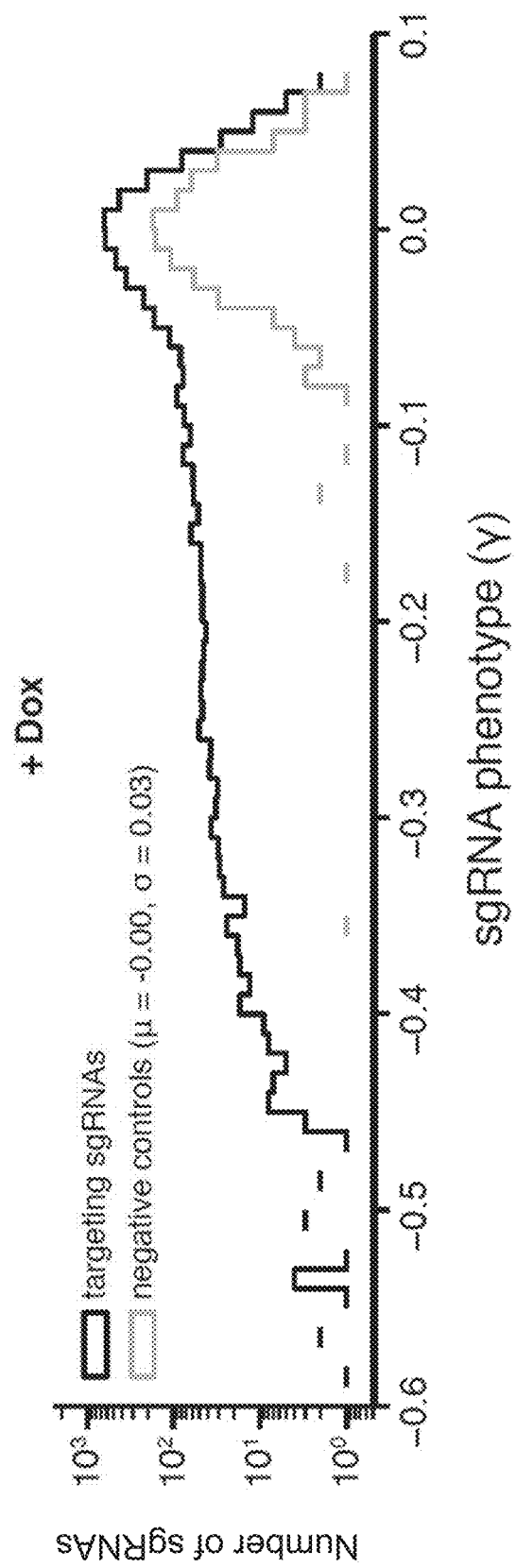
FIG. 5F
FIG. 5G

CRISPRi and CRISPRa sgRNA library construction (version 2)

Transcription Start Site Determination

Select genes to target

Extract Transcription Start Site (TSS) for each transcript from Ensembl annotaton (5' most position)
Group TSSs for gene within 200bp windows Define "primary" and "secondary" TSSs using the FANTOM5 Cap Analysis of Gene Expression (CAGE) Classifier
 -Search for "p1@gene" or "p2@gene" within 30kb of annotated TSS.
  where the gene name or synonym matches the gene of interest
  -In the above cases, assign "p1" to "primary" and "p2" to "secondary"
 -If not found, search instead for any "p1" and "p2" on the same strand within 500bp
  -In the above cases, assign "p1" to "primary" and "p2" to "secondary"
 -If not found, search for any "robust" TSS on the same strand within 200bp
 -If not found, search for any "permissive" TSS on the same strand within 200bp
  -In the above cases, assign most 5' TSS to "primary" and most 3' TSS to "secondary"
 -If no CAGE evidence found, assign annotated TSS to both "primary" and "secondary"

*FIG. 16A*

CRISPR/CAS TRANSCRIPTIONAL MODULATION

CROSS-REFERENCES TO RELATED APPLICATIONS

This application is a U.S. National Phase of PCT/US2015/040449, international filing date Jul. 14, 2015, which claims priority to U.S. Provisional Application No. 62/024,373, filed on Jul. 14, 2014, the contents of which are hereby incorporated by reference in the entirety for all purposes.

STATEMENT AS TO RIGHTS TO INVENTIONS MADE UNDER FEDERALLY SPONSORED RESEARCH AND DEVELOPMENT

This invention was made with government support under Grant Nos. OD017887, P50 GM102706 and RO1 DA036858 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

This application includes a Sequence Listing as a text file named "81906_948709_seq_listing" created Jul. 13, 2015 and containing 127,743,598 bytes, machine format IBM-PC, MS-Windows operating system. The material contained in this text file is incorporated by reference in its entirety for all purposes.

BACKGROUND OF THE INVENTION

Clustered, regularly interspaced short palindromic repeat (CRISPR) sequences are present in approximately 40% of eubacterial genomes and nearly all archaeal genomes sequenced to date, and consist of short (~24-48 nucleotide) direct repeats separated by similarly sized, unique spacers. They are generally flanked by a set of CRISPR-associated (Cas) genes that encode a nuclease that is important for CRISPR maintenance and function. In *Streptococcus thermophilus* and *Escherichia coli*, CRISPR/Cas loci have been demonstrated to confer immunity against bacteriophage infection by an interference mechanism that relies on the strict identity between CRISPR spacers and phage target sequences. The mechanism underlying this immunity is based on sequence specific cleavage of foreign nucleic acids by a CRISPR:Cas complex that contains a guide RNA that provides target sequence specificity through a single stranded binding region and is derived from the CRISPR sequences and a guide RNA dependent nuclease encoded by the Cas gene. Binding of the CRISPR:Cas complex to the target sequence results in double stranded cleavage of the target sequence.

The CRISPR/Cas system has been modified for use in prokaryotic and eukaryotic systems for genome editing and transcriptional regulation. However, methods and compositions known the in art often fail to provide the activity and specificity necessary for routine use. For example, Cradick, et al., Nucleic Acids Res. Aug. 11, 2013; Pattanayak, et al., Nat Biotechnol. 2013 September; 31(9):839-43; Mali, et al., Nat Biotechnol. 2013 September; 31(9):833-8; and Hsu, et al., Nat Biotechnol. 2013 September; 31(9):827-32, all report significant off-target genome editing and varied editing efficiency across different gene targets. Similar issues also exist when using known CRISPR/Cas systems for regulation of transcription.

BRIEF SUMMARY OF THE INVENTION

In some embodiments, the present invention provides a method of screening for one or more genetic elements that modulate a phenotype, the method comprising: contacting a plurality of cells with a library of structurally distinct small guide RNAs (sgRNAs) that target a plurality of genetic elements, thereby generating a plurality of test cells, the plurality of test cells each comprising: a small guide RNA (sgRNA); and a nuclease deficient sgRNA-mediated nuclease (dCas9), wherein the dCas9 comprises a dCas9 domain fused to a transcriptional modulator; or a dCas9 domain fused to an epitope fusion domain, selecting the test cells on the basis of the phenotype; and quantitating the frequency of the structurally distinct sgRNAs within the population of selected cells, wherein the sgRNAs that target genetic elements that modulate the phenotype are overrepresented or underrepresented in the selected cells.

In some cases, the dCas9 comprises a dCas9 domain and a transcriptional activator. In some cases, the dCas9 domain and transcriptional activator comprises the amino acid sequence of SEQ ID NO:1 or 2. In some cases, the library of sgRNAs are targeted to a region between 0-750 bp upstream of the transcription start site of the targeted genes. In some cases, the dCas9 comprises a dCas9 domain and a transcriptional repressor. In some cases, the library of sgRNAs are targeted to a region between 0-1000 bp downstream of the transcription start site of the targeted genes. In some cases, the dCas9 domain and transcriptional repressor comprises the amino acid sequence of SEQ ID NO:3. In some cases, wherein the dCas9 comprises: a first dCas9 fused to a transcriptional repressor; and a second dCas9 fused to a transcriptional activator; or a second dCas9 fused to an epitope fusion domain. In some cases, at least a portion of the plurality of test cells comprise a Cas9 nuclease.

In some cases, the library of sgRNAs contains or contains at least 1; 2; 3; 5; 10; 100; 1,000; 10,000; 100,000; 200,000; 400,000; or 1 million structurally distinct sgRNAs. In some cases the, or the at least, 1; 2; 3; 5; 10; 100; 1,000; 10,000; 100,000; or 200,000 structurally distinct sgRNAs comprise binding regions that are independently selected from the group consisting of the sgRNA binding region sequences encoded by SEQ ID NOs:26-205,305. In some cases the, or the at least, 1; 2; 3; 5; 10; 100; 1,000; 10,000; 100,000; or 200,000 structurally distinct sgRNAs comprise binding regions that comprise a sequence independently selected from the group consisting of the sgRNA binding region sequences encoded by the 19 nucleotides at the 3' end of SEQ ID NOs:26-205,305.

In some cases the, or the at least, 1; 2; 3; 5; 10; 100; 1,000; 10,000; 100,000; or 200,000 structurally distinct sgRNAs comprise binding regions that are independently selected from the group consisting of the sgRNA binding region sequences encoded by SEQ ID NOs:205,306-410,595. In some cases the, or the at least, 1; 2; 3; 5; 10; 100; 1,000; 10,000; 100,000; or 200,000 structurally distinct sgRNAs comprise binding regions that comprise a sequence independently selected from the group consisting of the sgRNA binding region sequences encoded by the 19 nucleotides at the 3' end of SEQ ID NOs:205,306-410,595.

In some cases the, or the at least, 1; 2; 3; 5; 10; 100; 1,000; 10,000; 100,000; or 200,000 structurally distinct sgRNAs comprise binding regions that are independently selected from the group consisting of the sgRNA binding region sequences encoded by SEQ ID NOs:410,596-633,445. In some cases the, or the at least, 1; 2; 3; 5; 10; 100; 1,000; 10,000; 100,000; or 200,000 structurally distinct sgRNAs comprise binding regions that comprise a sequence independently selected from the group consisting of the sgRNA binding region sequences encoded by the 19 nucleotides at the 3' end of SEQ ID NOs:410,596-633,445.

In some cases the, or the at least, 1; 2; 3; 5; 10; 100; 1,000; 10,000; 100,000; or 200,000 structurally distinct sgRNAs comprise binding regions that are independently selected from the group consisting of the sgRNA binding region sequences encoded by SEQ ID NOs:633,446-857,995. In some cases the, or the at least, 1; 2; 3; 5; 10; 100; 1,000; 10,000; 100,000; or 200,000 structurally distinct sgRNAs comprise binding regions that comprise a sequence independently selected from the group consisting of the sgRNA binding region sequences encoded by the 19 nucleotides at the 3' end of SEQ ID NOs:633,446-857,995.

In some cases the, or the at least, 1; 2; 3; 5; 10; 100; 1,000; 10,000; 100,000; 200,000; or 400,000 structurally distinct sgRNAs comprise binding regions that are independently selected from the group consisting of the sgRNA binding region sequences encoded by SEQ ID NOs:26-410,595 or SEQ ID NOs:410,596-857,995. In some cases the, or the at least, 1; 2; 3; 5; 10; 100; 1,000; 10,000; 100,000; 200,000; or 400,000 structurally distinct sgRNAs comprise binding regions that comprise a sequence independently selected from the group consisting of the sgRNA binding region sequences encoded by the 19 nucleotides at the 3' end of SEQ ID NOs:26-410,595 or SEQ ID NOs:410,596-857,995.

In some cases, the sgRNAs are selected to inhibit transcription of human target loci (e.g., targeted to optimized human CRISPRi target sites), activate transcription of human target loci (e.g., targeted to optimized human CRISPRa target sites), inhibit transcription of mouse target loci (e.g., targeted to optimized mouse CRISPRi target sites), or activate transcription of mouse target loci (e.g., targeted to optimized mouse CRISPRa target sites).

In some cases, the dCas9 comprises a dCas9 domain and an epitope fusion domain, and wherein the plurality of cells further comprise an affinity agent, wherein the affinity agent has affinity to the epitope fusion domain and comprises a transcriptional activator. In some cases, the library of sgRNAs are targeted to a region between 0-750 bp upstream of the transcription start site of the targeted genes. In some cases, the transcriptional activator comprises a VP16 domain. In some cases, the transcriptional activator comprises a VP64 domain. In some cases, wherein the transcriptional activator comprises a plurality of VP64 domains.

In some cases, the epitope fusion domain comprises a GCN4 epitope and the affinity agent has affinity for the GCN4 epitope. In some cases, the epitope fusion domain comprises a plurality of GCN4 epitopes. In some cases, the dCas9 comprises an amino acid sequence of SEQ ID NO:4. In some cases, the affinity agent comprises an amino acid sequence of SEQ ID NO:5.

In some cases, the quantitating the frequency comprises deep sequencing. In some cases, the deep sequencing comprises sequencing with a redundancy of at least about 10. In some cases, the selecting the cells on the basis of the phenotype comprises culturing the cells, thereby selecting the cells on the basis of cellular proliferation. In some cases, the culturing is performed in the presence of a selection agent. In some cases, the selection agent is a chemotherapeutic, a DNA damaging agent, a cytotoxic agent, a growth factor, a transcription factor, a kinase, a drug, an exogenous gene under the control of a heterologous promoter, or a hormone. In some cases, the selecting the cells on the basis of the phenotype comprises selecting the cells on the basis of protein expression, RNA expression, or protein activity. In some cases, the selecting the cells on the basis of the phenotype comprises fluorescence activated cell sorting, affinity purification of cells, or selection based on cell motility.

In some cases, the specific sgRNAs that are overrepresented or underrepresented within the selected cells are overrepresented or underrepresented relative to the frequency of the corresponding sgRNAs in the sgRNA library. In some cases, the method further comprises contacting a plurality of control cells with the sgRNA library, wherein the plurality of control cells are not subject to the selecting on the basis of the phenotype, and the sgRNAs that are overrepresented or underrepresented in the selected cells are overrepresented or overrepresented relative to their frequency in the plurality of control cells. In some cases, the sgRNAs that are overrepresented or underrepresented in the selected cells are overrepresented or underrepresented relative to their frequency in the cells at an earlier time point in the culturing of the cells.

In some cases, the sgRNA is encoded by an expression cassette in the cell, the expression cassette comprising a promoter operably linked to a polynucleotide encoding the sgRNA. In some cases, the promoter operably linked to the polynucleotide encoding the sgRNA is inducible. In some cases, the nuclease deficient sgRNA-mediated nuclease (dCas9) is encoded by an expression cassette in the cell, the expression cassette comprising a promoter operably linked to a polynucleotide encoding the dCas9. In some cases, the promoter operably linked to the polynucleotide encoding the dCas9 is inducible. In some cases, the plurality of cells comprise a tetracycline transactivator, and wherein the method comprises expression of dCas9 under the control of a tetracycline inducible promoter in the absence of tetracycline or other exogenous inducer of the tetracycline inducible promoter. In some cases, the plurality of cells are contacted with a library of structurally distinct short hairpin RNAs (shRNA).

In some embodiments, the present invention provides a method of identifying a lead compound for treatment of a phenotype, the method comprising: performing any of the foregoing methods, thereby identifying a genetic element that modulates the phenotype; and identifying or screening for a lead compound that modulates expression of the genetic element; expression of a gene operably linked to the genetic element, or activity of a peptide encoded by the genetic element or a gene operably linked to the genetic element.

In some embodiments, the present invention provides a method of identifying interacting genetic elements, the method comprising: (i) performing any of the foregoing methods, thereby identifying a plurality of structurally distinct sgRNAs that target genetic elements that modulate the phenotype; (ii) contacting a plurality of interaction test cells with a library comprising a plurality of pairwise combinations of the structurally distinct sgRNAs identified in (i); (iii) selecting the test cells on the basis of the phenotype; and (iv) quantitating the frequency of the pairwise combinations of structurally distinct sgRNAs within the population of selected cells, wherein the pairwise combinations of structurally distinct sgRNAs that are overrepresented or underrepresented in the selected cells are predicted to target interacting genetic elements.

In some cases, the pair wise combinations of structurally distinct sgRNAs comprise a first member and a second member of the pair, and wherein the first member and second member target unlinked genetic elements. In some cases, the pairwise combinations of structurally distinct sgRNAs that are overrepresented or underrepresented in the selected cells are overrepresented or underrepresented relative to the frequency of the members of that pairwise combination in the selected cells of (i).

In some embodiments, the present invention provides a method of optimizing an sgRNA, the method comprising: performing any of the foregoing methods, wherein the plurality of structurally distinct sgRNAs target different regions within or next to a single genetic element, wherein the most overrepresented or underrepresented sgRNAs in the selected cells are identified as optimized sgRNAs that target the genetic element.

In some embodiments, the present invention provides a small guide RNA (sgRNA) comprising from 5' to 3': a binding region, of between about 19 and about 21 nucleotides in length; a 5' hairpin region, comprising: a unique endonuclease site; and fewer than four consecutive uracil nucleotides; or a length of at least 31 nucleotides; and a 3' hairpin region; and a transcription termination sequence, wherein the small guide RNA is configured to form a complex with a small guide RNA-mediated nuclease, the complex having increased stability or activity relative to a complex containing a small guide RNA-mediated nuclease and a small guide RNA comprising at least 95% identity to SEQ ID NO:6 or a complement thereof.

In some cases, the 5' hairpin region comprises fewer than four consecutive uracil nucleotides and a length of at least 31 nucleotides. In some cases, the unique endonuclease cut site is a BlpI site. In some cases, the small guide RNA has 19-25 or 21-28 nucleotides between the unique endonuclease site and the 5' end. In some cases, the small guide RNA comprises a binding region encoded by a sequence selected from the group consisting of (i) SEQ ID NOs:26-205,305; (ii) SEQ ID NOs:205,306-410,595; (iii) SEQ ID NOs:410, 596-633,445; (iv) SEQ ID NOs:633,446-857,995; (v). SEQ ID NOs:26-410,595; or (vi) SEQ ID NOs: 410,596-857,995. In some cases, the small guide RNA comprises a binding region encoded by a sequence selected from the group consisting of the 19 nucleotides at the 3' end of (i) SEQ ID NOs:26-205,305; (ii) SEQ ID NOs:205,306-410,595; (iii) SEQ ID NOs:410,596-633,445; (iv) SEQ ID NOs:633,446-857,995; (v). SEQ ID NOs:26-410,595; or (vi) SEQ ID NOs: 410,596-857,995.

In some embodiments, the present invention provides a method of constructing a library of any one of the foregoing small guide RNAs (sgRNAs), the method comprising: providing a polynucleotide encoding a sgRNA scaffold, the scaffold comprising from the 5' to 3' end: a unique endonuclease site, the unique endonuclease site having been cleaved by an endonuclease that recognizes the site; at least a portion of a 5' hairpin region comprising fewer than four consecutive uracil nucleotides or a length of at least 31 nucleotides; a 3' hairpin region; and a transcription termination sequence, chemically synthesizing a library of binding region encoding sequences containing, at the 3' end, a portion of a small guide RNA 5' hairpin region, and a region that complements the 3' unique endonuclease site of the small guide RNA scaffold; and ligating the library of binding region encoding sequences to the small guide RNA scaffold, wherein the small guide RNAs are configured to form a complex with a small guide RNA-mediated nuclease, the complex having increased stability or activity relative to a complex containing a small guide RNA-mediated nuclease and a small guide RNA comprising at least 95% identity to SEQ ID NO:6 or a complement thereof.

In some embodiments, the present invention provides a library of small guide RNAs (sgRNAs) that target a plurality of target genes comprising at least 2; 3; 4; 5; 6; 8; 10; 100; 1,000; 10,000; 50,000; 75,000; 100,000; 200,000; 400,000 or more structurally distinct sgRNAs, or a library of small guide RNA encoding sequences, or a library of small guide RNA binding region encoding sequences, as described in the foregoing embodiments, cases, or examples. In some cases, the sgRNAs are targeted to a region between 0-750 bp upstream of the transcription start site of the targeted genes. In some cases, the sgRNAs are targeted to a region between 0-1000 bp downstream of the transcription start site of the targeted genes. In some cases, the majority of the targeted genes are targeted with, targeted with no more than, or targeted with fewer than, 25, 20, 15, 11, 10, 6, 5, 4, or 3 structurally distinct sgRNAs. In some cases, the majority of sgRNAs are targeted to a region predicted to be accessible to sgRNA binding. In some cases, the region predicted to be accessible to sgRNA binding is selected from the group consisting of a region having a low micrococcal nuclease signal, a region having a high DNA polymerase III chromatin immunoprecipitation signal, and a region having a high run-on sequencing signal, or a combination thereof. In some cases, the region predicted to be accessible to sgRNA binding has a low micrococcal nuclease signal, a high DNA polymerase II chromatin immunoprecipitation signal, and a high run-on sequencing signal. In some cases, the majority of sgRNAs do not contain three or more or four or more repeated nucleotides, or do not contain three or more or four or more repeated U's, A's, G's, C's, or a combination thereof, excluding the 3' transcription termination sequence. In some cases, the majority of sgRNAs are targeted to a region predicted to be optimal for gene modulation by the dCas9-fusion protein. In some cases, at least $10^4$ genes are targeted, and the library contains fewer than $2.5 \times 10^5$, fewer than $2 \times 10^5$, fewer than $1 \times 10^5$, about $5 \times 10^4$, or fewer than $5 \times 10^4$ structurally distinct sgRNAs. In some cases, the sgRNAs are selected to have a binding region encoded by a sequence selected from the group consisting of SEQ ID NOs:26-410,595; selected from the group consisting of SEQ ID NOs: 410,596-857,995. In some cases, the sgRNAs are selected to have a binding region encoded by a sequence comprising the 19 nucleotides at the 3' end of any one or more (e.g., 2; 3; 4; 5; 10; 20; 40; 50; 100; 1,000; 5,000; 10,000; 15,000; 20,000; 50,000; 100,000; 200,000; 300,000; or 400,000, or more) or all of SEQ ID NOs:26-410,595; or any one or more (e.g., 2; 3; 4; 5; 10; 20; 40; 50; 100; 1,000; 5,000; 10,000; 15,000; 20,000; 50,000; 100,000; 200,000; 300,000; or 400,000, or more) or all of SEQ ID NOs: 410,596-857,995.

BRIEF DESCRIPTION OF THE DRAWINGS

FIG. 1A Depicts strategy for the massively parallel determination of growth or toxin resistance phenotypes caused by sgRNAs expressed in mammalian cells that also express dCas9 or dCas9-derived fusion constructs. Two types of large libraries can be used to define rules for CRISPRi/a or to perform genome scale screens to query the function of many genes in a pooled screen. FIG. 1B A map showing CRISPRi activity for all 49 genes in defined windows relative to the TSS of each gene. sgRNAs targeting the window of −50 to +350 bp around the TSS of a gene have maximal activity. FIG. 1C A schematic showing the genomic organization, GC content, and repetitive elements around the TSS of the gene, VPS54, across a 10 kb window targeted by the tiling sgRNA library. Many sgRNAs targeting dCas9 (top) and dCas9-KRAB (bottom) to VPS54 promote resistance to ricin. Each sgRNA is represented by one black dot. The data are displayed as a phenotype signed Z score (See methods of Example 6). FIG. 1D A sliding-window average of 49 genes targeted in a test sgRNA library is shown as a shaded region (top and bottom). The variable line between the 95th percentile and 5th percentile range displays median sgRNA activity in a defined window for each gene. The defined differentially shaded region in the center region of the bottom graph is the observed average window of maximum CRISPRi activity. The data are displayed as a phenotype signed Z score. FIG. 1E Depicts ricin resistance phenotypes comparing CRISPRi to RNAi for genes previously established to cause ricin resistance phenotypes when knocked down by RNAi. The data is displayed as a mean phenotype signed Z score for 10 subsampled sgRNAs or siRNAs.

FIG. 3A A schematic of the dCas9-SUN-tag+scFV-VP64+ sgRNA system for CRISPRa. Each component of the system is stably expressed in K562 cells. FIG. 3B The activity of sgRNAs in K562 cells expressing each component of CRISPRa, as a function of the distance of the sgRNA site to the TSS of the targeted gene; gene activation results in a negative ricin phenotype score. Top, many sgRNAs targeting VPS54 sensitize cells to ricin; Bottom, sliding-window average of all 49 genes targeted by our test library is shown in shaded. The median activity is shown with a variable line while the window of maximal activity is shown as a differentially shaded region. The data is displayed as a phenotype signed z-score. FIG. 3C Ricin resistance phenotypes for CRISPRa are anti-correlated to phenotypes for CRISPRi (dCas9-KRAB) for select genes. For each gene, a p-value is calculated using CRISPRi/a sgRNA activity relative to a negative control distribution for 24 subsampled sgRNAs. FIG. 3D CRISPRi knockdown and CRISPRa activation of the same gene can have opposing effects on the ricin resistance phenotype in both a primary screen and single sgRNA validation experiments. Data is represented as the mean and standard deviation of replicates (N=3). FIG. 3E CRISPRi knockdown and CRISPRa activation can modulate expression levels of a gene (as quantified by qPCR) over several orders of magnitude.

FIG. 4A A genome-scale CRISPRi screen was carried out in replicate in the human K562 cell line. Three classes of negative control sgRNAs are shown non-targeting sgRNAs, sgRNAs targeting Y-chromosomal genes, and sgRNAs targeting olfactory genes show no reproducible phenotypes. A subset of sgRNAs in the library strongly deplete in a reproducible manner (black). FIG. 4B Co-expression of sgRNAs and dCas9-KRAB is not toxic in K562 cell lines over 16 days. FIG. 4C Gene set enrichment analysis was performed for several essential cellular complexes. A histogram of gene distribution is shown under the GSEA curve. FIG. 4D The top 10 DAVID annotation clusters identified in our growth screen are strongly enriched for known essential cellular processes.

FIGS. 5A-5H: CRISPRi Gene Silencing is Robustly Inducible and Reversible and Non-Toxic. FIG. 5A A schematic depicting the lentiviral expression construct encoding inducible KRAB-dCas9. FIG. 5B Western blot analysis of inducible KRAB-dCas9 in the absence, presence, and after washout of doxycycline. Samples were collected daily from the same NegCtrl-4 sgRNA-expressing cells processed for RT-qPCR in FIG. 5C. FIG. 5C CRISPRi mediated gene repression is reversible. K562 cells expressing two sgRNAs targeting RAB1A were grown with or without doxycycline or doxycycline for 10 days or doxycycline was withdrawn at day 4. RAB1A mRNA levels were measured at each indicated time point by qPCR. FIGS. 5D and 5E Competitive growth assays performed with inducible CRISPRi K562 cells transduced with the indicated sgRNAs in the presence and absence of doxycycline. Data represent the mean of replicates (N=3) normalized to NegCtrl-1 results. Error bars represent standard deviation. FIGS. 5F and 5G A CRISPRi sub-library screen for effects on cell growth was performed with inducible CRISPRi K562 cells in the presence and absence of doxycycline. FIG. H Cumulative growth curves from the sub-library screen represented in FIGS. 5F and 5G show no bulk changes to growth caused by induction of KRAB-dCas9. Data represent the mean of replicate infections each screened in duplicate.

FIG. 6A A proposed model for CTx-DTA binding, retrograde trafficking, retro-translocation and cellular toxicity. FIG. 6B Gene set enrichment analysis of top hits from two replicate genome-scale CRISPRi screens for genes modulating sensitivity to CTx-DTA demonstrates strong enrichment for genes in known host pathways hijacked/targeted by CTx-DTA. FIG. 6C Overview of top hit genes detected by the CTx-DTA screen. Many genes fall into pathways, or encode subunits of the same physical complex. Pathways expected based on previous knowledge of CTx-DTA action (ganglioside biosynthesis, diphthamide biosynthesis, retrograde trafficking, ERAD, proteasome, translation) are each represented by several top hits, illustrating the robustness of CRISPRi based screening.

FIG. 7A-FIG. 7C A representative western blot and quantification of cholera toxin trafficking in cells expressing a negative control sgRNA or an sgRNA targeting SEL1L or B4GALNT1. Cholera toxin is distributed in both the cytosolic and membrane fractionation in control cells and according to their proposed function in CTx binding is blocked when B4GALNT1 is repressed or CTx is trapped in the ER upon repression of SEL1L. FIG. 7D Validation of CTx-DTA screen phenotypes with single sgRNA re-test experiments. Data are represented as the mean and standard deviation of replicates (N=3). FIG. 7E CRISPRi knockdown of 5 hit genes (15sgRNAs) identified in the CTx-DTA screen was quantified by qPCR. The gray shaded region denotes sgRNAs showing at least 90% knockdown for each gene. FIG. 7F Receiver operating characteristic (ROC) curve showing the performance of an improved sgRNA predictive score. FIG. 7G Simulation of library performance with decreasing numbers of sgRNAs targeting each gene. The phenotype for hit genes was calculated as the average of the top 3 most active sgRNAs, and overall library performance was expressed as the mean phenotype of all hit genes. The size of the library was computationally compacted by randomly subsampling sgRNAs or selecting sgRNAs based on the predictive score, and the remaining library activity is plotted as a percent of the full 10 sgRNA per gene library activity.

FIGS. 8A and 8B The formulas for deriving cellular phenotype from measurements of cell fraction in a population at discrete timepoints. Cells with a given genotype have an intrinsic growth rate g, often expressed as cell doublings per day. The $\log_2$ enrichment ($\log_2 e$) of cells with a specific genotype in a population can be calculated from the fraction of cells in the population at the endpoint t versus that fraction at t0. In order to express this as the growth rate relative to wild-type ($\gamma$), $\log_2 e$ is normalized to the median $\log_2 e$ of the negative control set and then divided by t. Similarly, the phenotype of cells exposed to a selective pressure (e.g., toxin treatment) can calculated from the $\log_2 e$ of treated and untreated populations to obtain $\rho$, which is +1 for completely resistant cells and −1 for cells with 2-fold sensitivity to the pressure relative to wild-type. FIG. 8C In order to quantify the strength of individual sgRNA activity relative to noise in the experiment, sgRNA phenotype was divided by the standard deviation of negative control phenotypes to yield the z-score. For analyses of sgRNA strength in tiling screens, in which genes had known knockdown phenotypes for either sensitivity or resistance, z-scores were re-signed to give positive values where the phenotypes agreed with the expected phenotype and negative values otherwise.

FIG. 9A-FIG. 9G: Highly active CRISPRi sgRNAs are close to the TSS, short and do not contain nucleotide homopolymers. FIG. 9A-FIG. 9B For several example genes, the phenotypes observed for sgRNAs expressed in dCas9 or dCas9-KRAB cells as a function of their position with respect to the TSS are depicted. Each point is an sgRNA. FIG. 9C Shorter sgRNAs have, on average, significantly higher activity. Each point represents an sgRNA, with lines connecting related sgRNAs that target the same PAM site but have increasing protospacer base pair length. Black lines represent the median activity for sgRNAs of specific lengths. sgRNAs are depicted if there are multiple sgRNAs targeting the same site and at least one sgRNA at that site is highly active (phenotype-signed z-score≥5). FIG. 9D sgRNA sequences with very high or very low GC content are less active. FIG. 9E The presence of homopolymers (AAAA, GGGG, UUUU) within an sgRNA reduces activity on average. FIG. 9F The DNA strand targeted by an sgRNA has no effect on activity. FIG. 9G A comparison of a subset of sgRNAs selected based on CRISPRi activity rules versus our previously published shRNA library. For each gene, the Mann-Whitney p-value was calculated using sgRNA or shRNA activity relative to a negative control distribution using 24 shRNAs or 24 sgRNAs. The 24 shRNAs and sgRNAs were randomly selected 100 times from the shRNA library and sgRNAs meeting position and length rules, respectively, and the median and SD $\log_{10}$ p-value are displayed.

FIG. 11A The activity of sgRNAs in a CRISPRa cell line as a function of the distance of the sgRNA site to the TSS of the targeted gene for four example genes. Top, ARL1 and ST3GAL4 activation results in ricin resistance; bottom, SURF4 and RAB1A activation results in ricin sensitivity. FIG. 11B A sliding-window average only for genes with a significant CRISPRa ricin resistance phenotype targeted by our test library is shown as a shaded region. The median activity is shown with a variable line while the window of maximal activity is shown in a differentially shaded region. The data is displayed as a phenotype-signed z-score.

FIG. 12A Competitive growth assays performed with inducible CRISPRi K562 cells transduced with the indicated RAB1A-targeting sgRNAs in the presence of doxycycline. Data represented as the mean and standard deviation of replicates (N=3). FIG. 12B CRISPRi knockdown of hit genes identified in the genome-scale growth screen (9 sgRNAs) was quantified by qPCR after two days of doxycycline treatment. The gray shaded region denotes sgRNAs showing at least 90% knockdown for each gene. See also FIGS. 5D and 5E.

FIG. 13A-FIG. 13E: A Genome-Scale CRISPRi Screen Reveals Known and New Pathways and Complexes Governing the Response to a Choler-Diptheria Fusion Toxin. FIG. 13A Two replicate genome-scale CRISPRi screens for CTx-DTA sensitivity show high reproducibility and robust enrichment and sensitization for individual sgRNAs. FIGS. 13B-13E Overview of top hit genes detected by the CTx-DTA screen. Many genes fall into pathways, or encode subunits of the same physical complex. Pathways expected based on previous knowledge of CTx-DTA action (ganglioside biosynthesis, diphthamide biosynthesis, retrograde trafficking, ERAD, proteasome, translation) are each represented by several top hits, illustrating the robustness of CRISPRi based screening.

FIG. 14A sgRNAs with longer protospacers are less active. FIG. 14B sgRNAs with poly-U homotrimers, homotetramers or more have decreased activity. FIG. 14C Overall purine content of sgRNAs correlates with increased activity. FIG. 14D sgRNA activity varies depending on the base immediately following the PAM. FIG. 14E sgRNA activity is optimal within a window from +25 to +100 bp.

FIG. 16A-FIG. 16C: Depict a flow chart for identifying optimized sgRNA binding region encoding sequences.

DEFINITIONS

Figure 1A:
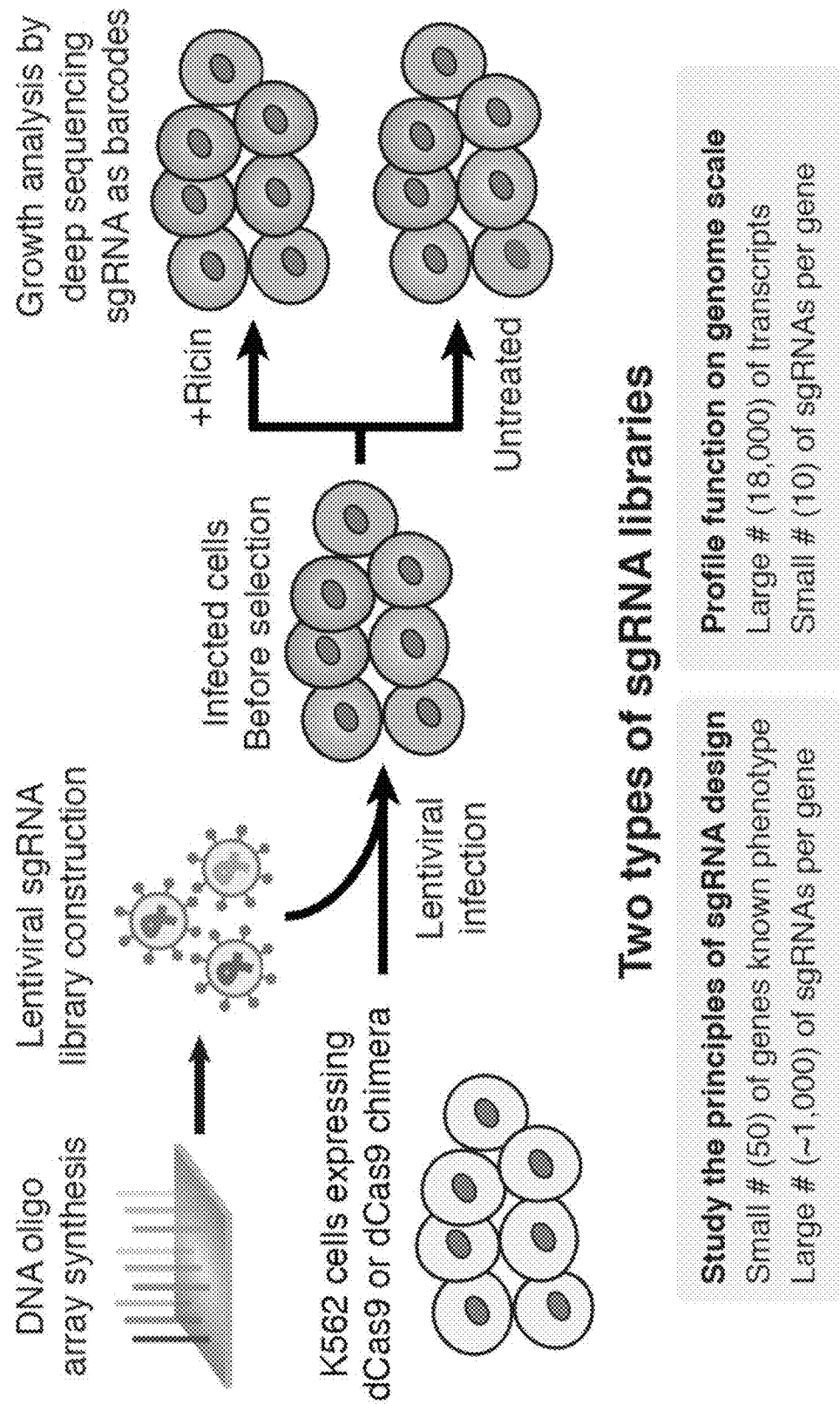
FIGS. 1A-1E: A Tiling sgRNA Screen Defines Rules for CRISPRi Activity at Endogenous Genes in Human Cells.

As used in this specification and the appended claims, the singular forms "a," "an," and "the" include plural reference unless the context clearly dictates otherwise.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. The reporter can also be an enzyme that generates a detectable signal when contacted with an appropriate substrate. The reporter can be an enzyme that catalyzes the formation of a detectable product. Suitable enzymes include, but are not limited to, proteases, nucleases, lipases, phosphatases and hydrolases. The reporter can encode an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton and Vapnek (1979) Nature 282: 864-869); luciferase (lux); β-galactosidase; LacZ; β-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labeled antibody that specifically recognizes the epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. In some cases, conservatively modified variants of Cas9 or sgRNA can have an increased stability, assembly, or activity as described herein.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N.Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or subsequences that are the same or have a specified percentage of amino acid residues or nucleotides that are the same. For example, a core small guide RNA (sgRNA) sequence responsible for assembly and activity of a sgRNA:nuclease complex has at least 80% identity, preferably 85%, 90%, 91%, 92%, 93, 94%, 95%, 96%, 97%, 98%, 99%, or 100% identity, to a reference sequence, e.g., one of SEQ ID NOs:6-11), when compared and aligned for maximum correspondence over a comparison window, or designated region as measured using one of the following sequence comparison algorithms or by manual alignment and visual inspection. As another example, a Cas9 sequence responsible for assembly and activity of a sgRNA:nuclease complex has at least 80% identity, preferably 85%, 90%, 91%, 92%, 93, 94%, 95%, 96%, 97%, 98%, 99%, or 100% identity, to a reference sequence, e.g., one of SEQ ID NOs:1-4), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. With regard to amino acid sequences, preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) J. Mol. Biol. 215: 403-410 and Altschul et al. (1977) Nucleic Acids Res. 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, Proc. Natl. Acad. Sci. USA 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence. Yet another indication that two polypeptides are substantially identical is that the two polypeptides retain identical or substantially similar activity.

A "translocation sequence" or "transduction sequence" refers to a peptide or protein (or active fragment or domain thereof) sequence that directs the movement of a protein from one cellular compartment to another, or from the extracellular space through the cell or plasma membrane into the cell. Translocation sequences that direct the movement of a protein from the extracellular space through the cell or plasma membrane into the cell are "cell penetration peptides." Translocation sequences that localize to the nucleus of a cell are termed "nuclear localization" sequences, signals, domains, peptides, or the like. Examples of translocation sequences include, without limitation, the TAT transduction domain (see, e.g., S. Schwarze et al., Science 285 (Sep. 3, 1999); penetratins or penetratin peptides (D. Derossi et al., Trends in Cell Biol. 8, 84-87); Herpes simplex virus type 1 VP22 (A. Phelan et al., Nature Biotech. 16, 440-443 (1998), and polycationic (e.g., polyarginine) peptides (Cell Mol. Life Sci. 62 (2005) 1839-1849). Further translocation sequences are known in the art. Translocation peptides can be fused (e.g. at the amino or carboxy terminus), conjugated, or coupled to a compound of the present invention, to, among other things, produce a conjugate compound that may easily pass into target cells, or through the blood brain barrier and into target cells.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize the RNA-mediated nuclease, Cas9 in complex with guide and activating RNA to recognize and cleave foreign nucleic acid. Methods and compositions for controlling inhibition and/or activation of transcription of target genes, populations of target genes (e.g., controlling a transcriptome or portion thereof) are described, e.g., in Cell. 2014 Oct. 23; 159(3):647-61, the contents of which are incorporated by reference in the entirety for all purposes.

Cas9 homologs are found in a wide variety of eubacteria, including, but not limited to bacteria of the following taxonomic groups: Actinobacteria, Aquificae, Bacteroidetes-Chlorobi, Chlamydiae-Verrucomicrobia, Chlroflexi, Cyanobacteria, Firmicutes, Proteobacteria, Spirochaetes, and Thermotogae. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21.

As used herein, "activity" in the context of CRISPR/Cas activity, Cas9 activity, sgRNA activity, sgRNA:nuclease activity and the like refers to the ability to bind to a target genetic element and/or modulate transcription at or near the target genetic element. Such activity can be measured in a variety of ways as known in the art. For example, expression, activity, or level of a reporter gene, or expression or activity of a gene encoded by the genetic element can be measured.

DETAILED DESCRIPTION OF THE INVENTION

I. Introduction

Described herein are methods and compositions for modulating the transcription of genomic regions at or near a target genetic element. The methods and compositions are based a CRISPR/Cas system that employs an optimized small guide RNA (sgRNA) and a nuclease deficient sgRNA-mediated nuclease (dCas9) and/or an sgRNA-mediated nuclease (Cas9). The sgRNA contains a binding region that provides highly specific binding to the target genetic element. Exemplary sgRNA binding region encoding sequences can include, but are not limited to, sequences that comprise or consist of the 19 nucleotides at the 3' end of any one of SEQ ID NOs:26-857,995. Exemplary sgRNA binding region encoding sequences can additionally or alternatively include, but are not limited to, sequences that comprise or consist of any one of SEQ ID NOs:26-857,995.

The sgRNA and the dCas9 can form a complex that specifically binds at or near the target genetic element. The dCas9 can be a fusion between the nuclease deficient dCas9 domain and a domain that provides a transcriptional modulation function. The methods and compositions can be used to target genetic elements as further described herein.

For example, the methods and compositions can be used to perform large (e.g., genome-wide) screens for genetic elements involved in the modulation of various phenotypes of interest. In some cases, previous screening techniques were impractical for performing large scale screens due to the size of the library required. For example, shRNA genome screens (e.g., Bassik et al., Cell. 2013 Feb. 14; 152(4):909-22) can require at least 25 shRNAs per targeted gene to ensure a high probability of transcriptionally repressing each gene. As described herein, the present inventors have discovered methods for designing sgRNAs and sgRNA libraries that target genetic elements with a high probability of altering the transcription of the targeted genetic element to a detectable degree. In some cases, the methods and compositions described herein can provide a library of sgRNAs of, of about, or of less than 25, 24, 23, 22, 21, 20, 15, 14, 13, 12, 11, 10, 9, 8, 7, 6, 5, 4, 3 or fewer sgRNAs per targeted gene. In some cases, the sgRNAs of the library are optimized to have a high probability of effectively modulating (e.g., activating or inhibiting transcription) target genes. Due to the high probability of effective target gene modulation, the library can target a large number of genes without requiring a large number of sgRNAs per target gene and therefore without becoming too large for facile construction and use. In some cases, the library targets a large plurality of genes (e.g., a library that targets at least 90%, 95%, 99%, substantially all, or all of the genes in a genome).

II. Compositions

Described herein are compositions useful as components of a CRISPR/Cas system for targeting genetic elements. The components can be used in a screen to identify genetic elements that modulate a phenotype, to identify genetic interactions, to develop or identify optimized sgRNAs, or for lead compound discovery or improvement. The components include sgRNAs, sgRNA libraries, and sgRNA scaffolds, and dCas9 transcriptional modulators.

A. sgRNAs

Described herein are sgRNAs, sgRNA scaffolds, and sgRNA libraries. The sgRNAs can contain from 5' to 3': a binding region, a 5' hairpin region, a 3' hairpin region, and a transcription termination sequence. The sgRNA can be configured to form a stable and active complex with a small guide RNA-mediated nuclease (e.g., Cas9 or dCas9). In some cases, the sgRNA is optimized to enhance expression of a polynucleotide encoding the sgRNA in a host cell.

The 5' hairpin region can be between about 15 and about 50 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides in length). In some cases, the 5' hairpin region is between about 30-45 nucleotides in length (e.g., about 31, 32, 33, 34, 35, 36, 37, 38, 39, 40, 41, 42, 43, 44, or 45 nucleotides in length). In some cases, the 5' hairpin region is, or is at least about, 31 nucleotides in length (e.g., is at least about 31, 32, 33, 34, 35, 36, 37, 38, 39, 40, 41, 42, 43, 44, or 45 nucleotides in length). In some cases, the 5' hairpin region contains one or more loops or bulges, each loop or bulge of about 1, 2, 3, 4, 5, 6, 7, 8, 9, or 10 nucleotides. In some cases, the 5' hairpin region contains a stem of between about 10 and 30 complementary base pairs (e.g., 11, 12, 13, 14, 15, 16, 17, 18, 19, 20, 21, 22, 23, 24, 25, 26, 27, 28, 29, or 30 complementary base pairs).

In some embodiments, the 5' hairpin region can contain protein-binding, or small molecule-binding structures. In some cases, the 5' hairpin function (e.g., interacting or assembling with a sgRNA-mediated nuclease) can be conditionally activated by drugs, growth factors, small molecule ligands, or a protein that binds to the protein-binding structure of the 5' stem-loop. In some embodiments, the 5' hairpin region can contain non-natural nucleotides. For example, non-natural nucleotides can be incorporated to enhance protein-RNA interaction, or to increase the thermal stability or resistance to degradation of the sgRNA.

In some embodiments, the 5' hairpin region contains a unique endonuclease site. In some cases, the unique endonuclease site can introduce a bulge (e.g., a bulge of about 1, 2, 3, 4, 5, 6, 7, 8, 9, or 10 nucleotides). In an exemplary embodiment, the unique endonuclease site is a BlpI site. The unique endonuclease site can facilitate cloning of a binding region or a library of structurally distinct binding regions into an sgRNA scaffold as further described below.

The sgRNA can contain an intervening sequence between the 5' and 3' hairpin regions. The intervening sequence between the 5' and 3' hairpin regions can be between about 0 to about 50 nucleotides in length, preferably between about 10 and about 50 nucleotides in length (e.g., at a length of, or about a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides). In some cases, the intervening sequence is designed to be linear, unstructured, substantially linear, or substantially unstructured. In some embodiments, the intervening sequence can contain non-natural nucleotides. For example, non-natural nucleotides can be incorporated to enhance protein-RNA interaction or to increase the activity of the sgRNA:nuclease complex. As another example, natural nucleotides can be incorporated to enhance the thermal stability or resistance to degradation of the sgRNA.

The 3' hairpin region can contain an about 3, 4, 5, 6, 7, or 8 nucleotide loop and an about 4, 5, 6, 7, 8, 9, 10, 11, 12, 13, 14, 15, 16, 17, 18, 19, 20, 21, 22, 23, 24, or 25 nucleotide or longer stem. In some cases, the 3' hairpin region can contain a protein-binding, small molecule-binding, hormone-binding, or metabolite-binding structure that can conditionally stabilize the secondary and/or tertiary structure of the sgRNA. In some embodiments, the 3' hairpin region can contain non-natural nucleotides. For example, non-natural nucleotides can be incorporated to enhance protein-RNA interaction or to increase the activity of the sgRNA:nuclease complex. As another example, natural nucleotides can be incorporated to enhance the thermal stability or resistance to degradation of the sgRNA.

In some embodiments, the sgRNA includes a termination structure at its 3' end. In some cases, the sgRNA includes an additional 3' hairpin region, e.g., before the termination and after a first 3' hairpin region, that can interact with proteins, small-molecules, hormones, etc., for stabilization or additional functionality, such as conditional stabilization or conditional regulation of sgRNA:nuclease assembly or activity.

In some embodiments, the sgRNA forms an sgRNA:Cas9 or dCas9 complex that has increased stability and/or activity as compared to previously known sgRNAs or an sgRNA substantially identical to a previously known sgRNA. In some cases, the sgRNA forms an sgRNA:Cas9 or dCas9 complex that has increased stability and/or activity as compared to as an sgRNA encoded by:
SEQ ID NO:6 [N]$_{5-100}$GUUUUAGAGCUA-GAAAUAGCAAGUUAAAAUAAGGCUAGUCC GUUAUCAACUUGAAAAAGUGGCACCGAGUCG-GUGCUUUUUUU, where [N] represents a target specific binding region of between about 5-100 nucleotides (e.g., about 5, 10, 15, 20, 15, 30, 35, 40, 45, 50, 55, 60, 70, 80, or 90 nucleotides) that is complementary or substantially complementary to the target genetic element. In some embodiments, the binding region of the sgRNA is, or is about, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or more nucleotides in length. In some cases, the binding region of the sgRNA is between about 19 and about 21 nucleotides in length.

Generally, the binding region is designed to complement (e.g., perfectly complement) or substantially complement the target genetic element or elements. In some cases, the binding region can incorporate wobble or degenerate bases to bind multiple genetic elements. In some cases, the 19 nucleotides at the 3' or 5' end of the binding region are perfectly complementary the target genetic element or elements. In some cases, the binding region can be altered to increase stability. For example, non-natural nucleotides, can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, 60%). In some cases, the binding region, can be selected to begin with a sequence that facilitates efficient transcription of the sgRNA. For example, the binding region can begin at the 5' end with a G nucleotide. In some cases, the binding region can contain modified nucleotides such as, without limitation, methylated or phosphorylated nucleotides.

In some cases, the sgRNAs described herein form an sgRNA:nuclease complex with enhanced stability or activity as compared to SEQ ID NO:6, or an sgRNA 90, 95, 96, 97, 98, or 99% or more identical to SEQ ID NO:6. In some cases, the optimized sgRNAs described herein form an sgRNA:nuclease complex with enhanced stability or activity as compared to SEQ ID NO:6, or an sgRNA with fewer than 5, 4, 3, 2 or 1 nucleotide substitutions, additions, or deletions of SEQ ID NO:6.

As used herein, identity of an sgRNA to another sgRNA, such as an sgRNA to SEQ ID NO:6 is determined with reference to the identity to the nucleotide sequences outside of the binding region. For example, two sgRNAs with 0% identity inside the binding region and 100% identity outside the binding region are 100% identical to each other. Similarly, as used herein, the number of substitutions, additions, or deletions of an sgRNA as compared to another, such as an sgRNA compared to SEQ ID NO:6 is determined with reference to the nucleotide sequences outside of the binding region. For example, two sgRNAs with multiple additions, substitutions, and/or deletions inside the binding region and 100% identity outside the binding region are considered to contain 0 nucleotide substitutions, additions, or deletions.

As used herein, the structural distinctiveness of an sgRNA to another sgRNA is determined with reference to the binding region. Thus, for example, an sgRNA that is structurally distinct as compared to another sgRNA has a different binding region sequence. The sequence can be different by way of any one or more substitutions, additions, or deletions within the binding region.

In some embodiments, the sgRNA can be optimized for expression by substituting, deleting, or adding one or more nucleotides. In some cases, a nucleotide sequence that provides inefficient transcription from an encoding template nucleic acid can be deleted or substituted. For example, in some cases, the sgRNA is transcribed from a nucleic acid operably linked to an RNA polymerase III promoter. In such cases, sgRNA sequences that result in inefficient transcription by RNA polymerase III, such as those described in Nielsen et al., Science. 2013 Jun. 28; 340(6140):1577-80, can be deleted or substituted. For example, one or more consecutive uracils can be deleted or substituted from the sgRNA sequence. In some cases, the consecutive uracils are present in the stem portion of a stem-loop structure. In such cases, one or more of the consecutive uracils can be substituted by exchanging the uracil and its complementary base. For example, if the uracil is hydrogen bonded to a corresponding adenine, the sgRNA sequence can be altered to exchange the adenine and uracil. This "A-U flip" can retain the overall structure and function of the sgRNA molecule while improving expression by reducing the number of consecutive uracil nucleotides. In some cases, the sgRNA containing an A-U flip is encoded by:

SEQ ID NO:7 $[N]_{5-100}$GUUU$\underline{A}$AGAGCUAGAAAUAGCAAGUU$\underline{U}$AAAUAAGGCUAGUCC GUUAUCAAC-UUGAAAAAGUGGCACCGAGUCGGUGCUUUUUUU, where the A-U flipped nucleotides are underlined. In some cases, the optimized sgRNA is at least 90, 91, 92, 93, 94, 95, 96, 97, 98, or 99% identical or more to SEQ ID NO:7, or contains fewer than 10, 9, 8, 7, 6, 5, 4, 3, or 2 nucleotide additions, deletions, or substitutions compared to SEQ ID NO:7. Alternatively, the A-U pair can be replaced by a G-C, C-G, A-C, G-U pair. In some cases, the sgRNA is designed so that, with the exclusion of the transcription terminator sequence, it does not contain any run of four or more of A, U, G, or C.

In some embodiments, the sgRNA can be optimized for stability. Stability can be enhanced by optimizing the stability of the sgRNA:nuclease interaction, optimizing assembly of the sgRNA:nuclease complex, removing or altering RNA destabilizing sequence elements, or adding RNA stabilizing sequence elements. In some embodiments, the sgRNA contains a 5' stem-loop structure proximal to, or adjacent to, the binding region that interacts with the sgRNA-mediated nuclease. Optimization of the 5' stem-loop structure can provide enhanced stability or assembly of the sgRNA:nuclease complex. In some cases, the 5' stem-loop structure is optimized by increasing the length of the stem portion of the stem-loop structure. An exemplary sgRNA containing an optimized 5' stem-loop structure is encoded by:

SEQ ID NO:8 $[N]_{5-100}$GUUUUAGAGCUA$\underline{UGCUGG}$AAA$\underline{CAGCA}$UAGCAAG$\underline{UUAAAAU}$AAGGCUAGUCCGUUAUCAAC-UUGAAAAAGUGGCACCGAGUCGGUGCUUUUUU U, where the nucleotides contributing to the elongated stem portion of the 5' stem-loop structure are underlined. In some cases, the optimized sgRNA is at least 90, 91, 92, 93, 94, 95, 96, 97, 98, or 99% identical or more to SEQ ID NO:8, or contains fewer than 10, 9, 8, 7, 6, 5, 4, 3, or 2 nucleotide additions, deletions, or substitutions compared to SEQ ID NO:8.

In some embodiments, the 5' stem-loop optimization is combined with mutations for increased transcription to provide an optimized sgRNA. For example, an A-U flip and an elongated stem loop can be combined to provide an optimized sgRNA. An exemplary sgRNA containing an A-U flip and an elongated 5' stem-loop is encoded by:

SEQ ID NO: 9 $[N]_{5-100}$GUUU$\underline{A}$AGAGCUA$\underline{UGCUGG}$AAA$\underline{CAGCA}$UAGCAAGUU$\underline{U}$AAAU AAGGCUAGUCCGUUAUCAAC-UUGAAAAAGUGGCACCGAGUCGGUGCUUUUUU U, where the A-U flipped nucleotides and the nucleotides contributing to the elongated stem portion of the 5' stem-loop structure are underlined. In some cases, the optimized sgRNA is at least 90, 91, 92, 93, 94, 95, 96, 97, 98, or 99% identical or more to SEQ ID NO:9, or contains fewer than 10, 9, 8, 7, 6, 5, 4, 3, or 2 nucleotide additions, deletions, or substitutions compared to SEQ ID NO:9.

In some embodiments, a small guide RNA can include a unique endonuclease site to enable construction of large libraries with high fidelity. In some embodiments, the unique endonuclease site introduces a 1 bp bulge in the 5' hairpin region. An exemplary sgRNA containing a unique endonuclease site and 1 bp bulge in the 5' hairpin region is encoded by:

SEQ ID NO: 10 [N]$_{5-100}$GUUU<u>A</u>AGAGCUA AGCUGGAAA<u>CAGCA</u>UAGCAAGUUU<u>U</u>AAAU AAGGCUAGUCCGUUAUCAAC- UUGAAAAAGUGGCACCGAGUCGGUGCUUUUUU U, where the A-U flipped nucleotides, the 1 bp bulge, and the nucleotides contributing to the elongated stem portion of the 5' stem-loop structure are underlined. In some cases, the optimized sgRNA is at least 90, 91, 92, 93, 94, 95, 96, 97, 98, or 99% identical or more to SEQ ID NO:10, or contains fewer than 10, 9, 8, 7, 6, 5, 4, 3, or 2 nucleotide additions, deletions, or substitutions compared to SEQ ID NO:10.

In some embodiments, the small guide RNA is encoded by a polynucleotide that comprises or consists of:
SEQ ID NO:11 [N]$_{19-21}$GUUU<u>A</u>AGAGCUA AGCUGGAAA<u>CAGCA</u>UAGCAAGUUU<u>U</u>AAAU AAGGCUAGUCCGUUAUCAAC- UUGAAAAAGUGGCACCGAGUCGGUGCUUUUUU U, where the A-U flipped nucleotides, the 1 bp bulge, and the nucleotides contributing to the elongated stem portion of the 5' stem-loop structure are underlined. In some cases, the optimized sgRNA is at least 90, 91, 92, 93, 94, 95, 96, 97, 98, or 99% identical or more to SEQ ID NO:11, or contains fewer than 10, 9, 8, 7, 6, 5, 4, 3, or 2 nucleotide additions, deletions, or substitutions compared to SEQ ID NO:11.

sgRNAs can be modified by methods known in the art. In some cases, the modifications can include, but are not limited to, the addition of one or more of the following sequence elements: a 5' cap (e.g., a 7-methylguanylate cap); a 3' polyadenylated tail; a riboswitch sequence; a stability control sequence; a hairpin; a subcellular localization sequence; a detection sequence or label; or a binding site for one or more proteins. Modifications can also include the introduction of non-natural nucleotides including, but not limited to, one or more of the following: fluorescent nucleotides and methylated nucleotides.

In some embodiments, the sgRNAs are selected so as not to have significant off-target effects. In some cases, the similarity of an sgRNA binding region for off-target genetic element sequences can be determined. sgRNAs having a high similarity exceeding a pre-designated threshold can be filtered out. In some cases, candidate binding regions, including the protospacer adjacent motif (PAM) sequences can be scored using a scoring metric in a manual or automated fashion. sgRNA binding regions having an acceptable number of off-target mismatches can then be selected for synthesis.

An exemplary scoring metric is provided as follows: G1 of the PAM (e.g., NGG for *Streptococcus pyogenes* Cas9) is given a score of 40 if present and a score of 0 if absent. G2 of the PAM is given a score of 19 if present and a score of 0 if absent. N of the PAM is given a score of 0, whether present or absent. Region I, corresponding to the first 7 nucleotides of the binding region starting from the 5' end is given a score of 28 for every mismatch present. Region II, corresponding to the first 5 nucleotides of the binding region starting after the 3' end of Region I is given a score of 19 for every mismatch present. Region III, corresponding to the remaining nucleotides between Region II and the PAM is given a score of 10 for every mismatch present. Off-target binding at any given site can be estimated as 1−([Σ/ (mismatches*mismatch_score)]/40). In some cases, sgRNAs are selected that have a score according to the foregoing metric of less than or equal to 0. Thus, according to the foregoing exemplary scoring metric, an sgRNA having one mismatch in PAM G1 and no other mismatches would be selected. However, an sgRNA having one mismatch in PAM G1 and any other mismatch would not be selected for synthesis.

In some embodiments, the sgRNAs are targeted to specific regions at or near a gene. For example, an sgRNA can be targeted to a region at or near the 0-750 bp region 5' (upstream) of the transcription start site of a gene. In some cases, the 0-750 bp targeting of the region can provide, or provide increased, transcriptional activation by an sgRNA: dCas9 complex. For instance, a cell can be contacted with a dCas9 fused to a transcriptional activator or epitope fusion domain and an sgRNA, or library of sgRNAs, targeted to the 0-750 bp region 5' of the transcription start site of one or more genes.

As another example, an sgRNA can be targeted to a region at or near the 0-1000 bp region 3' (downstream) of the transcription start site of a gene. In some cases, the 0-1000 bp targeting of the region can provide, or provide increased, transcriptional repression by an sgRNA:dCas9 complex. For instance, a cell can be contacted with a dCas9 fused to a transcriptional repressor or epitope fusion domain and an sgRNA, or library of sgRNAs, targeted to the 0-1000 bp region 3' of the transcription start site of one or more genes.

In some embodiments, the sgRNAs are targeted to a region at or near the transcription start site (TSS) based on an automated or manually annotated database. For example, transcripts annotated by Ensembl/GENCODE or the APPRIS pipeline (Rodriguez et al., Nucleic Acids Res. 2013 January; 41(Database issue):D110-7 can be used to identify the TSS and target genetic elements 0-750 bp upstream (e.g., for targeting one or more transcriptional activator domains) or 0-1000 bp downstream (e.g., for targeting one or more transcriptional repressor domains) of the TSS.

In some embodiments, the sgRNAs are targeted to a genomic region that is predicted to be relatively free of nucleosomes. The locations and occupancies of nucleosomes can be assayed through use of enzymatic digestion with micrococcal nuclease (MNase). MNase is an endo-exo nuclease that preferentially digests naked DNA and the DNA in linkers between nucleosomes, thus enriching for nucleosome-associated DNA. To determine nucleosome organization genome-wide, DNA remaining from MNase digestion is sequenced using high-throughput sequencing technologies (MNase-seq). Thus, regions having a high MNase-seq signal are predicted to be relatively occupied by nucleosomes and regions having a low MNase-seq signal are predicted to be relatively unoccupied by nucleosomes. Thus, in some embodiments, the sgRNAs are targeted to a genomic region that has a low MNase-Seq signal.

In some cases, the sgRNAs are targeted to a region predicted to be highly transcriptionally active. For example, the sgRNAs can be targeted to a region predicted to have a relatively high occupancy for RNA polymerase II (PolII). Such regions can be identified by PolII chromatin immunoprecipitation sequencing (ChIP-seq), which includes affinity purifying regions of DNA bound to PolII using an anti-PolII antibody and identifying the purified regions by sequencing. Therefore, regions having a high PolII Chip-seq signal are predicted to be highly transcriptionally active. Thus, in some cases, sgRNAs are targeted to regions having a high PolII ChIP-seq signal as disclosed in the ENCODE-published PolII ChIP-seq database (Landt, et al., Genome Research, 2012 September; 22(9):1813-31).

As another example, the sgRNAs can be targeted to a region predicted to be highly transcriptionally active as identified by run-on sequencing or global run-on sequencing (GRO-seq). GRO-seq involves incubating cells or nuclei with a labeled nucleotide and an agent that inhibits binding of new RNA polymerase to transcription start sites (e.g., sarkosyl). Thus, only genes with an engaged RNA polymerase produce labeled transcripts. After a sufficient period of time to allow global transcription to proceed, labeled RNA is extracted and corresponding transcribed genes are identified by sequencing. Therefore, regions having a high GRO-seq signal are predicted to be highly transcriptionally active. Thus, in some cases, sgRNAs are targeted to regions having a high GRO-seq signal as disclosed in a published GRO-seq data (e.g., Core et al., Science. 2008 Dec. 19; 322(5909):1845-8; and Hah et al., Genome Res. 2013 August; 23(8):1210-23).

Also described herein are expression cassettes and vectors for producing sgRNAs in a host cell. The expression cassettes can contain a promoter (e.g., a heterologous promoter) operably linked to a polynucleotide encoding an sgRNA. The promoter can be inducible or constitutive. The promoter can be tissue specific. In some cases, the promoter is a U6, H1, or spleen focus-forming virus (SFFV) long terminal repeat promoter. In some cases, the promoter is a weak mammalian promoter as compared to the human elongation factor 1 promoter (EF1A). In some cases, the weak mammalian promoter is a ubiquitin C promoter or a phosphoglycerate kinase 1 promoter (PGK). In some cases, the weak mammalian promoter is a TetOn promoter in the absence of an inducer. In some cases, when a TetOn promoter is utilized, the host cell is also contacted with a tetracycline transactivator. In some embodiments, the strength of the selected sgRNA promoter is selected to express an amount of sgRNA that is proportional to the amount of Cas9 or dCas9. The expression cassette can be in a vector, such as a plasmid, a viral vector, a lentiviral vector, etc. In some cases, the expression cassette is in a host cell. The sgRNA expression cassette can be episomal or integrated in the host cell.

Also described herein are sgRNA scaffolds. sgRNA scaffolds are portions of an sgRNA that can serve as a recipient of a binding region, or portion thereof, for ease of cloning or other manipulation. In some embodiments, the sgRNA scaffold comprises all the regions of the sgRNA (e.g., 5' hairpin region, intervening region, 3' hairpin, and termination sequence) except for the binding region. Thus, the sgRNA scaffold comprises all the constant regions of the sgRNA. In some cases, the scaffold contains a unique endonuclease site at or near the 5' end of the 5' hairpin region. An exemplary unique endonuclease site is a BlpI site, as shown for example in SEQ ID NO:11. In some cases, the scaffold is present in a vector or expression cassette. For example, the scaffold can be configured to be operably linked to a promoter (e.g., a heterologous promoter) after ligation of a binding region. In some cases, the scaffold can be present in a shuttle or intermediate cloning vector. For example, the scaffold can be present in an *E. coli* cloning vector, and configured to accept ligation of a binding region, thereby providing an sgRNA that can be excised from the *E. coli* vector and ligated into a suitable host cell expression vector.
I In some embodiments, portions of the sgRNA scaffold are encoded in different expression cassettes, different vectors, or different intermediate cloning polynucleotides. For example, a portion of the sgRNA scaffold containing the 5' hairpin region and a unique restriction site may reside on an *E. coli* cloning vector. A binding region, or library of binding regions, can be cloned into the sgRNA scaffold portion. The binding region and 5' hairpin region can then be digested and ligated into a destination vector (e.g., a host cell expression vector) that provides one or more of an intervening region, a 3' hairpin region, and/or a 3' termination sequence.

The sgRNA scaffold can be used to generate libraries of structurally distinct sgRNAs. For example, a library of polynucleotides encoding structurally distinct binding regions can be synthesized or generated using methods known in the art including but not limited to solid phase DNA synthesis. In some cases, the solid phase synthesis is performed on a microarray slide or chip. The library of polynucleotides encoding the binding regions can be recovered, optionally purified (e.g., HPLC or PAGE), and cloned into an sgRNA scaffold to generate polynucleotides encoding a library of structurally distinct sgRNAs. Thus, the solid phase synthesis can be performed to generate the short (e.g., 19-21 nucleotide) binding region, while the constant regions are provided by the scaffold. In some embodiments, this combination of solid phase synthesis of the binding region and cloning into a scaffold can greatly increase the quality of the library as compared to synthesizing a larger portion of the sgRNA. For example, the synthesized region can contain fewer misincorporation errors (e.g., synthesized oligonucleotides of length N−1) that arise during synthesis of long polynucleotides.

Consequently, also described herein are libraries of sgRNAs, wherein the library contains a large number of sgRNAs having structurally distinct binding regions. The library can contain at least 10, 100; 1,000; 10,000; 50,000; or more structurally distinct sgRNAs. In some embodiments, the library contains less than about 50%, 25%, 15%, 10%, 1%, or fewer misincorporation (e.g., synthesized oligonucleotides of length N−1) errors.

In some embodiments, the library contains sgRNAs that target genetic elements that are at least about 5 bp apart in the genome of an organism. In some cases, completely or nearly overlapping sgRNAs can be enriched for the same or similar phenotype. Therefore enforcing a distance between targeted genetic elements of the sgRNAs can provide an sgRNA library with a larger variety of possible phenotypes as compared to a library of the same size having overlapping sgRNAs. In some cases, a majority, substantial majority, or at least 90% (e.g., at least 90, 95, or 99%) of the sgRNAs of an sgRNA library are targeted to non-overlapping genetic elements (e.g., genetic elements that are at least 1, 2, 3, 4, 5, 6, 7, 8, 9, 10, 11, 12, 13, 14, 15, 16, 17, 18, 19, or 20 bp apart).

In some embodiments, the library contains a plurality of sgRNAs, wherein the plurality of sgRNAs comprise binding regions that are designed according to one or more of the following criteria: designed to target a genetic element that is at least 5 bp apart from a genetic element targeted by another sgRNA of the library; designed to begin with a "G" nucleotide; designed to have a mismatch scoring metric for off-target genetic elements of below a pre-designated threshold (e.g., designed to have a mismatch scoring metric of less than or equal to 0); designed to target a region between, or between about, 0 and about 750 bp upstream of the transcription start site (TSS), or wherein a majority, substantial majority, or at least 90% (e.g., at least 90, 95, or 99%) of the sgRNAs are targeted to a region between, or between about, 0 and about 1000 bp downstream of the TSS of a gene; designed to target a region between, or between about, 0 and about 1000 bp downstream of the transcription start site (TSS), or wherein a majority, substantial majority, or at least 90% (e.g., at least 90, 95, or 99%) of the sgRNAs are targeted to a region between, or between about, 0 and about 100 bp downstream of the TSS of a gene; designed to target regions upstream or downstream of the TSS as annotated by Ensemble/ENCODE or the APPRIS pipeline; designed to lack any region containing four or more consecutive U, A, G, and/or C nucleotides; designed to have a GC percentage of between about 25% and 100%, or between about 30% and 95%; designed to target genetic elements having a low MNase-seq signal; designed to target genetic elements having a high PolII ChIP-seq signal; or designed to target genetic elements having a high GRO-seq signal.

In some embodiments, the sgRNA libraries can target a plurality of genetic elements with a high probability of substantially modulating the expression level of one or more genes, or portions thereof, at or near the targeted genetic element or modulating the expression level of the genetic element. In some embodiments, the sgRNA libraries can provide a high probability of substantial transcriptional modulation despite having a relatively low number of sgRNAs targeted to a gene or genetic element. For example, the sgRNA library can have less than, or less than about, 20, 19, 18, 17, 16, 15, 14, 13, 12, 11, 10, 9, 8, 7, 6, 5, 4, 3, or 2 sgRNAs targeted to each gene, genomic region, or genetic element. In comparison, other pooled techniques for large scale transcriptional modulation, such as methods utilizing shRNA libraries can require a higher level of redundancy to ensure a high probability of transcriptional modulation of targeted genes or genetic elements. In some embodiments, the sgRNA library has a median predicted probability of providing a detectable phenotype, as measured using a signed Z-score of at least, or at least about, 0.1, 0.2, 0.3, 0.4, 0.5, 0.6, 0.7, 0.8, 0.9, or higher. In some cases, the Z-score is between, or between about 0.1 and 2, 0.1 and 1, 0.1 and 0.9 or 1, 0.2 and 0.9 or 1, 0.3 and 0.9 or 1, 0.4 and 0.9 or 1, or 0.5 and 0.9 or 1.

In some embodiments, the Z-score is calculated using a method described in Kampmann et al., Proc Natl Acad Sci USA. 2013 Jun. 18; 110(25):E2317-26, or Bassik et al., Cell. 2013 Feb. 14; 152(4):909-22. For example, the phenotype of each sgRNA can be quantified, for growth ("gamma") or resistance to treatment ("rho"). To normalize these phenotypes, the quantified value for gamma or rho is divided by the standard deviation of negative-control sgRNA phenotypes. These standardized phenotypes represent the "z scores".

In some embodiments, sgRNA libraries can be double-sgRNA libraries. For example, the library can be a plurality of polynucleotides that each encode two sgRNAs. The sgRNAs can be pairwise combinations of sgRNAs that have already been identified as modulating a phenotype. Such libraries can be useful for identifying genetic interactions between the genetic elements targeted by each sgRNA of the pair.

B. Cas9

Described herein are guide RNA dependent nucleases and derivatives thereof. In some cases, the sgRNA-mediated nuclease is a Cas9 protein. For example, the sgRNA-mediated nuclease can be a type I, II, or III Cas9 protein. In some cases, the sgRNA-mediated nuclease can be a modified Cas9 protein. Cas9 proteins can be modified by any method known in the art. For example, the Cas9 protein can be codon optimized for expression in host cell or an in vitro expression system. Additionally, or alternatively, the Cas9 protein can be engineered for stability, enhanced target binding, or reduced aggregation.

The Cas9 can be a nuclease defective Cas9 (i.e., dCas9). For example, certain Cas9 mutations can provide a nuclease that does not cleave or nick, or does not substantially cleave or nick the target sequence. Exemplary mutations that reduce or eliminate nuclease activity include one or more mutations in the following locations: D10, G12, G17, E762, H840, N854, N863, H982, H983, A984, D986, or A987, or a mutation in a corresponding location in a Cas9 homologue or ortholog. The mutation(s) can include substitution with any natural (e.g., alanine) or non-natural amino acid, or deletion. An exemplary nuclease defective dCas9 protein is Cas9D10A&H840A (Jinek, et al., Science. 2012 Aug. 17; 337(6096):816-21; Qi, et al., Cell. 2013 Feb. 28; 152(5): 1173-83).

dCas9 proteins that do not cleave or nick the target sequence can be utilized in combination with an sgRNA, such as one or more of the sgRNAs described herein, to form a complex that is useful for transcriptional modulation of target nucleic acids as further explained below. The dCas9 can be targeted to one or more genetic elements by virtue of the binding regions encoded on one or more sgRNAs. Recruitment of dCas9 can therefore provide recruitment of additional effector functions as provided by polypeptides fused to the dCas9 domain. For example, a polypeptide comprising an effector function can be fused to the N and/or C-terminus of a dCas9 domain. In some cases, the polypeptide encodes a transcriptional activator or repressor. In other cases, the polypeptide encodes an epitope fusion that can be used to recruit one or more copies of an affinity agent. In some cases, the affinity agent is fused to a transcriptional activator or repressor.

In one embodiment, the dCas9 is a transcriptional activator and comprises a dCas9 domain and a transcriptional activator domain. In some cases, the dCas9 domain is fused to a p65 activation domain (p65AD). SEQ ID NO:1 is an exemplary dCas9 domain fused to p65AD. In some cases, the dCas9 fused to p65AD is at least about 90%, 95%, or 99% identical, or identical, to SEQ ID NO:1.

In some cases, the dCas9 domain transcriptional activator comprises a dCas9 domain fused to one or more copies of a VP8 activation domain (e.g., fused to a VP8, VP16, or VP64 domain). SEQ ID NO:2 is an exemplary dCas9 domain fused to VP16 or VP64. In some cases, the dCas9 fused to a VP16 domain is at least about 90%, 95%, or 99% identical, or identical, to SEQ ID NO:2.

In some embodiments, the dCas9 is a transcriptional repressor and comprises a dCas9 domain and a transcriptional repressor domain. In some cases, the dCas9 domain is fused to a Krüppel associated box (KRAB) repressor domain. SEQ ID NO:3 is an exemplary dCas9 domain fused to a KRAB domain. In some cases, the dCas9 fused to a KRAB domain is at least about 90%, 95%, or 99% identical, or identical, to SEQ ID NO:3.

In some embodiments, the dCas9 is a transcriptional repressor and comprises a dCas9 domain and a transcriptional repressor domain. In some cases, the dCas9 domain is fused to a chromoshadow repressor domain. SEQ ID NO:12 is an exemplary dCas9 domain fused to a chromoshadow domain. In some cases, the dCas9 fused to a chromoshadow domain is at least about 90%, 95%, or 99% identical, or identical, to SEQ ID NO:12.

In some embodiments, the dCas9 transcriptional modulator is a dCas9 domain fused to an epitope fusion polypeptide. The epitope fusion polypeptide can contain one or more copies (e.g., 2, 3, 4, 5, 6, 7, 8, 9, 10, 11, 12, 13, 14, 15, 16, 17, 18, 19, 20 or more copies) of an epitope. In some cases, the epitope fusion polypeptide contains multiple copies of an epitope separated by one or more linker sequences. In some cases, the linker is configured to allow the binding of affinity agents to adjacent epitopes without, or without substantial, steric hindrance. In some cases, the linker sequences are configured to provide an unstructured or linear region of the polypeptide. For example, the linker sequence can comprise one or more glycines and/or serines. The linker sequences can be at least about 2, 3, 4, 5, 6, 7, 8, 9, 10 or more amino acids in length. In some cases, the linker sequences are, or comprise, one or more of the linkers disclosed on the world wide web at parts.igem.org/Protein_domains/Linker.

The amino acid sequence of the epitope can be any sequence that is specifically recognized by a corresponding affinity agent. Thus, the dCas9 domain fused to the epitope fusion polypeptide will recruit one or more copies of the corresponding fusion agent. This can result in an amplification of any signal or effector function provided by the affinity agent. For example, the affinity agent can be a fusion protein comprising an affinity domain and a transcriptional modulation domain. The dCas9 epitope fusion can form a complex with an sgRNA specific for a target genetic element and recruit multiple copies of the transcriptional modulation domain via the affinity domain to the targeted genetic element.

In some cases, the dCas9 domain fused to an epitope fusion polypeptide contains one or more copies of a GCN4 epitope. In some cases, the epitope fusion polypeptide contains multiple copies of a GCN4 epitope separated by one or more copies of one or more linker sequences. In some cases, the linker is configured to allow the binding of affinity agents to adjacent GCN4 epitopes without, or without substantial, steric hindrance. An exemplary dCas9 fused to a GCN4 epitope fusion domain is or comprises SEQ ID NO:4. In some cases, the dCas9 fused to a GCN4 epitope fusion domain is at least about 90%, 95%, or 99% identical, or identical, to SEQ ID NO:4.

In some embodiments, the epitope fusion polypeptide contains one or more copies of two or more different epitopes. In such cases, the dCas9 can recruit multiple different effector functions. For example, the epitope fusion polypeptide can contain a first epitope that recruits an affinity agent fused to a transcriptional activator. The epitope fusion polypeptide can further contain a second epitope that recruits an affinity agent fused to different effector function. In some cases, the epitope fusion polypeptide containing one or more copies of two or more different epitopes can be used to enhance the specificity of a CRISPR/Cas interaction. For example, one epitope can recruit an affinity agent fused to one half of an obligate dimer effector domain, while the other epitope recruits an affinity agent fused to the other half of the obligate dimer effector domain.

In some cases, the epitope fusion polypeptide recruits one or more copies of an obligate dimer fluorescent protein (e.g., GFP), an obligate dimer recombinase (e.g., CRE recombinase), an obligate dimer luciferase, an obligate dimer thymidine kinase, an obligate dimer TEV protease, or an obligate dimer dihydrofolate reductase (DHFR). In some cases, the epitope fusion polypeptide recruits one or more copies of a combination of effector domains or enzymes which promote or affect transcription. For example, the epitope fusion polypeptide can recruit one or more copies of enzymes or other effector domains that regulate DNA methylation, histone methylation or demethylation, histone deacetylation, RNA polII de-phosphorylation, or promote an increase in nucleosome compaction as measured by reduced DNAse1 hypersensitivity or decreased Micrococcal nuclease accessibility. A combination of activation effector domains or enzymes which could promote transcription could include DNA demethylases, histone demethylases or methylases, histone acetylases, RNA polII phosphorylases, or enzymes or effector domains that reduce nucleosome compaction as measured by increased DNAse1 hypersensitivity or increase micrococcal nuclease accessibility, or promote natural or un-natural chromosomal looping between distal enhancer elements and proximal promoter elements.

Also described herein are expression cassettes and vectors for producing Cas9 or dCas9, including Cas9 or dCas9 fusion proteins, in a host cell. The expression cassettes can contain a promoter (e.g., a heterologous promoter) operably linked to a polynucleotide encoding Cas9 or dCas9. The promoter can be inducible or constitutive. The promoter can be tissue specific. In some cases, the promoter is a weak mammalian promoter as compared to the human elongation factor 1 promoter (EF1A). In some cases, the weak mammalian promoter is a ubiquitin C promoter, a vav promoter, or a phosphoglycerate kinase 1 promoter (PGK). In some cases, the weak mammalian promoter is a TetOn promoter in the absence of an inducer. In some cases, when a TetOn promoter is utilized, the host cell is also contacted with a tetracycline transactivator.

In some embodiments, the strength of the dCas9 or Cas9 promoter is selected to express an amount of Cas9 or dCas9 (e.g., Cas9 or dCas9 epitope fusion protein) that is proportional to the amount of sgRNA or amount of sgRNA expression. In some embodiments, the strength of the selected sgRNA promoter is selected to express an amount of small guide RNA that is proportional to the amount of corresponding affinity agent or the amount of Cas9 or dCas9 (e.g., Cas9 or dCas9 epitope fusion protein). For example, if a dCas9 epitope fusion protein contains ten copies of an epitope, then the dCas9 promoter can be selected to express $1/10^{th}$ the amount of dCas9 as compared to corresponding affinity agent (or less). In some cases, a weak promoter can be selected to reduce cytotoxicity induced by expression of the Cas9 or dCas9 gene.

In some cases, the polynucleotide encoding a small guide RNA-mediated nuclease of the expression cassette further encodes one or two localization sequences (e.g., nuclear localization sequences). For example, the polynucleotide can encode a Cas9 or dCas9 protein having a nuclear localization sequence at the N- and/or C-terminus. The expression cassette can be in a vector, such as a plasmid, a viral vector, a lentiviral vector, etc. In some cases, the expression cassette is in a host cell. The expression cassette can be episomal or integrated in the host cell.

C. Affinity Agents

Described herein are affinity agents for recruiting effector functions to dCas9 epitope fusion proteins. A wide variety of affinity agents can be utilized. Generally, the affinity agent is stable under the reducing conditions present in the intracellular environment of the cell. Additionally, the affinity agent should specifically bind to its corresponding epitope with minimal cross-reactivity. In some cases, the affinity agent is an antibody, such as an scFv. In some cases, the affinity agent is an antibody (e.g., scFv) that has been optimized for stability in the intracellular environment. For example, the affinity agent (e.g., scFv) can be an intrabody (see, e.g., Lo et al., Handb. Exp. Pharm. 2008; (181):343-

73). An exemplary affinity agent comprises the anti-GCN4 scFv domain of SEQ ID NO:5.

The affinity agent can contain one or more solubility enhancing domains. For example, the affinity agent can be fused at the N- and/or C-terminus to a highly soluble, and/or a highly stable, polypeptide. Exemplary solubility enhancing domains include, without limitation, superfolder GFP (Pedelacq et al., Nat Biotechnol. 2006 January; 24(1):79-88), maltose binding protein, albumin, hen egg white lysozyme, glutathione S-transferase, the protein G B1 domain, protein D, the Z domain of protein A, thioredoxin, bacterioferritin, DhaA, HaloTag, and GrpE.

In some embodiments, the affinity agent comprises a transcriptional modulator domain. For example, the affinity agent can contain an affinity domain (e.g., an scFv domain) and a transcriptional modulator (e.g., transcriptional activator or repressor) domain. In some cases, the affinity agent contains an affinity domain fused to one or more copies of a VP8, VP16, or VP64 domain. In some cases, the affinity agent contains an anti-GCN4 affinitydomain fused to one or more copies of a VP8, VP16, or VP64 domain. An exemplary affinity agent containing a transcriptional modulator domain comprises SEQ ID NO:13.

Also described herein are expression cassettes and vectors for producing one or more affinity agents described herein in a host cell. The expression cassettes can contain a promoter (e.g., a heterologous promoter) operably linked to a polynucleotide encoding an affinity agent. The promoter can be inducible or constitutive. The promoter can be tissue specific. In some cases, the promoter is a strong promoter. For example, the promoter can be a CMV promoter, an SFFV long terminal repeat promoter, or the human elongation factor 1 promoter (EF1A). In some cases, the polynucleotide encoding an affinity agent of the expression cassette further encodes one or two nuclear localization sequences. For example, the polynucleotide can encode an affinity agent having a nuclear localization sequence at the N- and/or C-terminus. The expression cassette can be in a vector, such as a plasmid, a viral vector, a lentiviral vector, etc. In some cases, the expression cassette is in a host cell. The expression cassette can be episomal or integrated in the host cell.

III. Methods

Described herein are methods of using CRISPR/Cas for modulating transcription of one or more genes or genetic elements. The methods can be used to optimize sgRNAs by testing a pooled library of sgRNAs that target a single gene and selecting those that produce a desired phenotype. The methods can also be used for small, medium, or large scale (e.g., genome-wide) screening of genetic elements that contribute to a selected phenotype. The methods can also be used to identify interacting genes and gene networks. The methods can also be used for identifying targets for therapeutic development or lead compounds.

A. Screening for Genetic Elements that Modulate a Phenotype

Described herein is a method of screening for one or more genetic elements that modulate a phenotype. The method can be performed by contacting a plurality of cells with a library of structurally distinct small guide RNAs (sgRNAs) that target a plurality of genetic elements, such as any of the sgRNA or sgRNA libraries described herein. The contacting the plurality of cells with a plurality of sgRNAs can thereby generate a plurality of test cells, the plurality of test cells each comprising: a small guide RNA (sgRNA); and a nuclease deficient sgRNA-mediated nuclease (dCas9), wherein the dCas9 comprises a dCas9 domain fused to a transcriptional modulator or a dCas9 domain fused to an epitope fusion domain. The method includes selecting the cells on the basis of the phenotype and quantitating the frequency of the structurally distinct sgRNAs within the population of selected cells. sgRNAs that target genetic elements that modulate the phenotype can be overrepresented or underrepresented in the selected cells. In some cases, the cells are also contacted with a plurality (e.g., about 2, 3, 4, 5, 6, 7, 8, 9, 10, 15, 20, 25, 30, 50, 75, 100, 150, 200, 250, 300, 350, 400, 500, 750, 1000 or more) of control sgRNAs. For example, the control sgRNAs can have binding regions that do not bind to any genomic region or transcript. Alternatively, the control sgRNAs can bind to a genomic region that is known to not produce or affect the phenotype of interest. As yet another alternative the control sgRNAs can affect an alternate control phenotype.

The phenotype can be cell growth, survival, or proliferation. In some cases, the phenotype is cell growth, survival, or proliferation in the presence of an agent, such as a cytotoxic agent, an oncogene, a tumor suppressor, a transcription factor, a kinase (e.g., a receptor tyrosine kinase), a gene (e.g., an exogenous gene) under the control of a promoter (e.g., a heterologous promoter), a checkpoint gene or cell cycle regulator, a growth factor, a hormone, a DNA damaging agent, a drug, or a chemotherapeutic.

For example, test cells containing sgRNAs and dCas9 can be cultured in the presence of a growth factor such as epidermal growth factor. The cells can be harvested after a sufficient period of culturing. sgRNAs, or polynucleotides encoding the sgRNAs, can be extracted from the cells and quantified by, e.g., sequencing. The frequency of sgRNAs can be thereby determined. sgRNAs that increase cell growth, proliferation, viability, or survival in the presence of epidermal growth factor can thereby be identified as those that are overrepresented. sgRNAs that decrease growth, proliferation, viability, or survival of cells in the presence of epidermal growth factor can thereby be identified as those that are underrepresented. Overrepresentation and underrepresentation can be relative to their frequency in the library that was contacted with the cells, relative to the frequency of the sgRNAs in the cells (or a sub-population of the cells) prior to selection (or early in the selection period), or relative to a frequency in control cells that are not subject to the selection or subject to an alternative selection. The target genetic elements of such overrepresented or underrepresented sgRNAs can thereby be identified as genetic elements that modulate the phenotype.

The phenotype can also be protein expression, RNA expression, protein activity, or cell motility, migration, or invasiveness. For example, a plurality of cells that express a particular cell surface protein associated with tumor malignancy can be contacted with a plurality of sgRNAs and dCas9 transcriptional modulators (activators and/or repressors). The cells can be incubated for a sufficient time to allow sgRNA:dCas9 complex formation and transcriptional modulation. The cells can then be contacted with an antibody that recognizes the malignancy associated cell surface protein. The antibody can be used to select cells, or select against cells, that express the cell surface protein, for example by fluorescence activated cell sorting or using solid phase purification (e.g., with protein A agarose). sgRNAs that are overrepresented or underrepresented in the selected cells can be identified as altering cell surface expression of the malignancy associated protein. As another example, cell motility, migration, or invasiveness can be selected using a boyden chamber using methods known in the art.

The frequency of sgRNAs in test and/or control cells that are quantitated in various methods described herein can be determined in a variety of ways. In one embodiment, sgRNAs are quantitated by deep sequencing. As used herein, "deep sequencing" refers to highly redundant sequencing of a nucleic acid or a family of nucleic acids, such as a family of sgRNAs or a family of polynucleotides encoding sgRNAs. The redundancy (i.e., depth) of the sequencing is determined by the length of the sequence to be determined (X), the number of sequencing reads (N), and the average read length (L). The redundancy is then N×L/X. In the case of sgRNAs, the length of the sequence can be the length of the binding region, the full length of the sgRNA, or the length of a portion of the sgRNA that contains the binding region. The sequencing depth can be, or be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 150, 200, 300, 500, 500, 700, 1000, 2000, 3000, 4000, 5000 or more. Deep sequencing can provide an accurate number of the relative frequency of the sgRNAs. Deep sequencing can also provide a high confidence that even sgRNAs that are rarely present in a population of cells (e.g., a population of selected test cells) can be identified.

In some embodiments, the screen is an interference screen. In some cases, if the screen is an interference screen, the plurality of cells can be contacted with a library of sgRNAs, wherein a majority, substantial majority, or at least 90% (e.g., at least 90, 95, or 99%) of the sgRNAs are targeted at the TSS start site of a gene, or upstream (5') of the TSS of a gene. In some cases a majority, substantial majority, or at least 90% (e.g., at least 90, 95, or 99%) of the sgRNAs are targeted to a region between, or between about, 0 and about 750 bp upstream of the TSS of a gene.

If the screen is an interference screen, the plurality of cells can be contacted with a dCas9 containing a dCas9 domain. Binding of a dCas9 domain in complex with an sgRNA can interfere with transcription at or near the genetic element targeted by (bound to) the sgRNA:dCas9 complex. Without wishing to be bound to theory, it is believed that the sgRNA:dCas9 complex can compete with RNA polymerase or other transcriptional machinery to suppress transcription at or near the targeted genetic element.

Alternatively, if the screen is an interference screen, the plurality of cells can be contacted with a dCas9 containing a dCas9 domain fused to one or more copies of a transcriptional repressor. Exemplary transcriptional repressors include, without limitation, a KRAB domain, a chromoshadow domain, a SID domain, or an EAR-repression domain (SRDX). The transcriptional repressor can be codon optimized for efficient expression in the host cell.

As yet another alternative, if the screen is an interference screen, the plurality of cells can be contacted with a dCas9 containing a dCas9 domain fused to an epitope fusion domain. In such cases, the plurality of cells can also be contacted with an affinity agent having affinity for the epitope of the epitope fusion protein. The affinity agent can contain an affinity domain (e.g., an scFv) or an affinity domain fused to a transcriptional repressor. Binding of the sgRNA:dCas9 complex to a targeted genetic element can then recruit one or more copies of the affinity agent to the site of the targeted genetic element. In cases where the affinity agent is not fused to a transcriptional repressor, the enhanced size of the sgRNA:dCas9:affinity agent complex can further suppress expression at or near the targeted genetic element relative to a complex of sgRNA and a dCas9 domain. In cases, where the affinity agent is fused to a transcriptional repressor, the recruitment of multiple copies of the transcriptional repressor can further suppress expression at or near the targeted genetic element relative to the previously described transcriptional repressors.

In some embodiments, the screen is an activation screen. In such cases, the plurality of cells can be contacted with a library of sgRNAs, wherein a majority, substantial majority, or at least 90% (e.g., at least 90, 95, or 99%) of the sgRNAs are targeted at the TSS start site of a gene, or downstream (3') of the TSS of a gene. In some cases a majority, substantial majority, or at least 90% (e.g., at least 90, 95, or 99%) of the sgRNAs are targeted to a region between, or between about, 0 and about 1000 bp downstream of the TSS of a gene.

In some cases, wherein the screen is an activation screen, the plurality of cells can be contacted with a dCas9 containing a dCas9 domain fused to one or more copies of a transcriptional activator. Exemplary transcriptional repressors include, without limitation, a p65 activation domain (p65AD), or one or more copies of a VP8, VP16, or VP64 domain. The transcriptional repressor can be codon optimized for efficient expression in the host cell.

As yet another alternative, the plurality of cells can be contacted with a dCas9 containing a dCas9 domain fused to an epitope fusion domain. In such cases, the plurality of cells can also be contacted with an affinity agent having affinity for the epitope of the epitope fusion protein. The affinity agent can contain an affinity domain fused to a transcriptional activator, such as any of the activators described herein. Binding of the sgRNA:dCas9 complex to a targeted genetic element can then recruit one or more copies of the affinity agent to the site of the targeted genetic element. The recruitment of multiple copies of the affinity agent and thus multiple copies of the transcriptional activator can further activate expression at or near the targeted genetic element relative to activation provided by a dCas9 fused to a transcriptional activator.

In some embodiments, an activation and an interference screen can be performed at the same time. For example, a plurality of cells can be contacted with an sgRNA library. The plurality of cells can further be contacted with both dCas9 interference modulators and dCas9 transcriptional activation modulators. For example, dCas9 interference can be provided by a dCas9 domain, a dCas9 domain fused to a transcriptional repressor, or a dCas9 fused to an epitope fusion protein and an affinity agent fused to a transcriptional repressor. As another example, the interference can be provided by a Cas9 nuclease that cleaves or knicks target nucleic acid.

As yet another example, dCas9 activation can be provided by a dCas9 domain fused to a transcriptional activator, or a dCas9 fused to an epitope fusion protein and an affinity agent fused to a transcriptional activator. In some cases, a portion of the plurality of cells can contain a dCas9 transcriptional activator and a portion can contain a transcriptional repressor. Thus, sgRNAs that complex with an activator can activate targeted genetic elements and sgRNAs that complex with a repressor can repress targeted genetic elements.

As yet another example, the plurality of cells can be contacted with a library of sgRNAs and a library of shRNAs and a dCas9 transcriptional activator. The dCas9 transcriptional activator can be a dCas9 domain fused to transcriptional activator or a dCas9 fused to an epitope fusion domain that is bound to one or more copies of an affinity agent fused to a transcriptional activator. Thus, the shRNAs repress target genetic elements and the sgRNAs activate target genetic elements.

sgRNAs and/or shRNAs that target genetic elements that modulate a phenotype can then be identified as described herein. For example, sgRNAs and/or shRNAs that are overrepresented or underrepresented in selected cells can be identified. In some cases, the method can further include associating whether the overrepresented or overrepresented sgRNAs are in cells providing dCas9 interference or dCas9 activation.

B. Identifying Druggable Targets and Lead or Therapeutic Compounds

Described herein are methods of identifying targets for drug development or identifying lead compounds. As an example, methods described herein can be used to identify target genes or genetic elements whose transcriptional modulation produces a desired phenotype. The identified target can then serve as a target for lead compound identification, screening, or development.

In some embodiments, the method includes performing an sgRNA screen, such as any of the sgRNA screens described herein, on a plurality of cells using a library of sgRNAs, such as any of the sgRNAs or libraries described herein to identify a gene or genetic element that modulates a phenotype. For example, the phenotype can be a growth, proliferation, survival, or viability of a tumor cell. In some cases, the screen can identify genetic elements whose transcriptional modulation affects growth, proliferation, survival, or viability of the tumor cell. In some cases, the genetic elements encode or regulate protein targets, or portions thereof, for which pharmaceutical inhibitors or activators are known. In some cases, activators or inhibitors are known, but they are not suitable therapeutic pharmaceutical agents. In such cases, the activators or inhibitors can serve as lead compounds for further development of therapeutic pharmaceutical agents.

In some cases, the genetic elements encode or regulate protein targets, or portions thereof for which activators or inhibitors are as yet unidentified. Nevertheless, the identification of the genetic elements can allow development of screening methods for identification or development of lead compounds and/or pharmaceutical agents. For example, the genetic element, or a genomic region containing the genetic element can be operably linked to a reporter gene. The activity of the reporter gene can be assayed in the presence of a large number of different candidate compounds to identify a lead compound.

C. Identifying Interacting Genetic Elements

Identification of genetic interactions (GI) between pairwise sets of genetic elements, have enabled the systematic exploration of gene function in various organisms. Described herein, are methods for performing large scale and unbiased screens for pairwise genetic interactions using sgRNAs. For example, a plurality of sgRNAs can be contacted with a plurality of cells to identify high-confidence target genetic elements for a given phenotype and effective sgRNAs. Double-sgRNA libraries can be constructed from this list of high-confidence target genetic elements to systematically measure GIs between hits.

In some cases, the plurality of sgRNAs can be selected or designed to target each gene, genetic element, or genomic region with multiple sgRNAs (e.g., about, or at least about, 2, 3, 4, 5, 6, 7, 8, 9, 10, 11, 12, 13, 14, 15, 16, 17, 18, 19, 20, 21, 22, 23, 24, or 25 sgRNAs per targeted gene, genomic region, or genetic element). Such highly complex libraries increase the likelihood of targeting each gene with several effective sgRNAs, thus reducing the false-negative rate. Additionally, requiring several effective sgRNAs to identify a hit gene reduces the rate of false-positives, since it is unlikely that several sgRNAs targeting a non-hit gene have off-target effects relevant to the phenotype of interest.

Therefore, in some cases, the plurality of sgRNAs can be selected or designed to target each gene, genetic element, or genomic region with a minimal number of effective sgRNAs (e.g., about, or at less than about, 25, 24, 23, 22, 21, 20, 19, 18, 17, 16, 15, 14, 13, 12, 11, 10, 9, 8, 7, 6, or 5 sgRNAs per targeted gene, genomic region, or genetic element). Such minimally complex libraries can be advantageous for enabling large scale and efficient screening. For example, if 100 sgRNAs per targeted gene is required for high confidence screening, a library must be 10-fold larger than a library that requires only 10 sgRNAs per targeted gene for high confidence screening.

The ability to rapidly generate GI maps can identify previously unrecognized gene functions and inform the design of combination therapies based on synergistic pairs. For example, pairs of genes that exhibit synthetic lethality in cancer cells, but not healthy cells, are ideal targets for combination therapies aimed at limiting the emergence of drug resistance in rapidly evolving cells. As another example, if a first and a second gene form an unexpected synergistic genetic interaction for an undesirable phenotype (e.g., tumor growth), then a combination therapy that inhibits both targets can be designed.

In some embodiments, each sgRNA of a pair in a double sgRNA screen is expected to contribute additively to a phenotype of interest in the absence of genetic interaction. Thus, for example, if a single first sgRNA is underrepresented on average by 50% after selection for a phenotype of interest and a single second sgRNA is overrepresented on average by 50% after selection for a phenotype of interest, then a non-interacting pair would be expected to lack significant overrepresentation or underrepresentation. Thus, interacting genes, genomic regions, or genetic elements are identified as corresponding to those sgRNA pairs that are present after a selection event as pairwise combinations that deviate in frequency from the additive relationship expected from the frequency determined in the initial individual sgRNA screen.

D. Identifying Rules for Optimal Targeting of Genetic Elements with CRISPR/Cas

Described herein are methods of assaying sgRNAs for targeting efficiency (e.g., cutting, nicking, interfering, or activating). These assays can be used to develop or discover rules for optimal or optimized sgRNA design. In some embodiments, a library or pool of sgRNAs that target a single gene, genomic region, or genetic element can be generated. The library can be utilized to test which sgRNAs produce a desired phenotype and/or have the highest targeting efficiency. The sequence of the sgRNA (e.g., the sequence of the binding region) and information about the targeted genetic element can then be combined to discover sgRNA design rules. In some cases, the pool of sgRNAs can be designed to contain sgRNAs with mismatched base pairs for use as controls or to determine the effect of mismatches on sgRNA targeting efficiency.

In some cases, the target gene is a reporter gene (e.g., encoding a fluorescent protein, a luciferase, or a gene that confers resistance to a selection agent). In some cases, the reporter gene is present on a plasmid. In other cases, the reporter gene is integrated into the genome of a host cell. In some cases, assaying sgRNA targeting efficiency against an endogenous or heterologous gene that is in the genome of a host cell can allow for analysis or discovery of genomic context specific rules for sgRNA targeting. For example, rules for optimal chromatin conformation or enhancer site positioning can be examined. In some cases, assaying sgRNA targeting efficiency against an episomal or plasmid-based gene can allow for robust signal generation to examine subtle variations in targeting efficiency.

IV. Kits

Described herein are kits for performing sgRNA transcriptional modulation. The kits can be used for performing sgRNA screens as described herein. In one embodiment, the kit contains an sgRNA scaffold and a polynucleotide encoding a Cas9 or dCas9 (e.g., an activating or repressing dCas9). In another embodiment, the kit contains a library of polynucleotides encoding structurally distinct sgRNAs and a polynucleotide encoding a Cas9 or dCas9. In some cases, the kit contains a polynucleotide encoding a dCas9 activator and a dCas9 repressor. In some cases, the kit contains a polynucleotide encoding an affinity agent, such as an affinity agent having affinity for an epitope fused to a dCas9 domain. In some cases, affinity agent having affinity for an epitope fused to a dCas9 domain is fused to a transcriptional activator or repressor. In some cases, the polynucleotides (e.g., polynucleotides encoding sgRNAs, or sgRNA-mediated nucleases) are in expression cassettes and operably linked to a promoter. In some cases, the expression cassettes are in suitable vectors. In some cases, one or more of the vectors or expression cassettes are in a host cell.

In some cases, the kit contains a plurality of host cells, each cell containing an expression cassette encoding a Cas9 or dCas9, and optionally an expression cassette encoding an affinity agent. The kit can further contain an sgRNA scaffold. The kit can be used to clone a library of sgRNA binding regions (e.g., binding regions complementary to) into the sgRNA scaffold and transform the plurality of host cells. The host cells can be selected on the basis of a phenotype of interest and thereby perform any of the sgRNA screens described herein.

All patents, patent applications, and other publications, including GenBank Accession Numbers, cited in this application are incorporated by reference in the entirety for all purposes.

EXAMPLES

The following examples are provided by way of illustration only and not by way of limitation. Those of skill in the art will readily recognize a variety of non-critical parameters that could be changed or modified to yield essentially the same or similar results.

Example 1: Modular sgRNAs

A BlpI site was introduced into the 5' hairpin region of an sgRNA scaffold. A library of sgRNA binding regions was synthesized using solid phase synthesis techniques. The binding regions have a 3' end that can be ligated to a cut BlpI site. The sgRNA scaffold was cut with BlpI and purified. Synthesized binding regions were recovered and ligated to the cut sgRNA scaffold to produce a library of sgRNAs.

Example 2: Inducible CRISPRi System

An inducible CRISPRi system was constructed that enables dynamic control of gene expression. This optimized set of fusion proteins positions a transcriptional repressor effector domain (KRAB) to the N-terminus using an optimized linker domain and removes the fluorescent tag from dCas9 via a self-cleaving peptide. The optimized CRISPRi system shows a 4-15 fold improved activity on a GFP reporter. The CRISPRi system involves delivery of 3 genes or gene products (e.g., an optimized sgRNA, a tet-transactivator, and a tet inducible dCas9-repressor construct).

Example 3: Inducible System for Multimerization of Effector Domains at DNA with CRISPR An inducible Cas9 system for controllable multimerization of effector domains at DNA is constructed. This system involves the delivery of 4 genes or gene products (e.g., an optimized sgRNA, a tet-transactivator, and the tet inducible dCas9-GCN4 epitope fusion protein, and a recombinant single chain variable chain fragment antibody which binds to the GCN4 epitope fused to sfGFP and VP64 (scFVVP64)).

Activation can be tuned to a desired level by varying the number of GCN4 epitopes in the dCas9-GCN4 fusion protein. Fusion proteins with 6, 10 or 24 epitope copies (antibody binding sites) are constructed. The ratio of dCas9 protein to scFVVP64 can also be tuned, e.g., by appropriate promoter and inducer selection. The concentration of antibody and effector protein should typically exceed the concentration of the dCas9 fusion protein by the number of epitope binding sites on the dCas9 fusion. For example a construct that expresses at least 10 fold more scFV-VP64 than dCas9-10×GCN4 can in theory saturate each dCas9-10×GCN4 fusion protein with antibody delivered effector domains. This inducible dCas9 fusion system can be expressed in the absence of doxycycline to achieve sufficiently low dCas9 fusion protein levels.

Stability of intracellular antibodies (e.g., macroaggregation or microaggregation) in the presence and/or absence of dCas9 can also be optimized. An antibody fusion with optimized solubility and stability is obtain by selecting cell clones using a discrimination function with defined rules for the proper levels and localization of the antibody. Too much antibody expression or too little antibody expression can result in a nonfunctional multimerization system.

To optimize a working multimerization system single cell flow cytometry data is utilized to screen for a number of candidate constructs for proper expression level, stability, and activity. Test genes such as CXCR4 which is off in K562 cells are assayed for activation in a population of cells with different dCas9GCN4 fusion proteins and different scFV antibodies. Both median and mean activation of transcription is measured to determine optimal expression levels of sgRNA:dCas9:affinity agent components to optimally activate transcription in all cells. 50-fold induction in protein of genes which are completely off such as CXCR4 in K562 cells is achieved. The activation is unimodal with only ~2% of cells showing weak or no activation.

Example 4: Establishing Rules for sgRNA Targeting

A complex pool of ~55,000 sgRNAs targeting 10 kb around the transcription start sites of 50 genes known to influence resistance/sensitivity to the toxin ricin was constructed. This pool (or "library") included every possible sgRNA between 19 and 25 bp long, starting with a G (for efficient transcription) and having a binding region (and thus corresponding target sequence ending immediately before an NGG (a protospacer adjacent motif for *Streptococcus pyogenes* Cas9). sgRNAs expected to have significant off-target binding sites elsewhere in the genome were filtered out. This was done by establishing a scoring metric as follows: PAM G1=40; PAM G2=19; PAM N=0; Region I=28; Region II=19; Region III=10. Offtarget binding at any given site can be estimated as: 1−sum (mismatches*mismatch_score)/40. For inclusion in this library, no mismatch was greater than 0. The library also included approximately 1000 sgRNAs designed against scrambled target sequences that were estimated to have no binding site anywhere in the genome as negative controls.

The library was tested in K562 cells expressing dCas9, dCas9-Krap, dCas9-VP64, and nuclease active Cas9, driven by both constitutive and tretacycline inducible promoters, and screening for ricin sensitivity as described (Bassik et al., Cell. Feb. 14, 2013; 152(4): 909-922; Kampmann et al., Proc Natl Acad Sci USA. Jun. 18, 2013; 110(25): E2317-E2326).

These tests established rules for selecting sgRNAs that are critical for KRAB-mediated repression and VP64-mediated activation screening, as described herein. By searching for the optimal window for dCas9-Krab mediated repression, a window of 50 bp upstream of the transcription start site (TSS) to 300 bp downstream was determined as most effective and a window of 50-400 bp upstream of the TSS was determined most effective for dCas9 mediated activation.

The length of sgRNA binding regions was tested and shorter guides of 19-21 bp are determined to be more effective than longer guides.

Ensemble transcripts annotated by the APPRIS pipeline were determined as most likely to exhibit a phenotype.

sgRNAs containing binding regions having four or more consecutive nucleotides were found to be generally deleterious, with putative PolIII terminator poly-U the worst and poly-C the least.

Guide strength (plotted as Z-score) is generally consistent across a range of GC percent (x-axis), but extremely high or low values were determined to be worse on average.

Overlapping, or nearly overlapping, sgRNAs (0-0 and 1-4 bp apart) were enriched for phenotypes that have little or no difference, suggesting libraries should be designed to enforce at least 5 bp separation between sgRNA target sequences.

sgRNAs that target sequences with a low MNase-seq signal correlated with stronger average guide Z-scores, indicating that sgRNAs should be targeted to genetic elements with a low MNase seq signal.

A strong agreement between ENCODE published PolII ChIP-seq signal and CRISPRi phenotype was observed, suggesting that CRISPRi sgRNAs should be targeted to regions where PolII ChIP-seq signal is high. Similarly, as much of PolII signal at the TSS is not associated with productive transcription, filtering where PolII is most active with published Global Run-on Sequencing (GRO-seq) data further refined sgRNA targeting rules. Applying a threshold for guide length along with MNase, PolII, and GRO-seq signals, each alone or in combination, improved the median Z-score of guides by up to 10-fold.

Example 5: Utilizing Established sgRNA Selection Rules in a Support Vector Machine The rules established in Example 4 were used to train a support vector regression machine (SVR) to predict the most active guides for every gene in the genome of a target cell. Guide positioning, length, PolII signal, and MNase signal were used to train the SVR on 25% of the data. The SVM was cross-validated by leaving out each gene and testing the ability of the machine to predict the sgRNA activity for that gene based on the other genes in the training set. Selecting 25 top guides per gene predicted by the SVR versus 24 shRNAs gave stronger p-values in almost every case for CRISPRi and CRISPRa.

Example 5: CRISPRa Protein Multimerization

Cells were contacted with an sgRNA, a dCas9-10× epitope fusion, and an scFv-VP64 fusion with affinity to the epitope. K562 cells contacted with dCas9-GCN4-10× and scFv-sfGFP-VP64 and 1, 2, or 3 different sgRNAs targeting the CXCR4 locus show strong induction of CXCR4 activation. Cells contacted with dCas9-VP64 fusion are and 1, 2, or 3 different sgRNAs targeting the CXCR4 locus show moderate CXCR4 activation. K562 cells contacted with 3 different sgRNAs targeting the CXCR4 locus and scFv-sfGFP-VP64 exhibit strong cell surface expression of CXCR4 as demonstrated by flow cytometry. Cells contacted with dCas9-VP64 fusion are and 3, 2, or 1 different sgRNAs targeting the CXCR4 locus and scFv-sfGFP-VP64 show increasing levels of cellular migration.

Example 6

I. Abstract

While the catalog of mammalian transcripts and their expression levels in different cell types and disease states is rapidly expanding, our understanding of their function lags far behind. Presented herein is a robust technology enabling systematic investigation of the cellular consequences of repressing or inducing any transcript. Rules for efficient and specific targeting of transcriptional repressors (CRISPRi) or activators (CRISPRa) to endogenous genes via endonuclease-deficient Cas9, enabling modulation of expression over a ~1000-fold range were identified. Using these rules, construct a genome-scale CRISPRi library was constructed and validated with two pooled screens. A growth-based screen robustly identified essential gene sets. A screen for sensitivity to a cholera-diptheria fusion toxin provided broad insights into the molecular mechanisms of toxin entry, retro-translocation and toxicity. Importantly, CRISPRi has minimal off-target effects, robustly represses transcription (typically achieving 90-99%), and is non-toxic and reversible. Together, CRISPRi and CRISPRa represent key tools for defining gene function in metazoans.

II. Introduction

Dramatic advances in sequencing technology have catalogued a universe of RNA transcripts—greatly exceeding the number of canonical protein-coding open reading frames (ORFs)—which collectively are responsible for carrying out the instruction encoded in the genome (Pubmed IDs: 22955620, 24670764, 20220758, 24037378, 19812545). A central challenge now is to understand the biological role of these transcripts and how quantitative differences in their expression define cellular states in normal development and in disease. Despite intense efforts, the function of many protein-coding genes remains poorly defined, and even less is known about the biological roles of most non-canonical transcripts such as enhancer RNAs, upstream antisense RNAs, lncRNAs, or other intergenic RNAs (Pubmed IDs: 24679528, 24267885). Efforts to address this deficiency in our knowledge would be greatly aided by techniques that are capable of dynamically and precisely controlling the expression of individual transcripts.

One way to explore gene function is to disrupt transcript expression through deletion or repression. However, the dominant tool for programmed knockdown of mRNAs, RNA-interference (RNAi), has pervasive problems with off-target effects, which can be especially confounding in the context of large-scale screens (Pubmed IDs: 23394947, 16929316, 15042091, 15960972, 17572676, 19012953, 12754523, 22344029). Additionally, because RNAi is mediated by cytoplasmic argounaute proteins, gene silencing through this approach is best suited to depletion of cytosolic mRNA targets.

An alternative emerging strategy is programmable genome editing methods that permanently delete or modify DNA using designable, sequence-specific endonucleases such as zinc finger, TALEN or CRISPR (clustered regularly interspaced short palindromic repeats)/Cas9 (CRISPR-associated protein 9) proteins (Pubmed IDs: 20717154, 20660643, 21179091, 22745249, 23386978, 23287718, 23287722, 23360966, 23360964, 23360965, 23643243). A series of elegant studies recently exploited the readily programmable nature of Cas9, in which the specificity is determined by a short guide (sg)RNA, to enable genome-wide loss of function screens (Pubmed IDs: 24336569, 24336571, 24535568, 24717434). These established CRISPR cutting as a powerful screening technology complementary to RNAi (especially when full knockouts are needed to see phenotypes) or haploid mutagenesis screens (Pubmed IDs: 19965467). Nonetheless, screening approaches based on genome editing are currently focused on loss-of-function studies involving irreversible frameshift disruptions, limiting their utility for the study of essential genes and noncoding RNAs. Additionally, double-stranded DNA breaks can be cytotoxic (Pubmed IDs: 24584192, 12016139, 11048728. 8643488). Finally, indel formation from error-prone DNA repair often leads to variable, short in-frame deletions or insertions, limiting the ability to reliably disable all of the alleles of a gene.

A programmable DNA binding protein that can recruit an effector domain to turn on and off transcription in a dynamic and quantitative manner offers, in principle, a more flexible tool for interrogating the many transcripts in complex genomes. Pioneering experiments with designed chimeric zinc finger and TALE proteins fused to transcription effector domains demonstrate that such an approach can modulate transcription of endogenous genes (Pubmed IDs: 9843940, 10660690, 21248753, 23664777, 23396285, 23377379, 23877069). However, as each transcript target requires a unique fusion protein, expanding these methods to genome-scale is arduous.

Recently, catalytically inactive Cas9 (dCas9) fusion proteins guided by gene specific sgRNAs have been used to localize effector domains to specific DNA sequences to either repress (CRISPRi) or activate (CRISPRa) transcription of target genes (Pubmed IDs: 23452860, 23849981, 24360272, 23979020, 23892898, 23977949, 23892895, 23761437, 23907171). To date, a very small number of sgRNAs have been tested, leaving unanswered whether CRISPRi/a is a feasible strategy for globally interrogating gene function and, if so, how best to target a gene to activate or repress transcription while minimizing off-target effects.

Here, the development and application of a method for high-specificity, genome-wide modulation of transcription of endogenous genes in human cells using CRISPRi/a is described. To accomplish this, a saturating screen was performed in which the activity of every nonredundant sgRNA tiling over 49 kilobases of DNA around the transcription start sites of 49 genes known to modulate cellular susceptibility to ricin was tested. From this, distinct rules for how and where either CRISPRi or CRISPRa maximally changes the expression of endogenous genes in human cells were extracted, as well as rules for predicting off-target effects, providing an algorithm to design a genome-scale library targeting each gene with 10 sgRNAs. This library was validated by first screening for genes essential for cell growth or survival, and in a second experiment screening for genes that govern response to a chimeric cholera/diphtheria fusion toxin (CTx-DTA) (22123862). The former robustly enriches for known categories of essential genes and the latter provides comprehensive insights into the molecular mechanisms of CTx-DTA intoxication. These experiments demonstrate our CRISPRi/a screening platform is robust, showing very high reproducibility and activity with undetectable intrinsic toxicity.

More generally, these experiments establish that CRISPRi/a transcriptional control is inducible, reversible, and can target essential genes. CRISPRi and CRISPRa can be used to control transcript levels for endogenous genes across a high dynamic range (up to ~1000-fold). Extensive evidence is also provided that properly designed CRISPRi/a reagents show exquisite specificity. As such, this method represents a transformative tool for defining transcript function across the breadth of transcripts encoded by the human genome.

III. Results

A. High Throughput-Tiling Screen Defines Rules for CRISPRi Activity at Endogenous Genes CRISPRi can repress transcription by directly blocking RNA polymerase activity (dCas9) or through effector domain-mediated transcriptional silencing (dCas9-KRAB). In order to better understand and optimize CRISPRi activity, a pooled high throughput screen was used to define rules that determine CRISPRi repression of endogenous genes. 49 genes that had previously shown to modulate cellular susceptibility to the AB toxin ricin (Pubmed ID: 23394947) were targeted. The resistance phenotype (protective or sensitizing) for these 49 genes had earlier been catalogued by RNAi mediated knock-down in K562 cells, showing that the amount of gene repression for these genes typically has a monotonic, near-linear relationship with the ricin resistance phenotype. This observation allowed the use of a ricin resistance score calculated by measuring sgRNA frequencies in a pooled screen to measure how much dCas9 or dCas9-KRAB repressed transcription for thousands of sgRNAs.

Using massively parallel oligonucleotide synthesis, a library of sgRNAs was generated that tiled the DNA in a 10-kilobase window around the transcription start site of these 49 genes (54,000 total sgRNAs) (Pubmed ID: 19448642) (FIG. 1A). sgRNAs were predicted to have off-target activity were excluded based on a provisional score that was developed using data from published Cas9 and dCas9 activity at near-consensus DNA binding sites containing mismatches (see below for an empirical measure of specificity) (Pubmed ID: 23873081, 23792628, 23452860). This cutoff filtered out most sgRNAs mapping to repetitive SINE or LINE elements. To determine how sgRNA length impacts CRISPRi function, sgRNAs between 19-25 base pairs in length were included, including overlapping variable length sgRNAs that share the same protospacer adjacent motif (PAM). 1,000 negative control sgRNAs that were picked according to the same principles as targeted sgRNAs, but derived from scrambled pseudo-genome sequences and predicted not to target any sites in the human genome were also included.

Figures 8A, 8B:
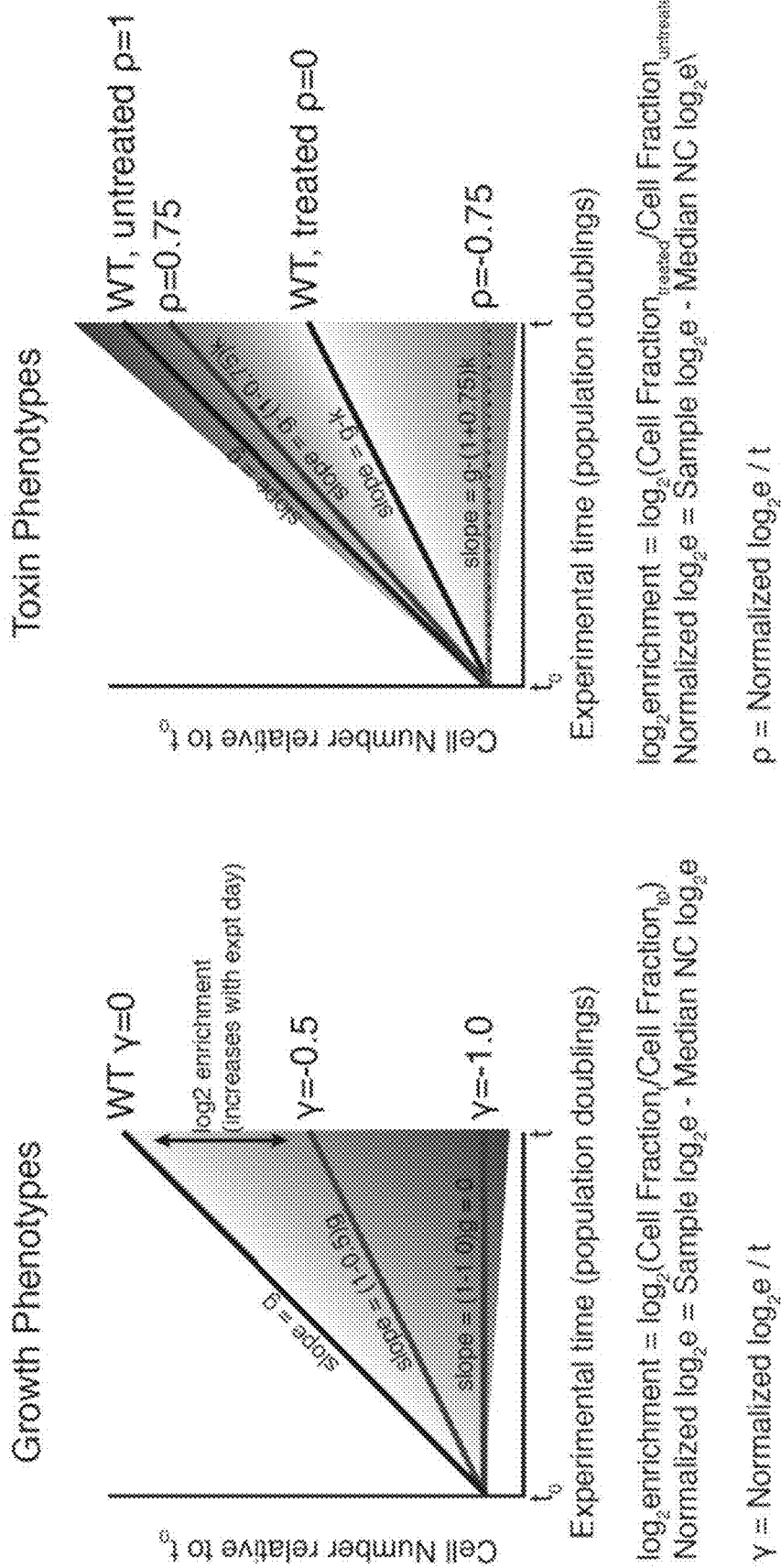
FIG. 8A-FIG. 8C: Mathematical framework for quantifying sgRNA phenotype and activity.

This test library of sgRNAs was packaged into lentiviral particles and used to transduce, K562 human myeloid leukemia cells stably expressing dCas9 or a dCas9-KRAB fusion protein (Pubmed ID: 23849981). To ensure that the majority of cells expressed no more than one sgRNA, the multiplicity of infection to was limited to 0.3. Populations of cells expressing this library of sgRNAs were either harvested at the outset of the experiment, grown under standard conditions, or treated with ricin. Two biological replicates of each screen were performed. The frequency of each sgRNA in the library following growth in each condition was then counted using deep sequencing to determine how each sgRNA in the library modulates cell growth and cellular susceptibility to ricin, phenotypes that were defined quantitatively as gamma and rho, respectively (See FIG. 8A and FIG. 8B and Pubmed ID: 23739767).

Figure 1B:
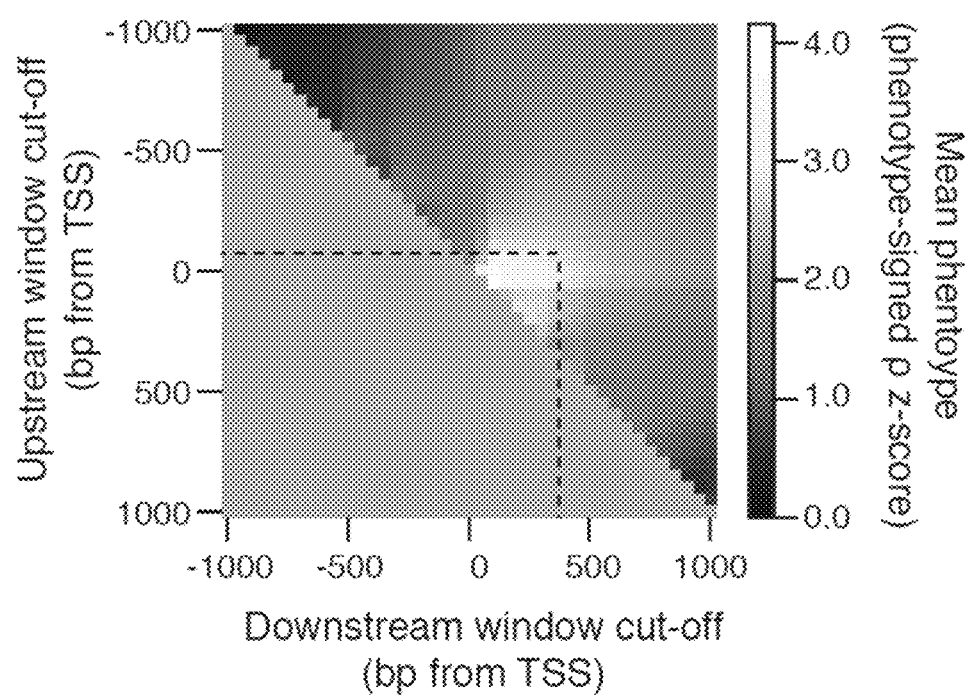
Figure 1C:
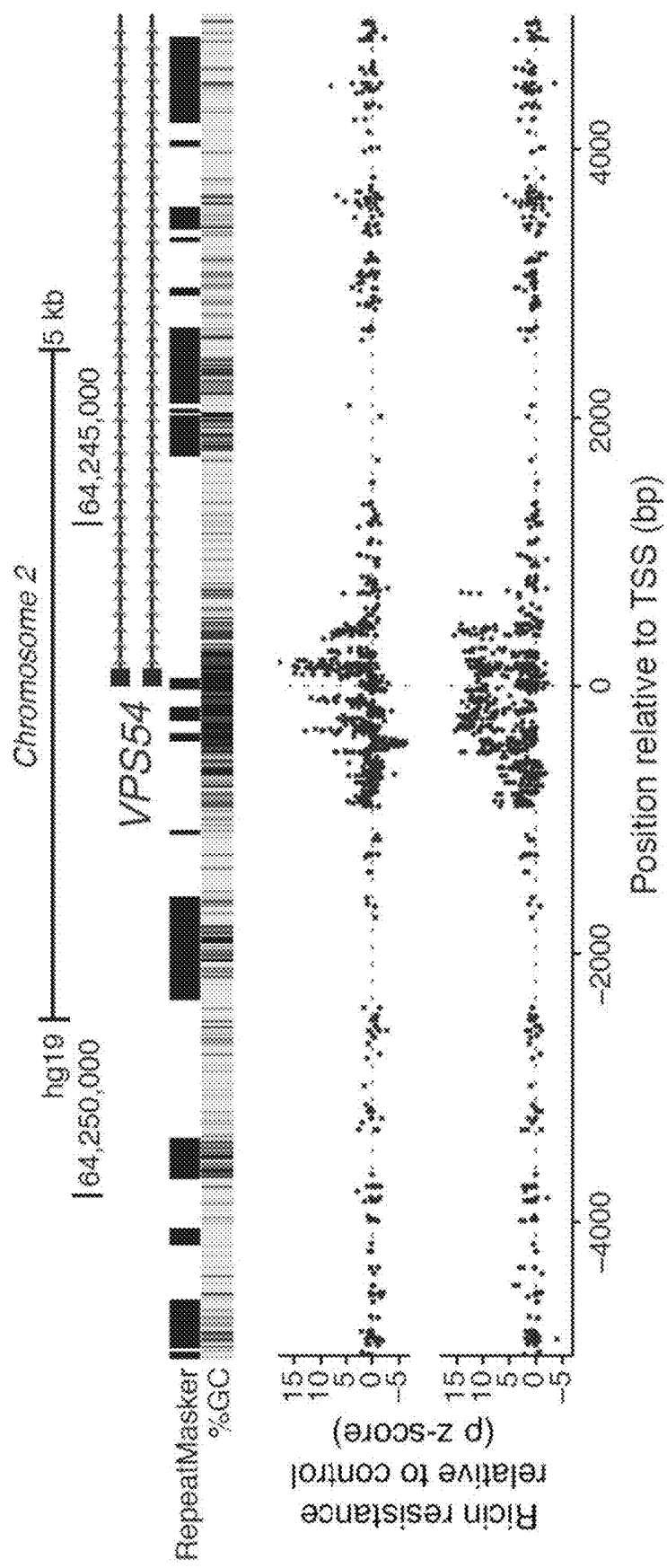
Figure 1D:
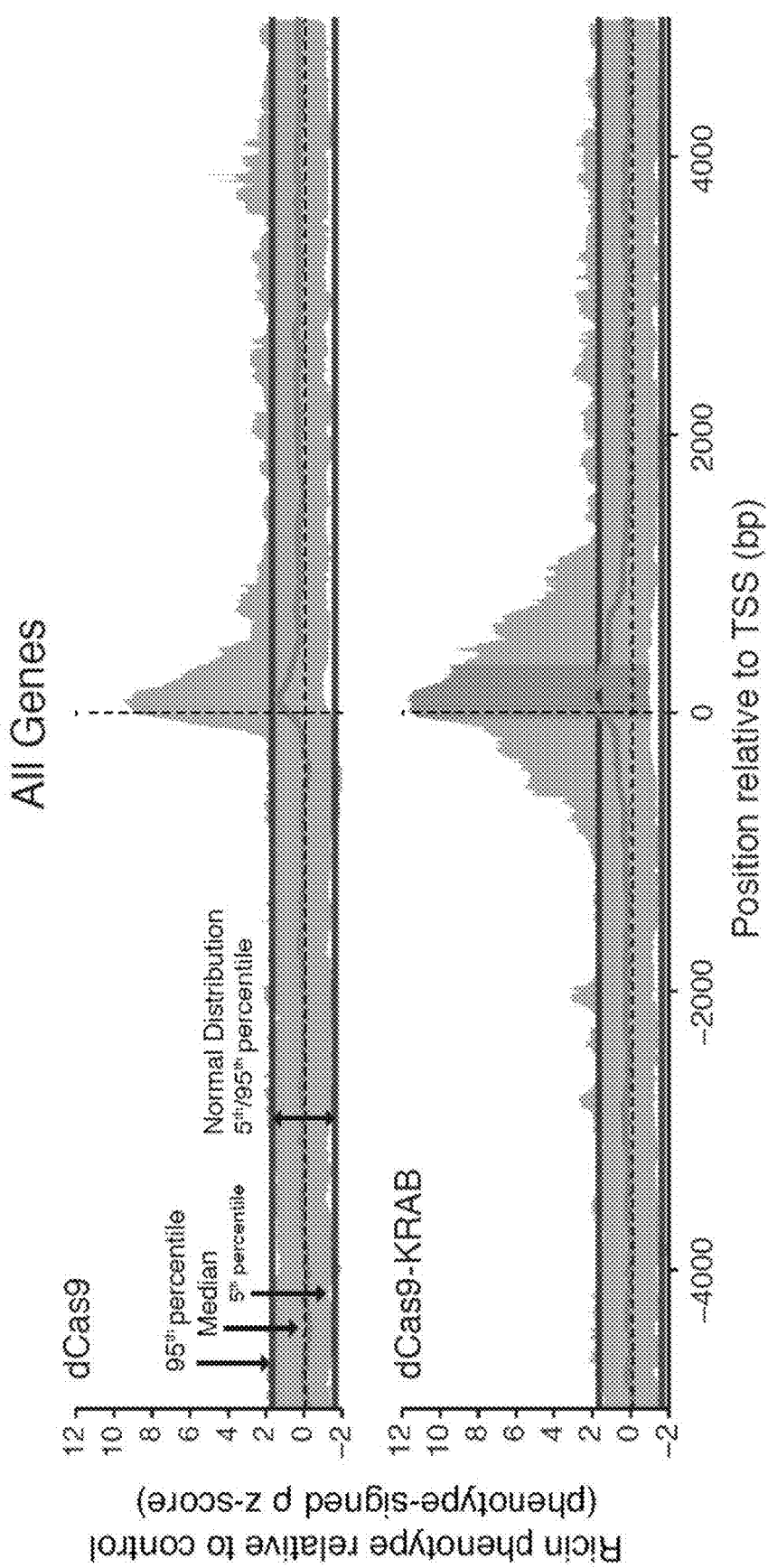
Figure 9A:
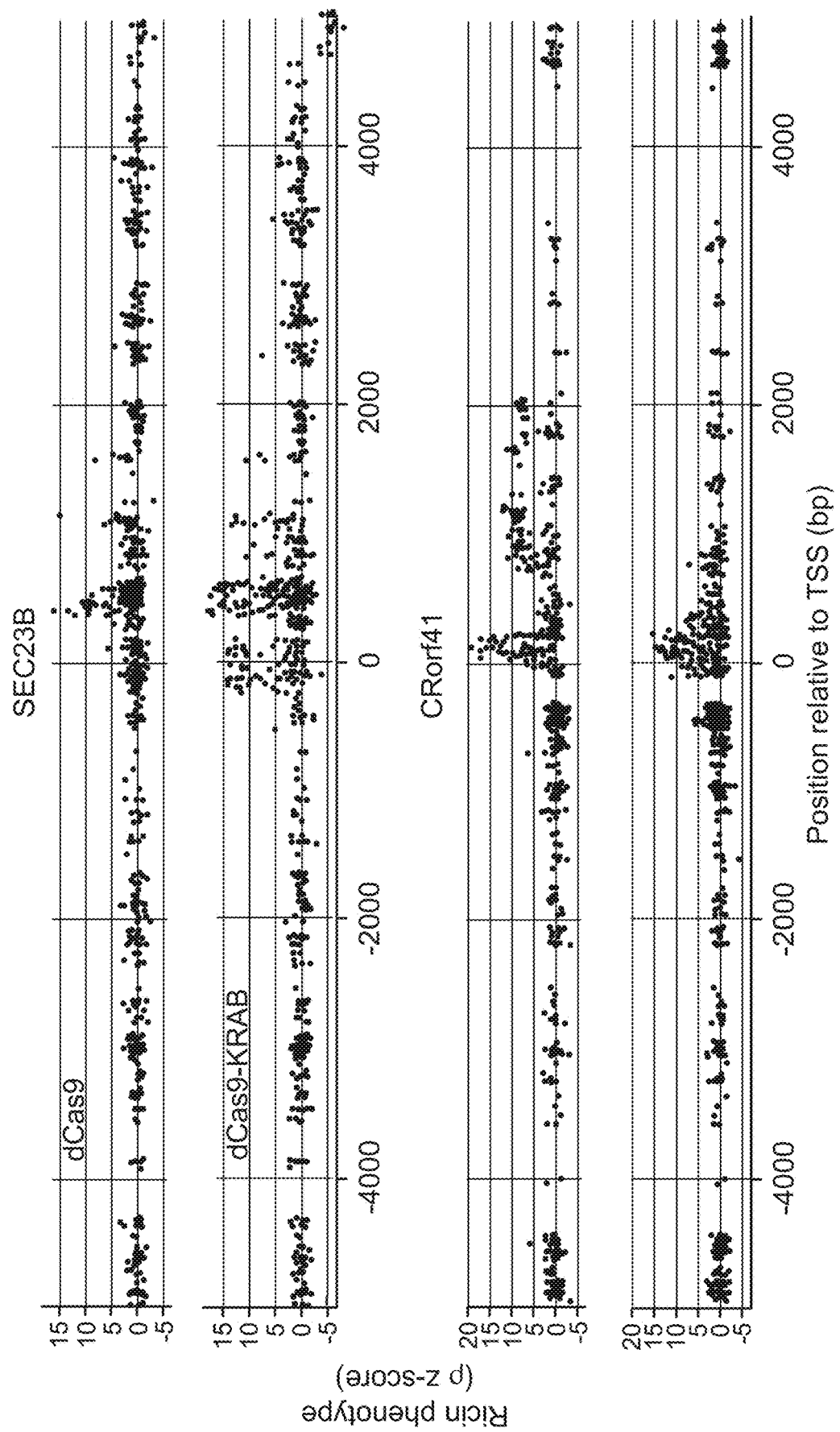

Initial inspection of data revealed that many sgRNAs potently repress gene expression, as evidenced by their impact on ricin sensitivity (FIG. 1C and FIG. 9A). Plotting this data for all 49 genes showed that active sgRNAs cluster around or just downstream from the transcription start site of each gene for dCas9-KRAB and dCas9, respectively (FIG. 1D). This activity pattern is consistent with the KRAB domain acting as a transcription repressor and dCas9 inhibiting transcription by interfering with RNA polymerase activity (Pubmed IDs: 23452860, 23849981).

Figure 9B:
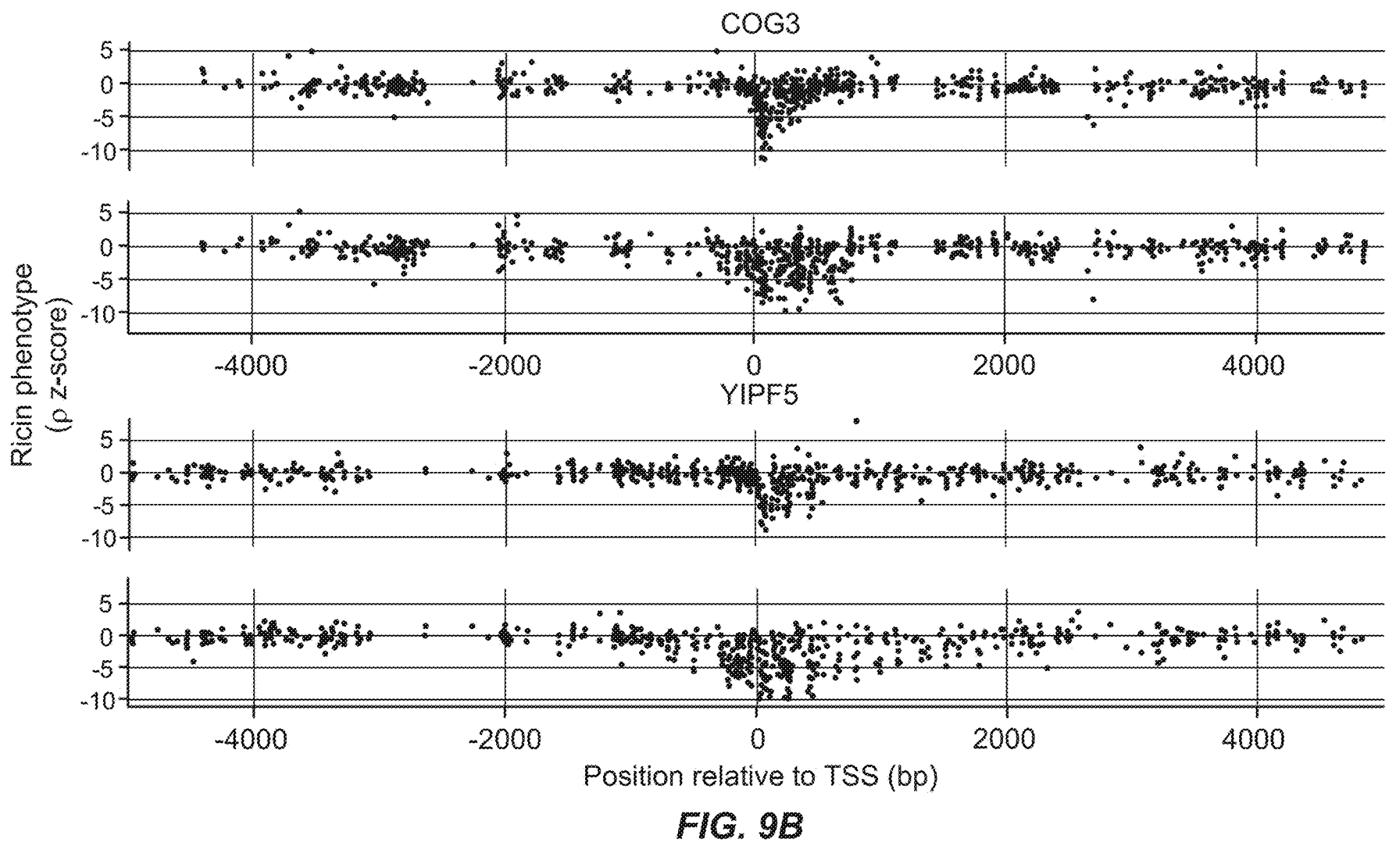
Figure 9C:
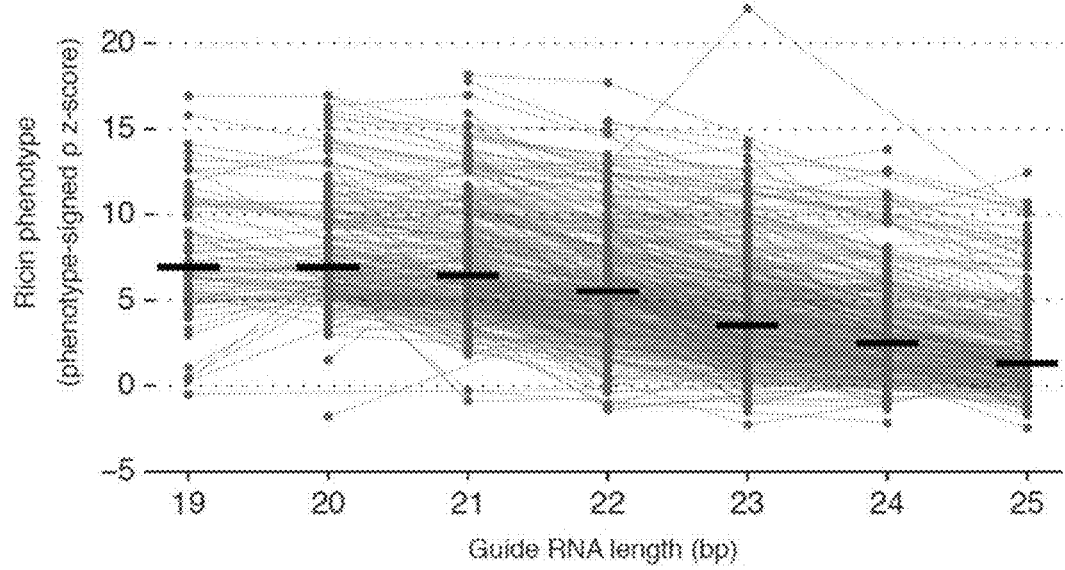
Figure 9D:
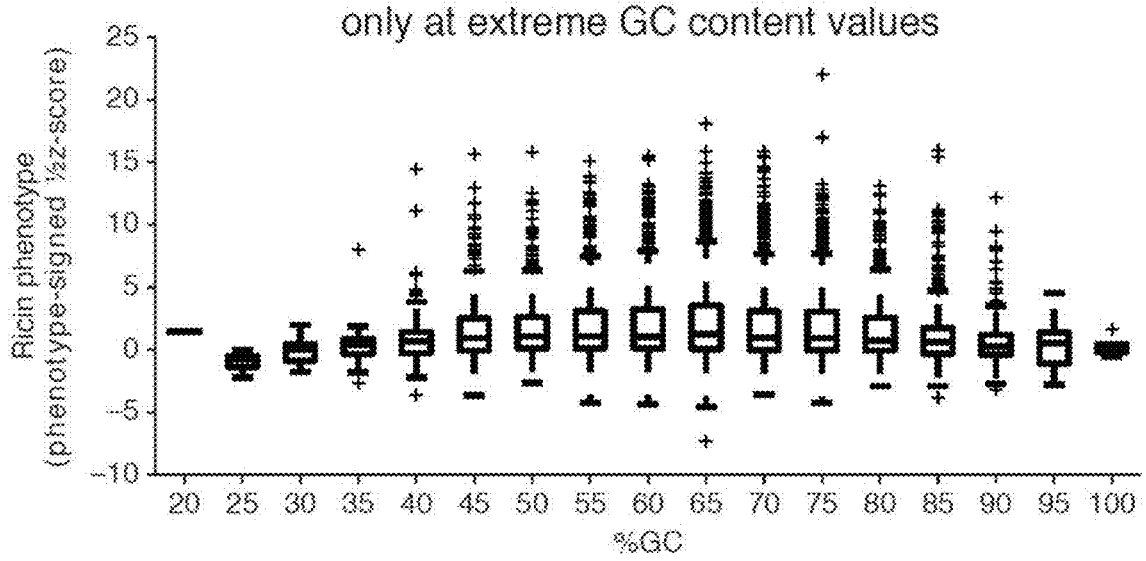
Figure 9E:
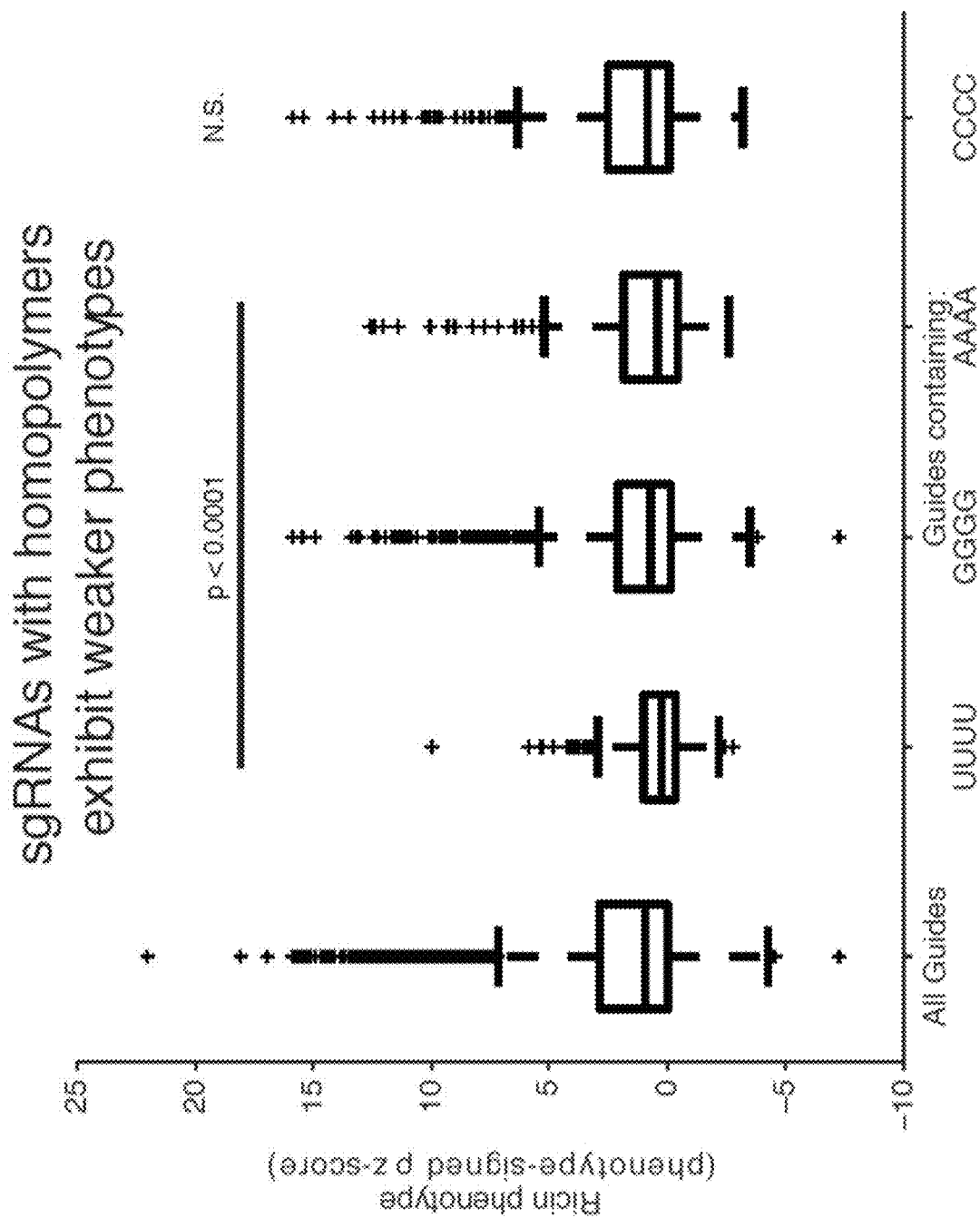

Strong CRISPRi activity was obtained by targeting dCas9-KRAB to a window of DNA from ~50 to +350 bp relative to the transcription start site of a gene, with a maximum in the ~50-100 bp region just downstream of the TSS (FIG. 1B, FIG. 1D). This suggested that optimal activity leverages the combined activity of dCas9 interference along with repression from the KRAB domain. It was also observed that sgRNAs with protospacer lengths of 18-21 base pairs were significantly more active than longer protospacer containing sgRNAs (FIG. 9B). Nucleotide homopolymers had a strongly negative effect on sgRNA activity (FIG. 9C). However, neither the DNA strand that was targeted nor the sgRNA GC content across a broad range strongly correlated with sgRNA activity (FIGS. 9D-9E).

Figure 1E:
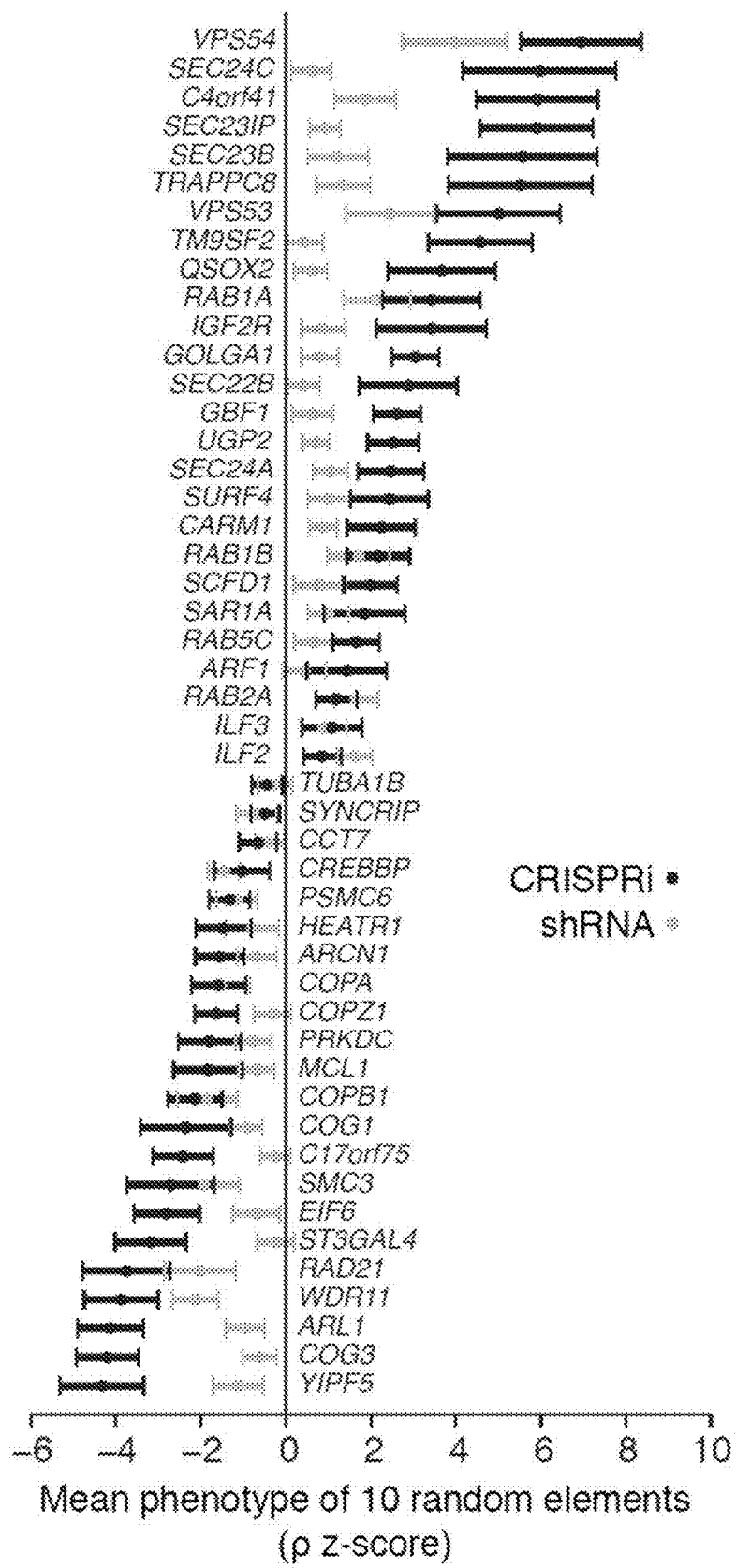
Figure 8C:
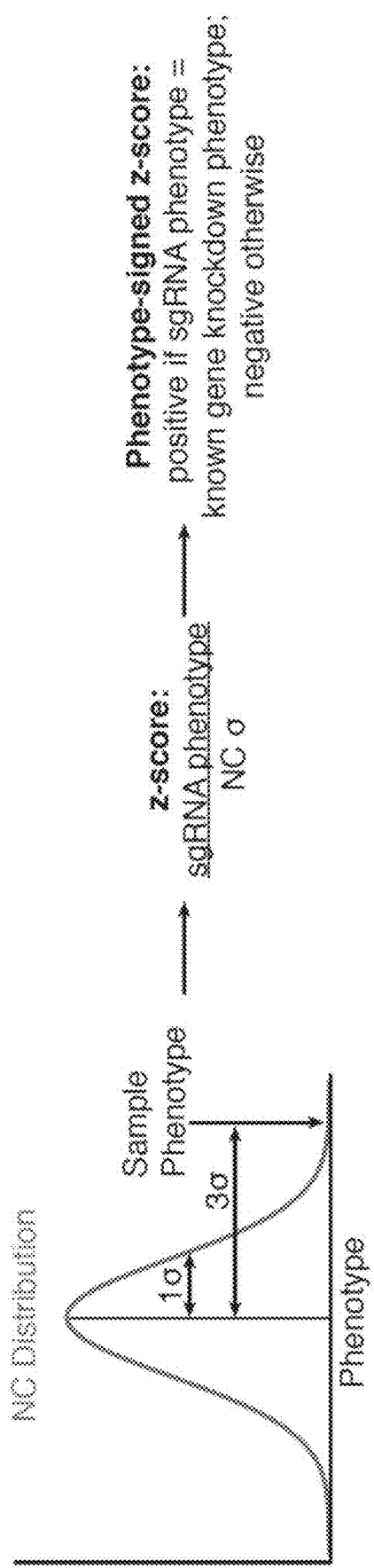
Figure 9F:
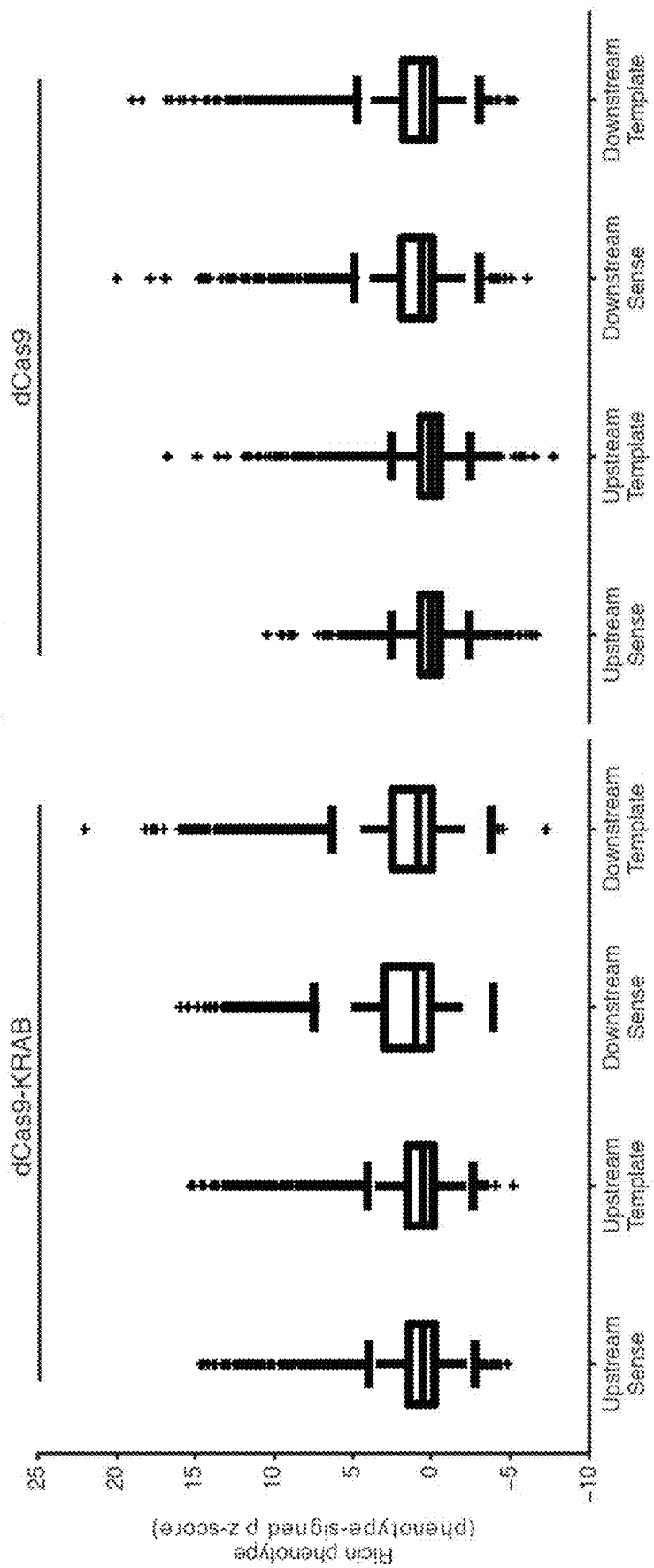
Figure 9G:
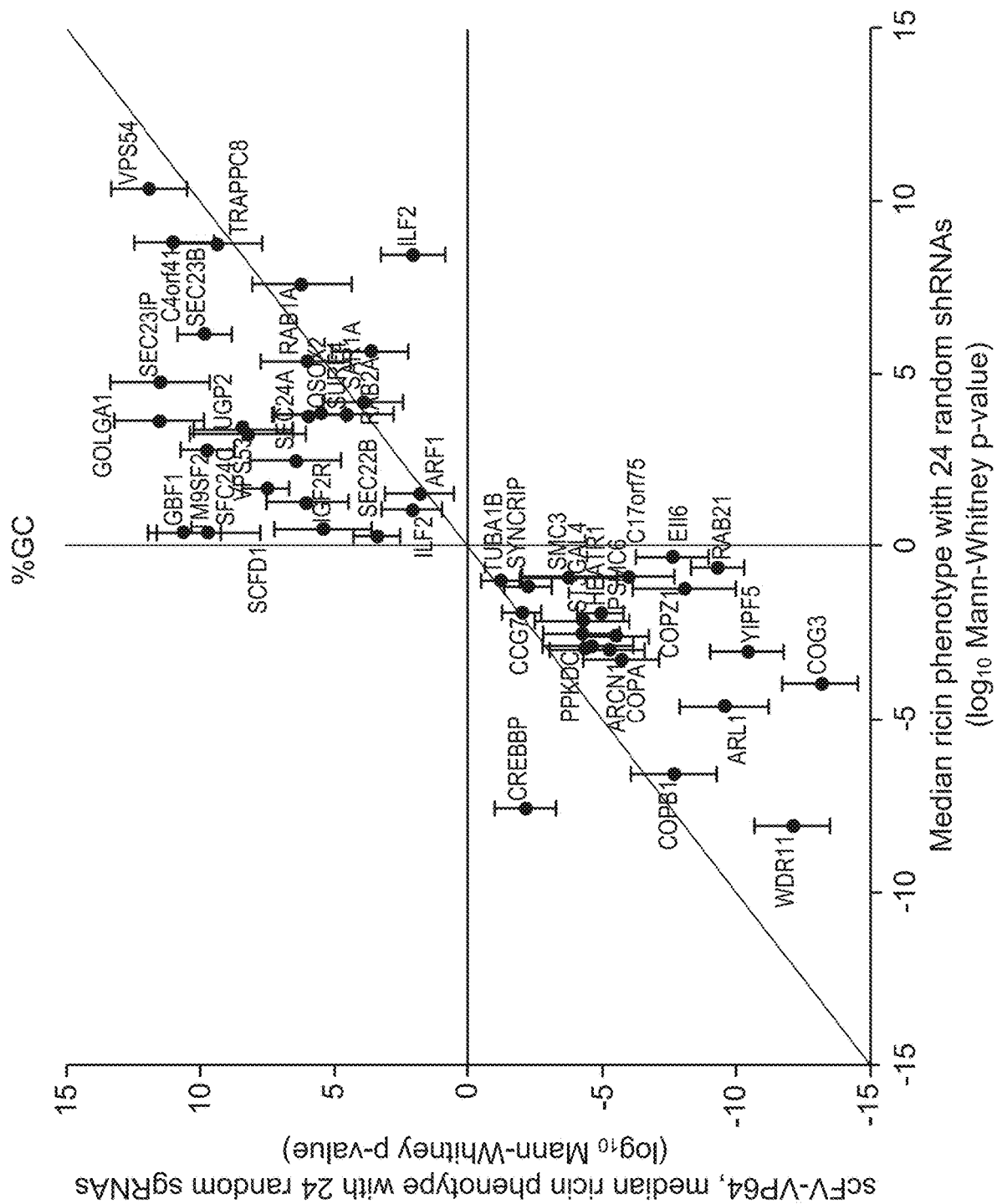

To evaluate the feasibility of genome-wide genetic screens based on CRISPRi, the strength of phenotypes obtained with CRISPRi was compared to a previously published RNAi library, applying the rules described above and then randomly subsampling the data from the sgRNA tiling library to pick sets of 10 sgRNAs. A normalized phenotype z-score was calculated by dividing mean phenotypes for each gene by the standard deviation of phenotypes of sgRNAs from the non-targeting control set (FIG. 8C). Significant ricin phenotypes were seen for each of the 49 genes. Moreover, in virtually every case the normalized ricin phenotype was stronger (in many cases far stronger) than seen with a comparably sized shRNA library (generated by sub sampling our published data). Thus CRISPRi significantly outperforms the published RNAi library (FIG. 1E and FIG. 9F). As discussed below this is due to combination of high efficacy as well as low off-target effects.

Figure 2:
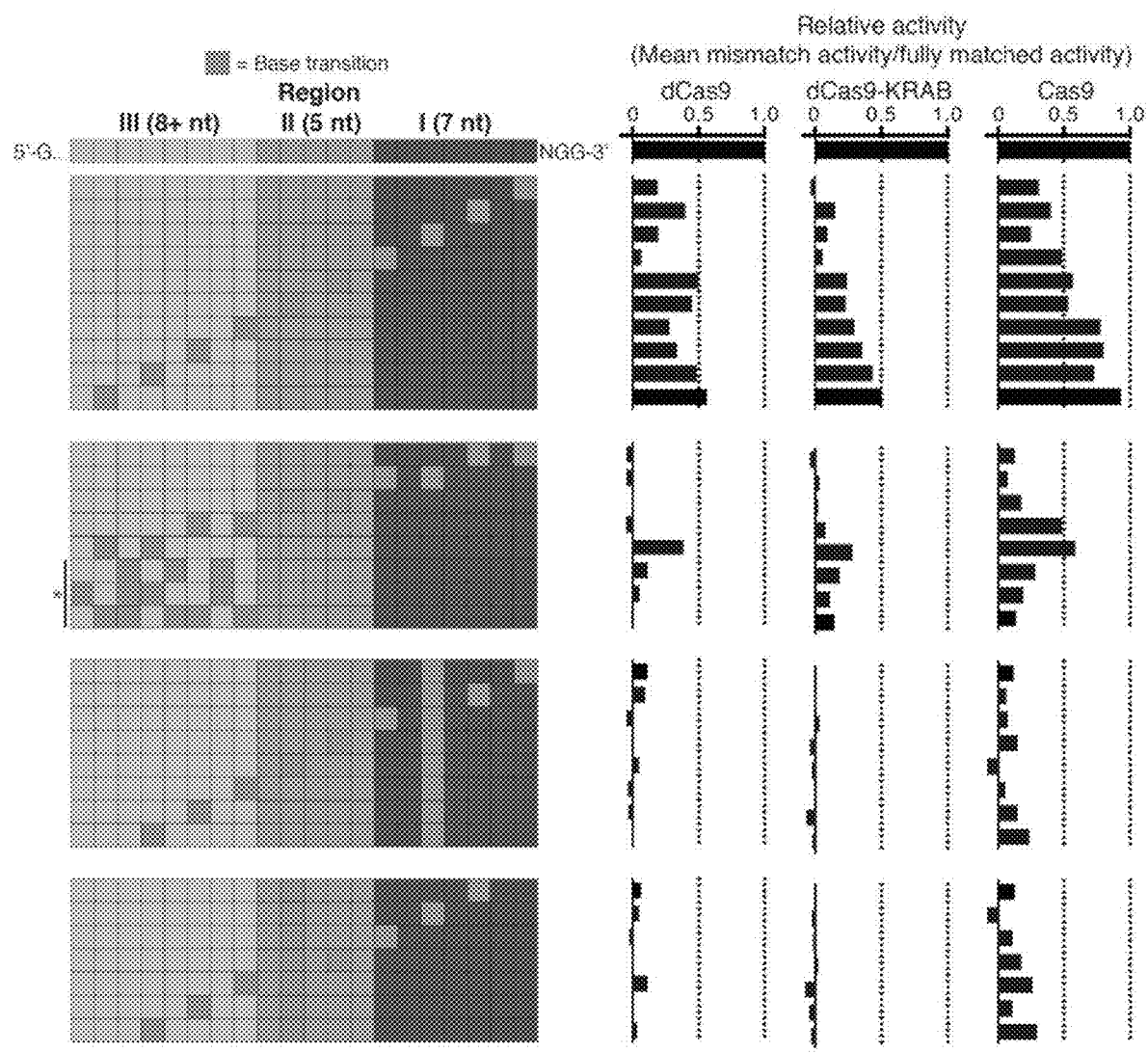
FIG. 2: CRISPRi Activity is Highly Sensitive to Mismatches Between the sgRNA and DNA sequence. The on- and off-target activity of dCas9, dCas9-KRAB and Cas9 was measured for a series of sgRNAs with a varying number and position of mismatches. The measured off-target activity of each sgRNA with one or more mismatch is displayed as percent of the on-target activity for the corresponding sgRNA with 0 mismatches. The sgRNA series denoted with a star represents sgRNAs with 3, 4, or 5 mismatch base pairs randomly distributed across region 3 of the sgRNA sequence. Data are displayed for each mismatch position as the mean of all sgRNAs with that mismatch; see FIG. 10 for individual sgRNA activities. sgRNAs were included in the analysis only if the fully matched guide was highly active (phenotype-signed z-score>=4); N=5 for dCas9, 11 for dCas9-KRAB, and 10 for Cas9.
Figure 10:
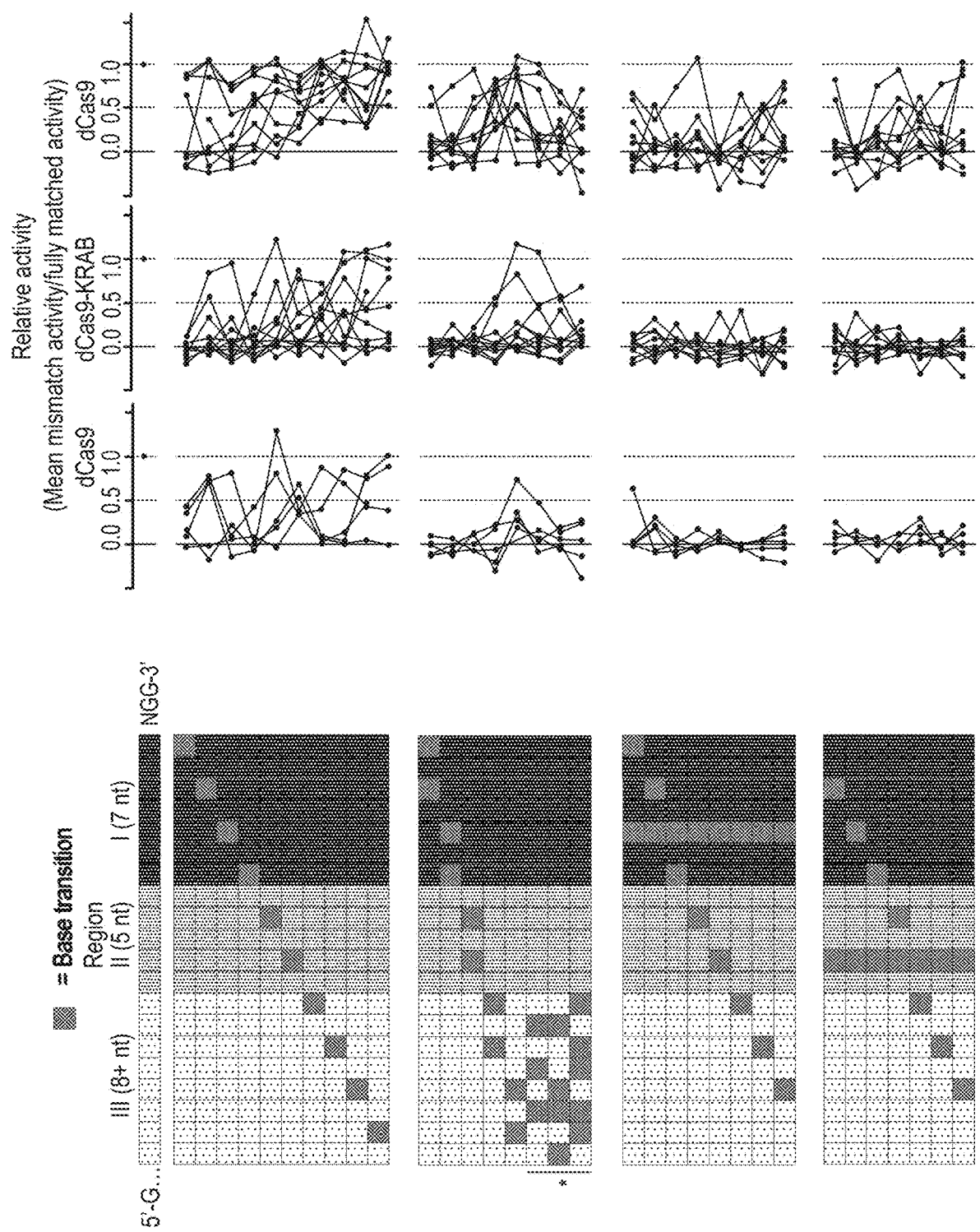
FIG. 10: CRISPRi Activity is Highly Sensitive to Mismatches Between the sgRNA and DNA sequence. The on- and off-target activity of dCas9, dCas9-KRAB and Cas9 was measured for a series of sgRNAs with a varying number and position of mismatches. Each sgRNA is a point with the related mismatch series connected by lines. The measured off-target activity of each sgRNA with one or more mismatch is displayed as percent of the on-target activity for the corresponding sgRNA with 0 mismatches. The sgRNA series denoted with a star represents sgRNAs with 3, 4, or 5 mismatch base pairs randomly distributed across region 3 of the sgRNA sequence. sgRNAs were included in the analysis only if the fully matched guide was highly active (phenotype-signed z-score>=4); N=5 for dCas9, 11 for dCas9-KRAB, and 10 for Cas9.

B. CRISPRi Transcriptional Silencing is Highly Sensitive to Mismatches Between Target DNA Site and the sgRNA To define rules for CRISPRi off-target activity at endogenous genes, a set of highly active sgRNAs from the test library was selected. For each of these sgRNAs, the activity of a series of derivative sgRNAs with a variable number and position of mismatches was tested (FIG. 2). This experiment allowed measurement of the amount of off-target gene repression for sgRNAs with mismatch base pairing relative to sgRNAs for which high on-target activity was established. Even a single mismatch at the 3' end of the protospacer decreased CRISPRi activity while sgRNAs that passed the bioinformatics off-target filter, showed very little activity (FIG. 2 and FIG. 10). The dCas9 and dCas9-KRAB proteins showed greater sensitivity to mismatches between the sgRNA and target DNA than observed with Cas9-mediated gene deletion. From this analysis, it was concluded that CRISPRi has minimal off-target transcriptional repression activity at sites with 3 or more mismatches, even if the sgRNA binding site is close to a transcription start site (FIG. 2).

C. A High Throughput-Tiling Screen Defines Rules for CRISPRa Activity at Endogenous Genes dCas9 fused to the herpes virus VP16 domain can activate transcription when targeted upstream of the transcription start site of a gene (Pubmed ID: 23849981). Initial CRISPRa experiments suggested that robust activation of transcription required multiple sgRNA binding sites in the promoter of a gene or multiple sgRNAs targeted to one promoter, which would limit the utility of CRISPRa for library-based screens (Pubmed IDs: 23849981, 23979020, 23892898, 23977949, 23892895, 23907171). However, an improved CRISPRa method, termed sunCas9, in which expression of a single sgRNA with one binding site is sufficient to robustly activate transcription. In the sunCas9 system, a single dCas9 fusion protein bound to DNA recruits multiple copies of the activating effector domain, thus amplifying our ability to induce transcription.

To define rules for CRISPRa, the tiling library targeting genes that modulate cellular sensitivity to ricin was used to define how and where CRISPRa activates transcription. It was previously shown for 5 out of the 49 genes in this tiling library that knockdown and plasmid overexpression resulted in the opposite ricin phenotypes. For example, knockdown of SEC23A sensitized cells to ricin, whereas SEC23A overexpression desensitized cells to ricin. This observation provided internal positive control genes for CRISPRa activity (Pubmed ID: 23394947).

Figure 3A:
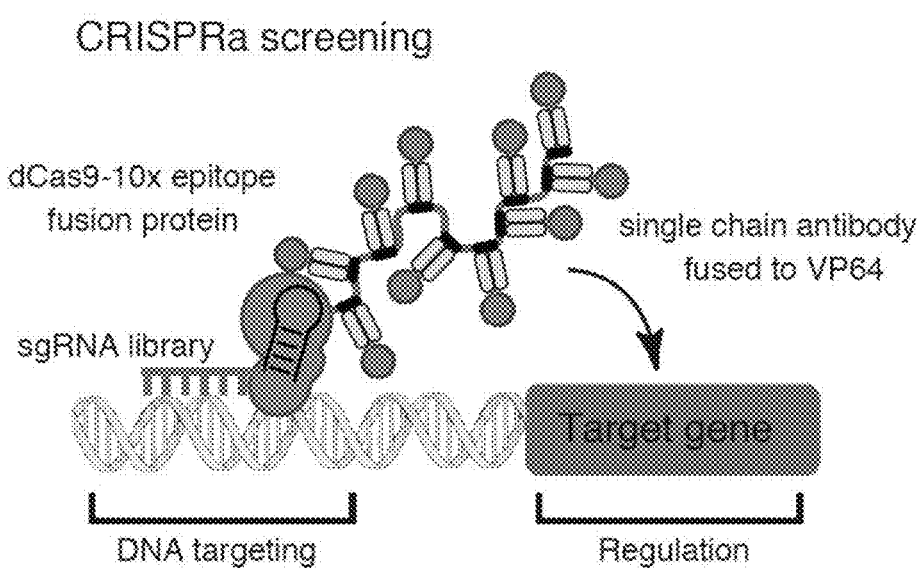
FIGS. 3A-3E: A Tiling sgRNA Screen Defines Rules for CRISPRa Activity at Endogenous Genes in Human Cells.
Figure 3B:
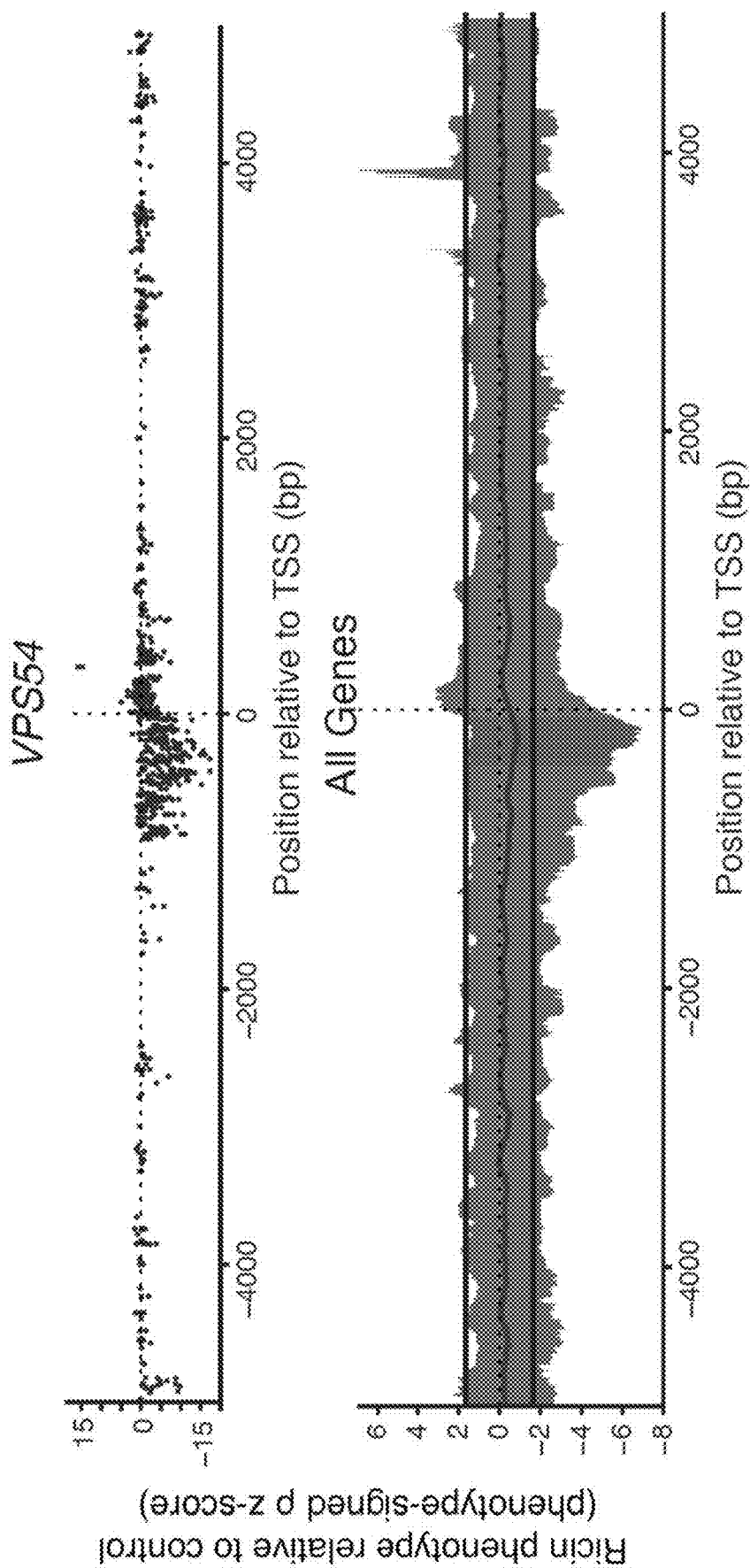
Figure 11A:
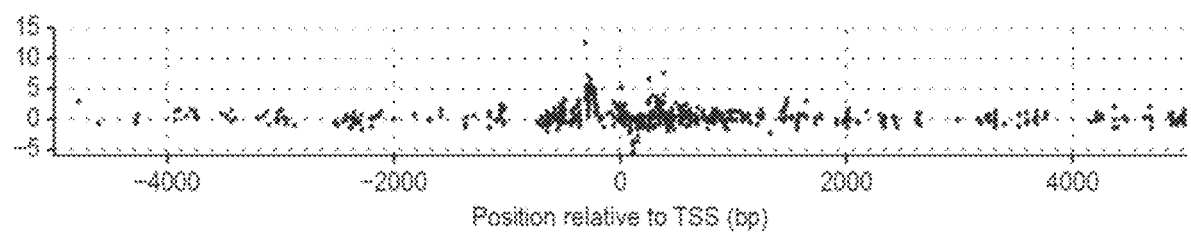
FIG. 11A-FIG. 11B: A Tiling sgRNA Screen Defines Rules for CRISPRa Activity at Endogenous Genes in Human Cells.
Figure 11A:
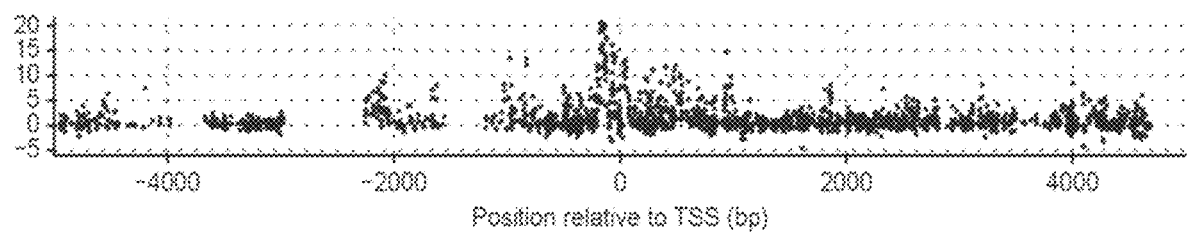
Figure 11A:
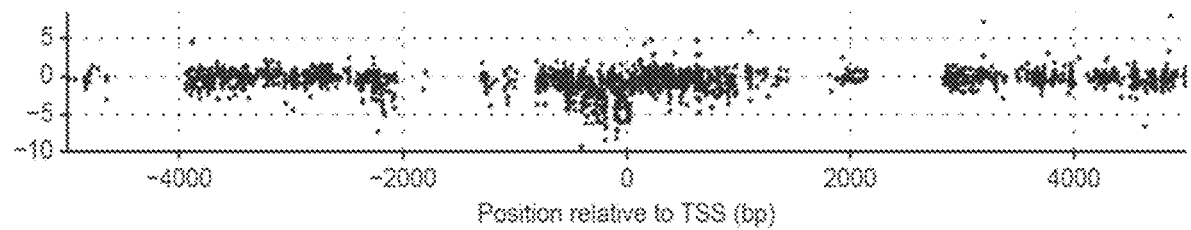
Figure 11A:
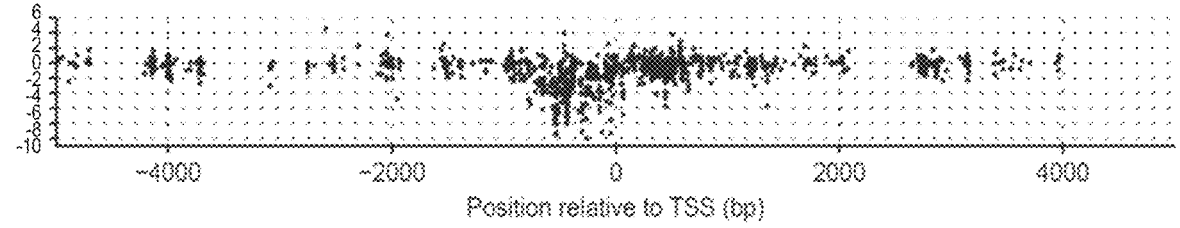
Figure 11B:
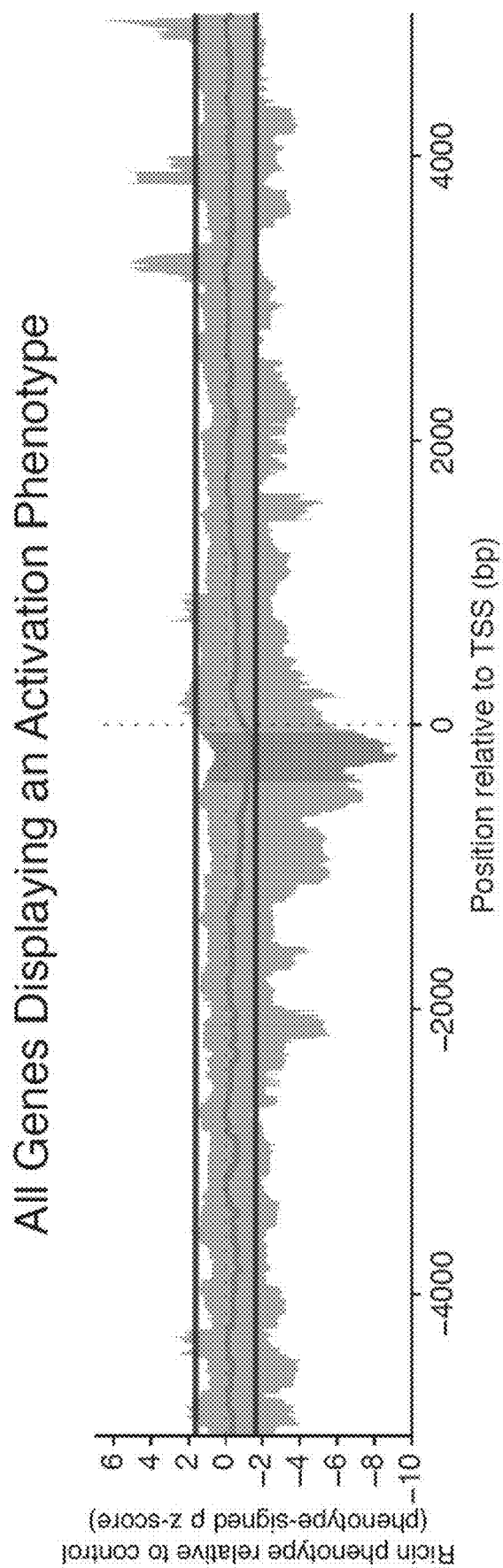
Figure 12A:
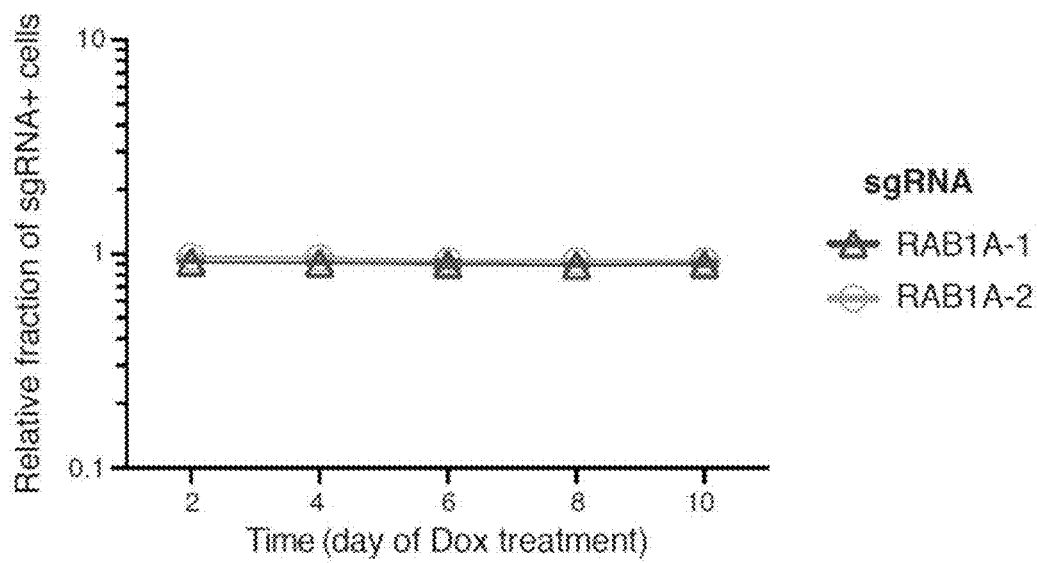
FIG. 12A-FIG. 12B: CRISPRi Can Inducibly and Rapidly Repress Transcription.
Figure 12B:
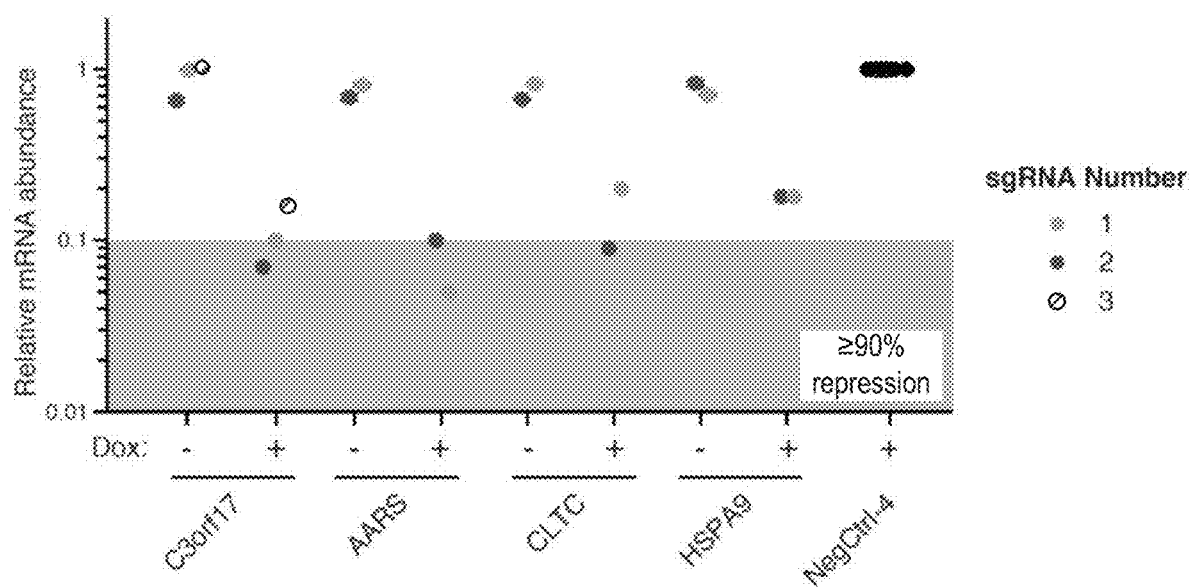

K562 cells were transduced to stably express the sunCas9 system (FIG. 3A) with the sgRNA tiling library and screened for ricin phenotypes as described for CRISPRi above. Analysis of data for individual genes or averaged data for all 49 genes demonstrated that many sgRNAs for each gene affected ricin resistance, suggesting many sgRNAs potently activate gene expression (FIG. 3B and FIG. 11A-FIG. 11B). Importantly, negative control sgRNAs showed very little activity and were not correlated between biological replicate screens, suggesting that CRISPRa activity is specific. A peak of active sgRNAs for CRISPRa was observed at −400 to −50 bp upstream from the transcription start site (FIG. 3B). This activity pattern fits with a model in which each VP16 domain can bind the mediator complex and recruit basal transcription machinery, which actives transcription when spaced appropriately from a transcription start site (Pubmed ID: 14657022). With this system genes that are poorly expressed can be turned on and the expression of well-expressed genes can be increased. In some cases, when a well-expressed gene is only modestly turned up, this increase in gene expression can robustly modulate cellular sensitivity to ricin. These CRISPRi/a tiling screens provided rules for how CRISPRi/a controls expression of endogenous genes. These tiling sgRNA libraries could be used as a tool for evaluating the activity and specificity of future dCas9 fusion proteins or further iterations of CRISPRi/a.

Figure 3C:
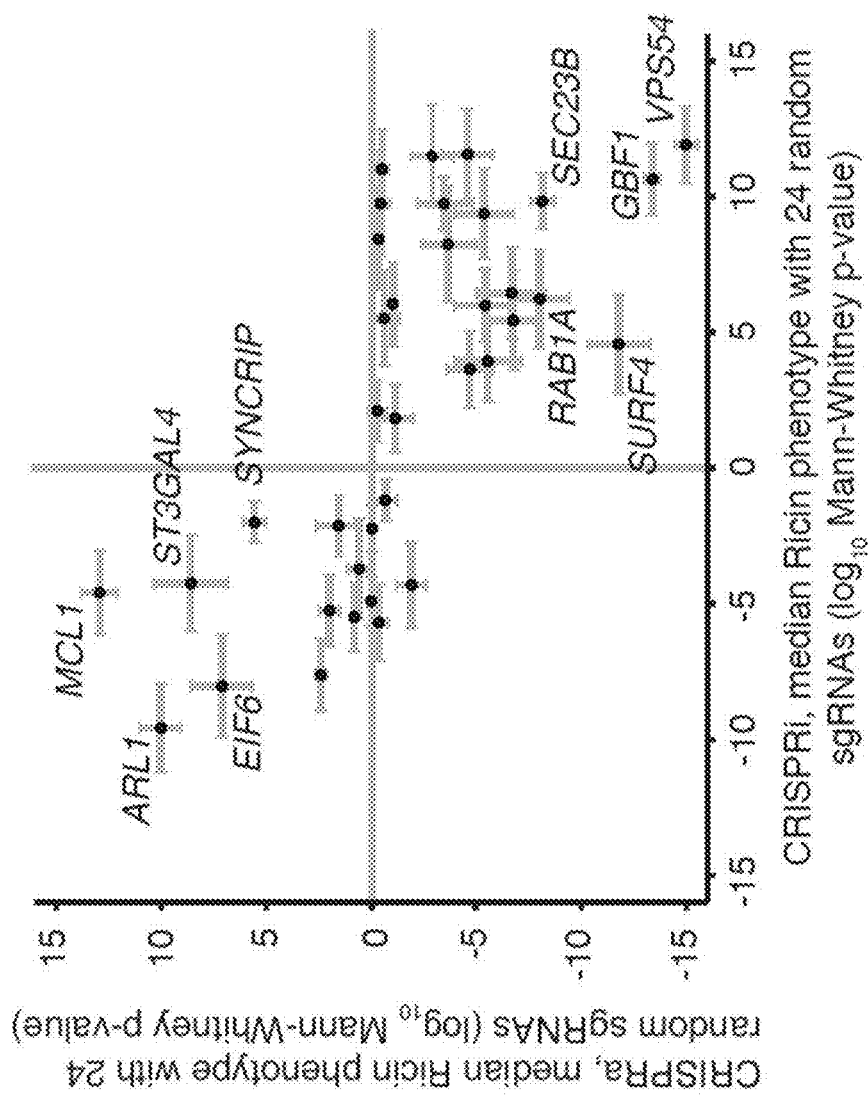

D. An Allelic CRISPRi/a Series of Transcript Activation and Repression Demonstrates Protein Abundance Dynamically Modulates the Cellular Response to Ricin For many genes, it is unknown how the relative abundance of the encoded protein relates to its function. A strong anti-correlation was observed in our ricin screens between CRISPRa phenotypes and CRISPRi or RNAi phenotypes for individual genes (FIG. 3C). This result suggests the abundance of many proteins can modulate both resistance and sensitivity to a toxin. As the genes targeted by the test library were selected based on a knockdown phenotype, all genes showed phenotypes in the CRISPRi screen, but only a subset showed phenotypes in the CRISPRa screenNo genes show the same phenotype when overexpressed as when repressed.

Figure 3D:
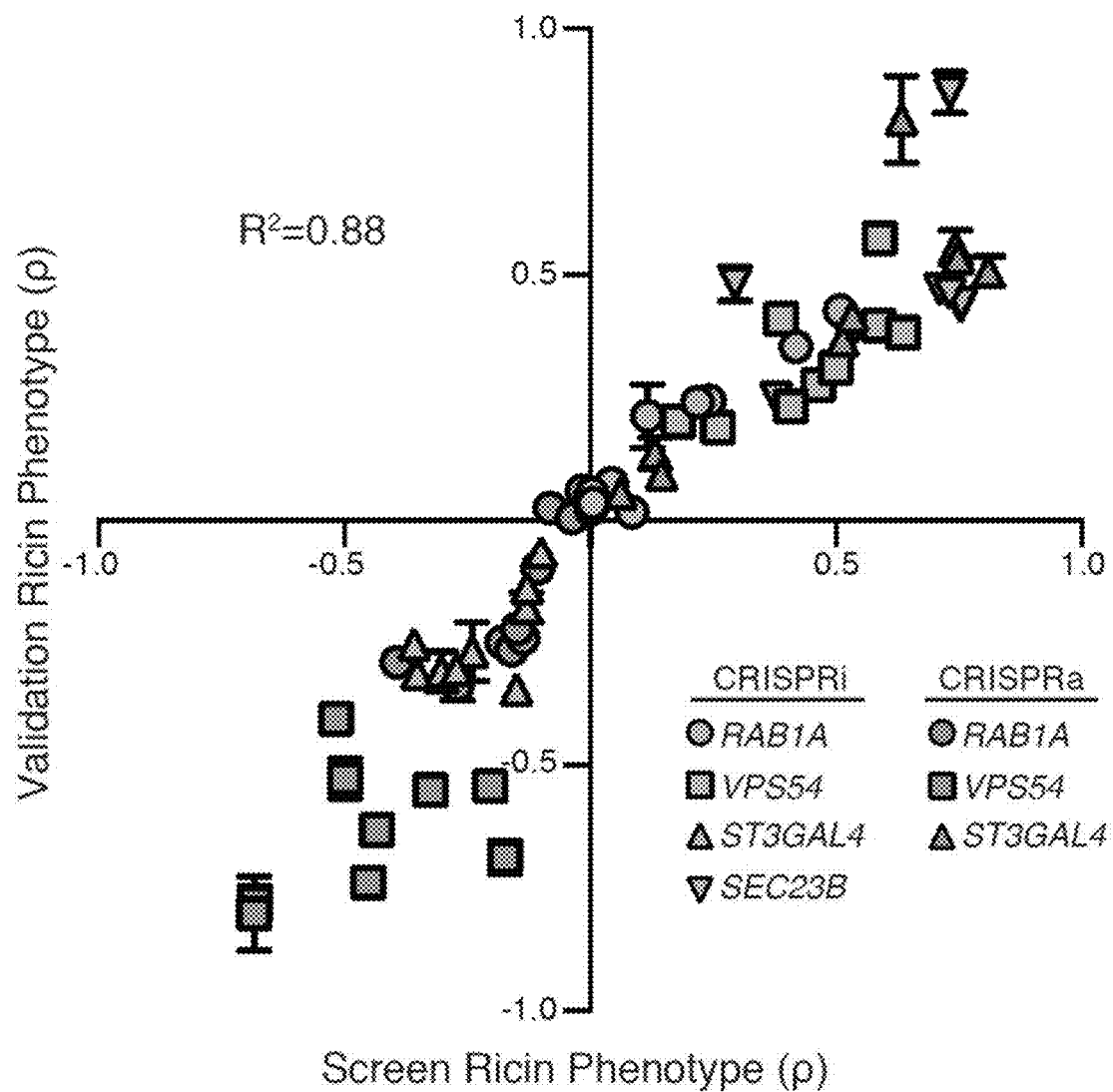
Figure 3E:
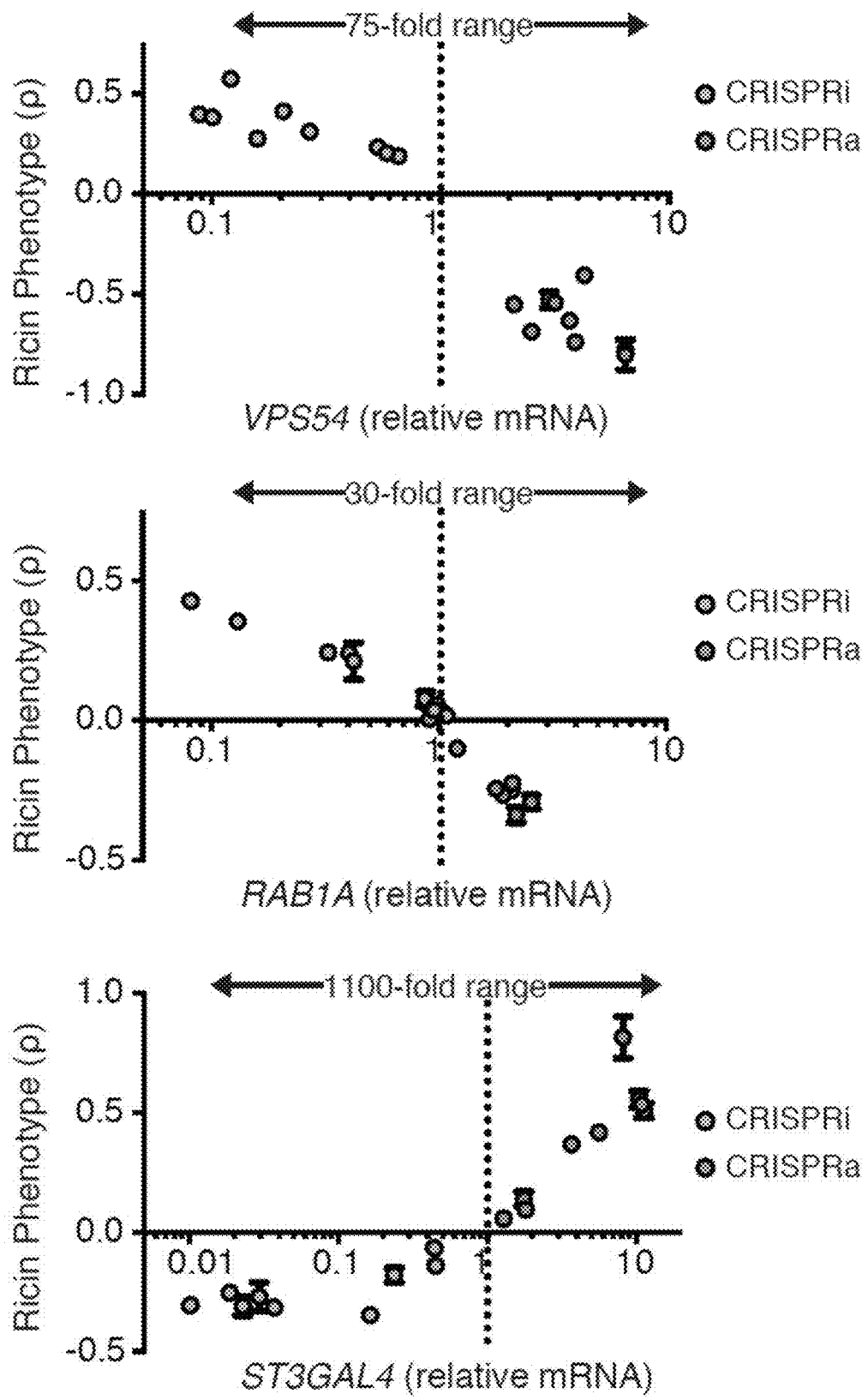

The results from both the CRISPRi and CRISPRa screens were validated as follows. An allelic series of sgRNAs were selected by phenotype from the screen and each sgRNA was individually re-tested. For each sgRNA, both the ricin phenotypes as well as the change in abundance of the targeted transcript were quantified (FIG. 3D-FIG. 3E). The results show that the CRISPRi/a screens produced reliable phenotype scores that were robustly reproduced in re-test experiments. CRISPRi/a can activate and repress the transcription of endogenous genes over a wide dynamic range (up to ~1000-fold) (FIG. 3E). Thus, CRISPRi/a can be used to produce an allelic series of overexpression and knockdown for endogenous genes, enabling systematic interrogation of how gene dosage controls cellular functions of interest (FIG. 3D-FIG. 3E).

E. A Robust and Highly Specific Genome-Scale CRISPRi Screening Platform

The results of the test CRISPRi screen demonstrated the ability to pick active sgRNAs with low off-target activity and provided a set of rules enabling the design of a robust genome-scale sgRNA library. A library size of 10 sgRNAs/gene was chosen for the following reasons. Over half of the sgRNA conforming to these rules gave clear ricin phenotypes suggesting that, for a library with 10 sgRNAs per gene, 94% of the genes would have 2 or more highly active sgRNAs. Additionally, qPCR validation of the CRISPRi allelic series for ST3GAL4 demonstrated that 40% of sgRNAs picked by our activity algorithm showed at least a 10-fold reduction in target gene expression. Finally, computational sub-sampling of the phenotypic data from the tiling library sgRNA data to 10 sgRNAs per gene and calculation of p values for hit genes indicated that a library with 10 sgRNAs per gene would reliably detect hit genes.

A genome-scale CRISPRi sgRNA library targeting 15,997, human protein-coding genes (10 sgRNAs per TSS, targeting 19,000 TSS) with 11,000 non-targeting control sgRNAs for a total of 211,894sgRNAs was synthesized and cloned. Library sgRNAs were designed as protospacers of 18-21 base pairs targeting the transcription start site (or sites) of each gene in a −50 to +350 base pair window with spacing rules to prevent overlapping sgRNA sequences and excluding sgRNAs with predicted off-target activity as defined by the mismatch sgRNA series analysis.

The library was evaluated by first screening for genes essential for cell growth in K562s cells. Briefly, the genome-scale CRISPRi library was transduced (using lentivirus) into K562 cells stably expressing dCas9-KRAB. The entire genome-scale library was then screened by growing cells for 10 days at a minimum library coverage of 3,750-fold in a single spinner flask. Two biological replicate screens were conducted to estimate variation.

Figure 4A:
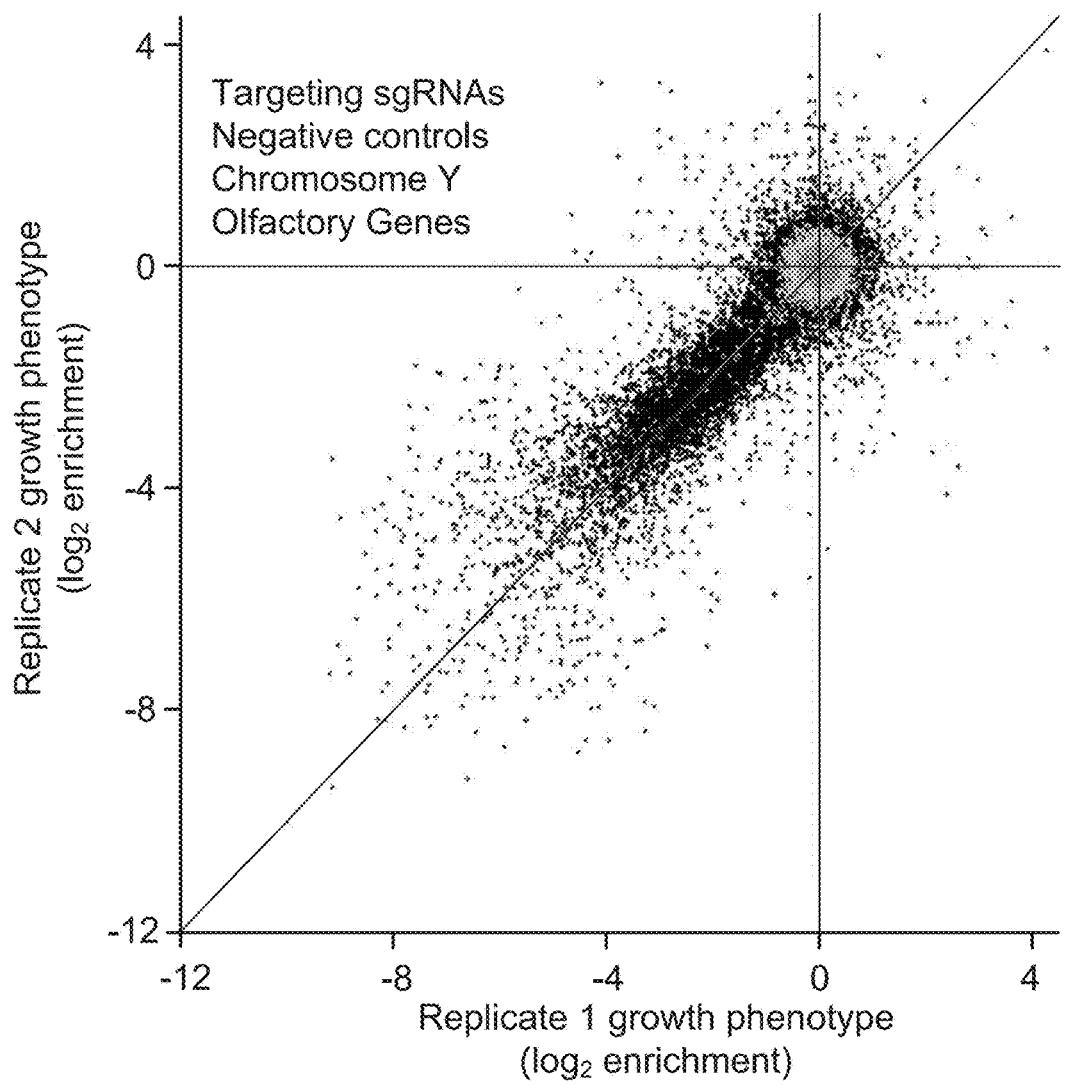
FIGS. 4A-4D: A Genome-Scale CRISPRi Screen Reveals Genes Required for Cell Growth in Human Cells.

To characterize the screening methodology and library design, the correlation between screen replicates and the negative control distributions was examined. The sgRNA phenotypes observed in each biological replicate were strikingly well correlated indicating the screen is highly reproducible (FIG. 4A). Individual sgRNAs showed dramatic depletion (up to 256-fold) over a 10-day screen, demonstrating individual sgRNAs can have profound effects on cell growth. The distribution of negative-control sgRNAs was very narrow with little correlation between replicates, suggesting the off-target activity of these controls is very low (FIG. 4A). While 99.7% of the negative controls were essentially inactive, a very small number of sgRNAs showed significant activity that was correlated between replicate screens.

Figure 4B:
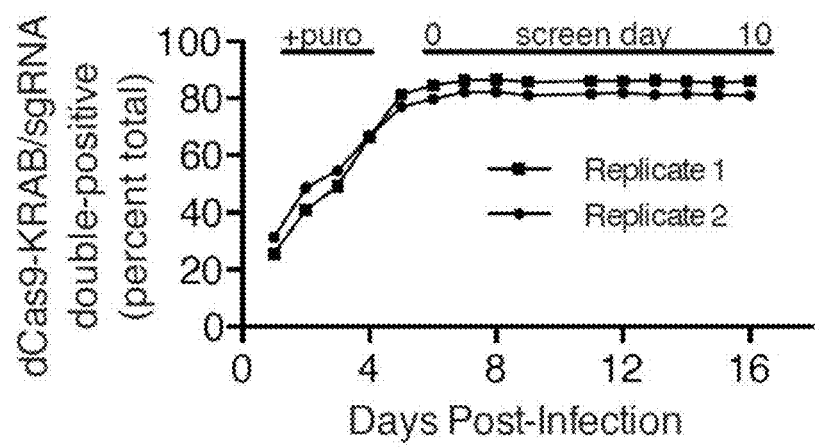

To further explore the prevalence of off-target effects, two classes of genes that should not show any on-target activity in the screen were examined: olfactory receptors and genes on the Y chromosome. The sgRNAs targeting these genes were designed and picked in the same manner as the rest of library; however, olfactory receptors should not be expressed in this cell type and, as K562 cells are female, sgRNAs targeting genes on the Y chromosome have no DNA target. Both negative control gene sets showed on average no phenotype and very little correlation between replicates, suggesting that the few observed phenotypes are due to stochastic noise (FIG. 4A). Additionally, no evidence of non-specific toxicity due to expression of dCas9-KRAB or the sgRNA library was observed in K562s, suggesting that dCas9 bound to the genome is not toxic under these conditions (FIG. 4B). These data suggest that CRISPRi is highly specific and non-toxic.

F. Defining Essential Genes, Complexes and Pathways in Human Cells by CRISPRi

Figure 4C:
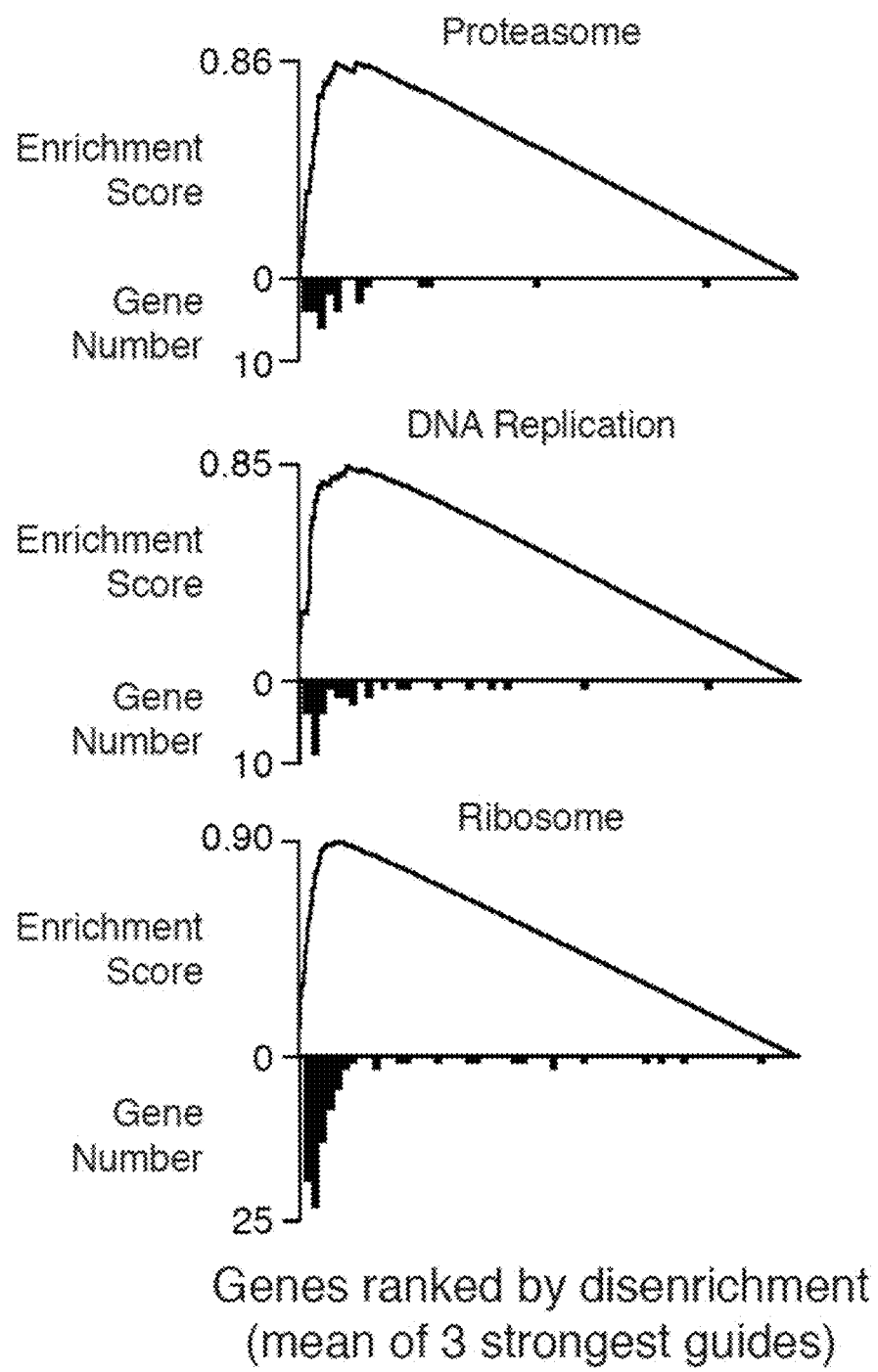
Figure 4D:
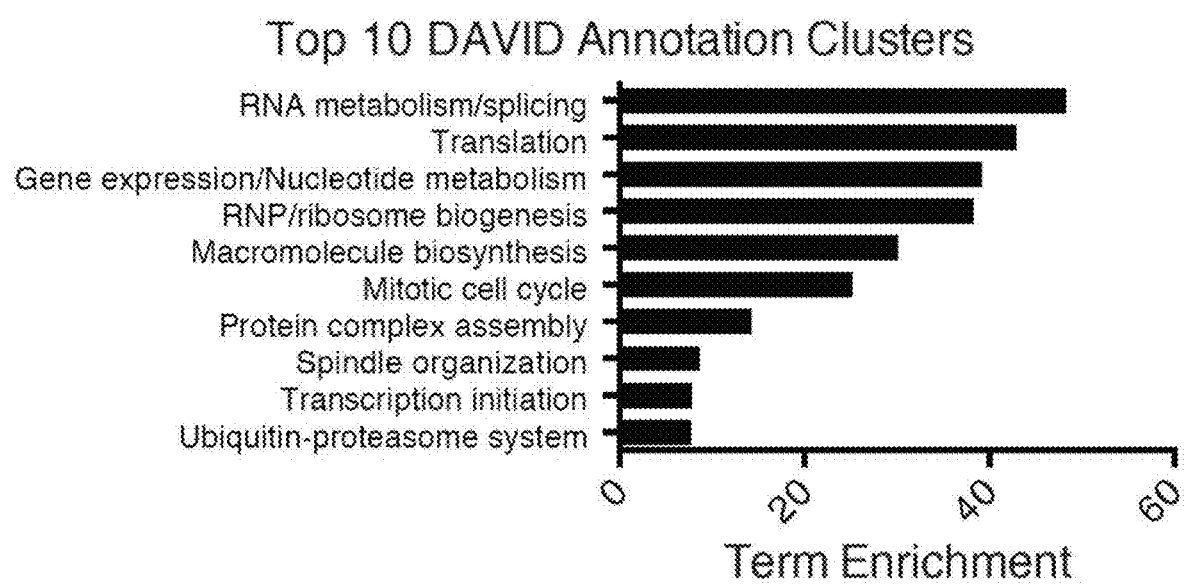

To identify hit genes in this screen, a metric of average growth phenotype ($\gamma$) for the top three sgRNAs for each gene was used (see methods). Using this metric, many genes involved in essential cellular processes were observed to strongly deplete. The top functional categories of depleted genes were transcription, splicing, and translation machinery, and biosynthetic and metabolic pathways (FIG. 4C). sgRNAs targeting components of the ribosome, the proteasome, and DNA replication machinery were strongly depleted (FIG. 4D). These data validate the sgRNA activity algorithm and demonstrate that CRISPRi can be used as a loss of function screening method.

G. Dynamically Controlling Gene Expression with CRISPRi

Figure 5A:
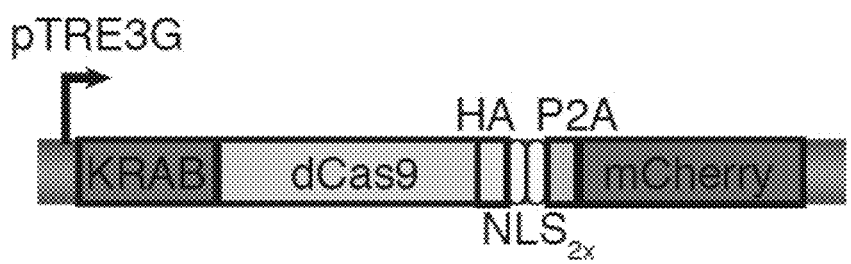
Figure 5B:
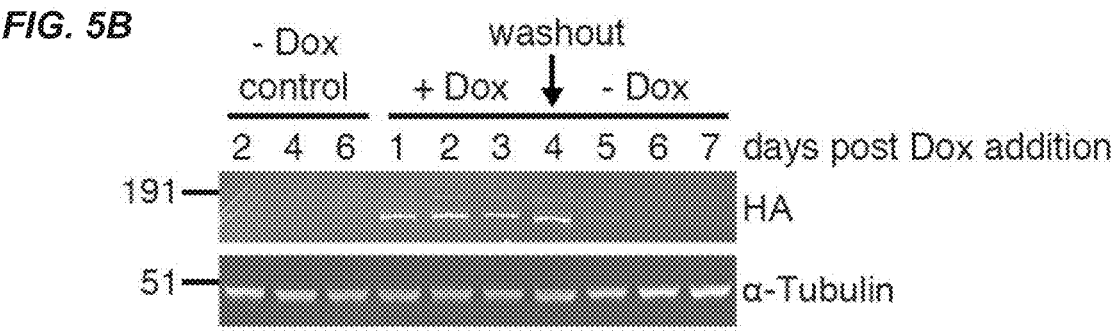
Figure 5C:
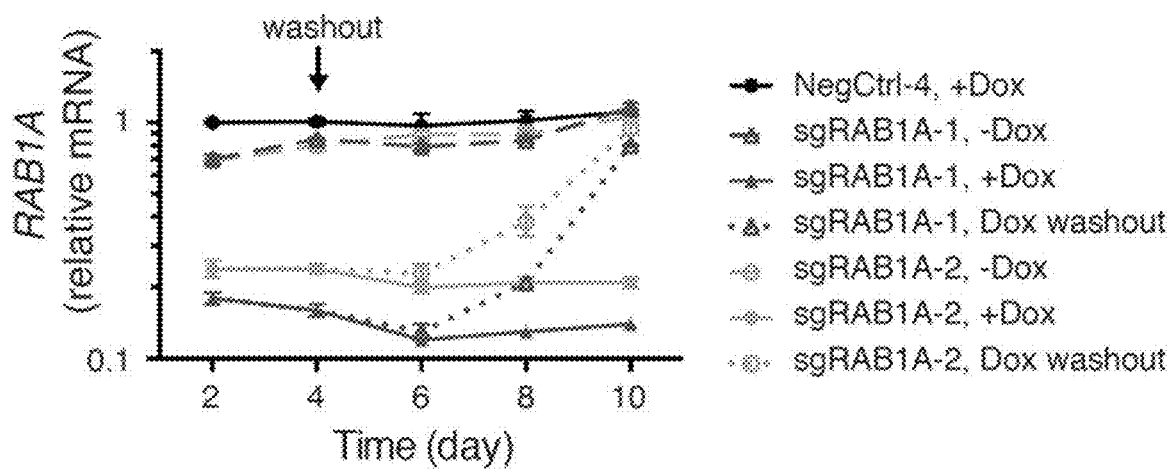

The ability to reversibly tune the expression of select transcripts is a powerful tool for evaluating transcript function, especially in the context of animal models used to study normal development and disease. To evaluate the applicability of CRISPRi to this purpose, a lentiviral expression construct was cloned that places an optimized KRAB-dCas9 fusion protein under the control of a doxycycline-inducible promoter. The ability of this expression construct to dynamically control gene expression in human cells was tested (FIG. 5A). Expression of KRAB-dCas9 from this construct was strongly activated in the presence of doxycycline (FIG. 5B), and in cells transduced with either of two sgRNAs targeting RAB1A (validated in this study), this induction of KRAB-dCas9 robustly depleted RAB1A mRNA (FIG. 5C). The induced repression was reversible following withdrawal of doxycycline from the cell culture media, demonstrating that KRAB-dCas9 does not create a permanently repressive chromatin state at targeted promoters.

Figure 5D:
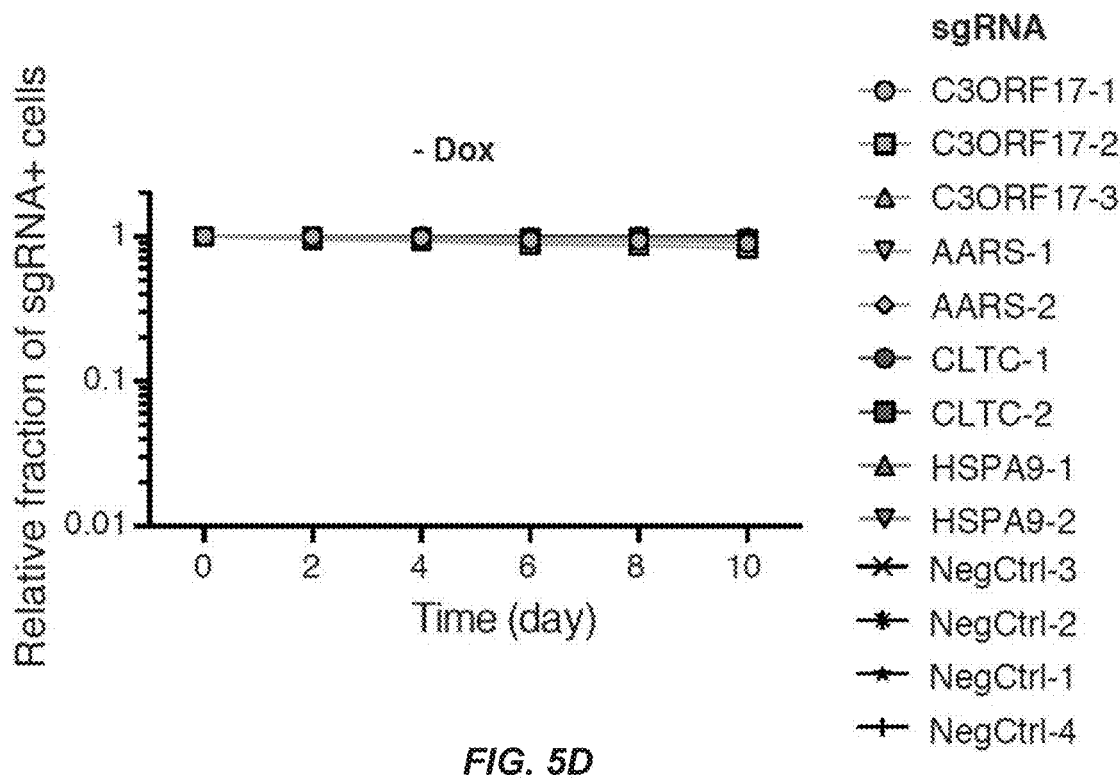

To evaluate dynamic control of CRISPRi-mediated phenotypes, the inducibilty of growth defects caused by repression of several genes identified in the genome-scale CRISPRi growth screen was evaluated. These genes included C3orf17, which has no described function. For each gene, 2 or 3 sgRNAs were selected and the effects on growth from each were quantified with and without KRAB-Cas9 induction (FIG. 5D). Cells expressing these sgRNAs showed almost no growth phenotype in the absence of doxycycline but rapidly and robustly depleted from the population following addition of doxycycline (FIG. 5D). In the strongest cases, over 95% of sgRNA-expressing cells with induced KRAB-dCas9 were depleted in 10 days (sgAARS-1 and sgHSPA9-1).

Figure 5E:
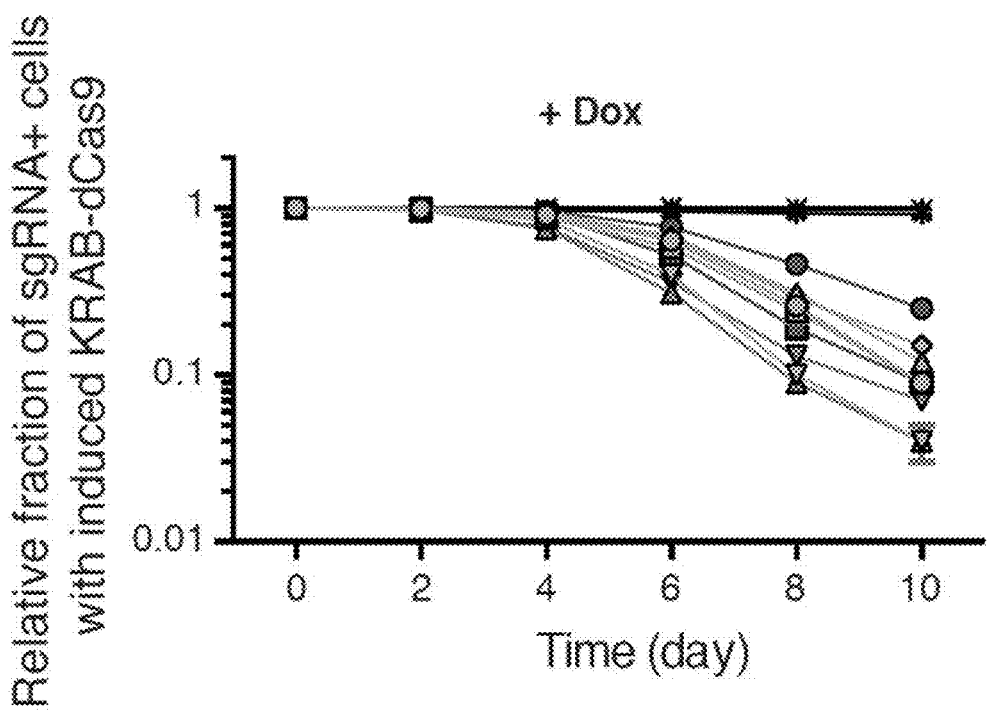
Figure 5H:
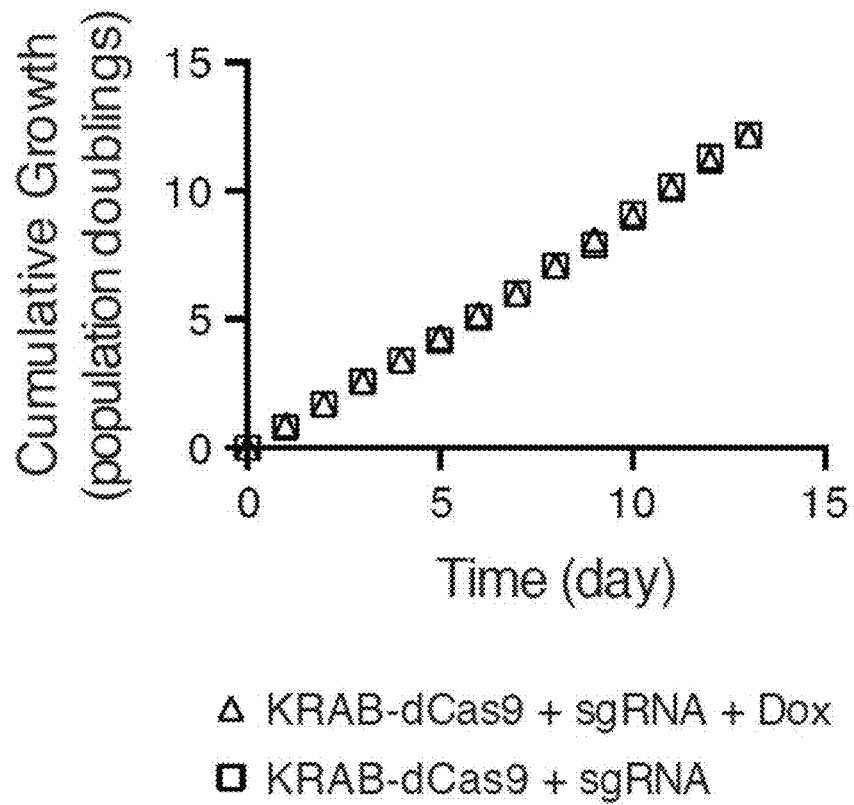

To test dynamic control of gene expression of essential genes on a larger scale, a sub-library targeting 426 manually curated genes (10 sgRNAs/TSS or 5,773 total sgRNAs, with 750 non-targeting controls) was cloned. These were identified in the genome-scale growth screen or were predicted to be required for cell growth by published data sets (Pubmed ID: 23394947). The sgRNAs present in this library were selected independently of the genome-scale CRISPRi library but were designed using the same sgRNA activity algorithm. This library was transduced into K562 cells stably expressing our inducible KRAB-dCas9 fusion protein and evaluated for cell growth effects in the presence and absence of doxycycline. Consistent with the individual results, only 4 sgRNAs depleted strongly in the absence of doxycycline; however, with induction of KRAB-dCas9, many sgRNAs strongly depleted (FIG. 5E). Negative control sgRNAs produced a narrow distribution of phenotypes that was uncorrelated between biological replicates with or without doxycycline (FIG. 5D). Additionally, no evidence that targeted KRAB-dCas9 generally decreases cell growth was found (FIG. 5F). Taken together, these results demonstrate CRISPRi is non-toxic, inducible and reversible.

Figure 6A:
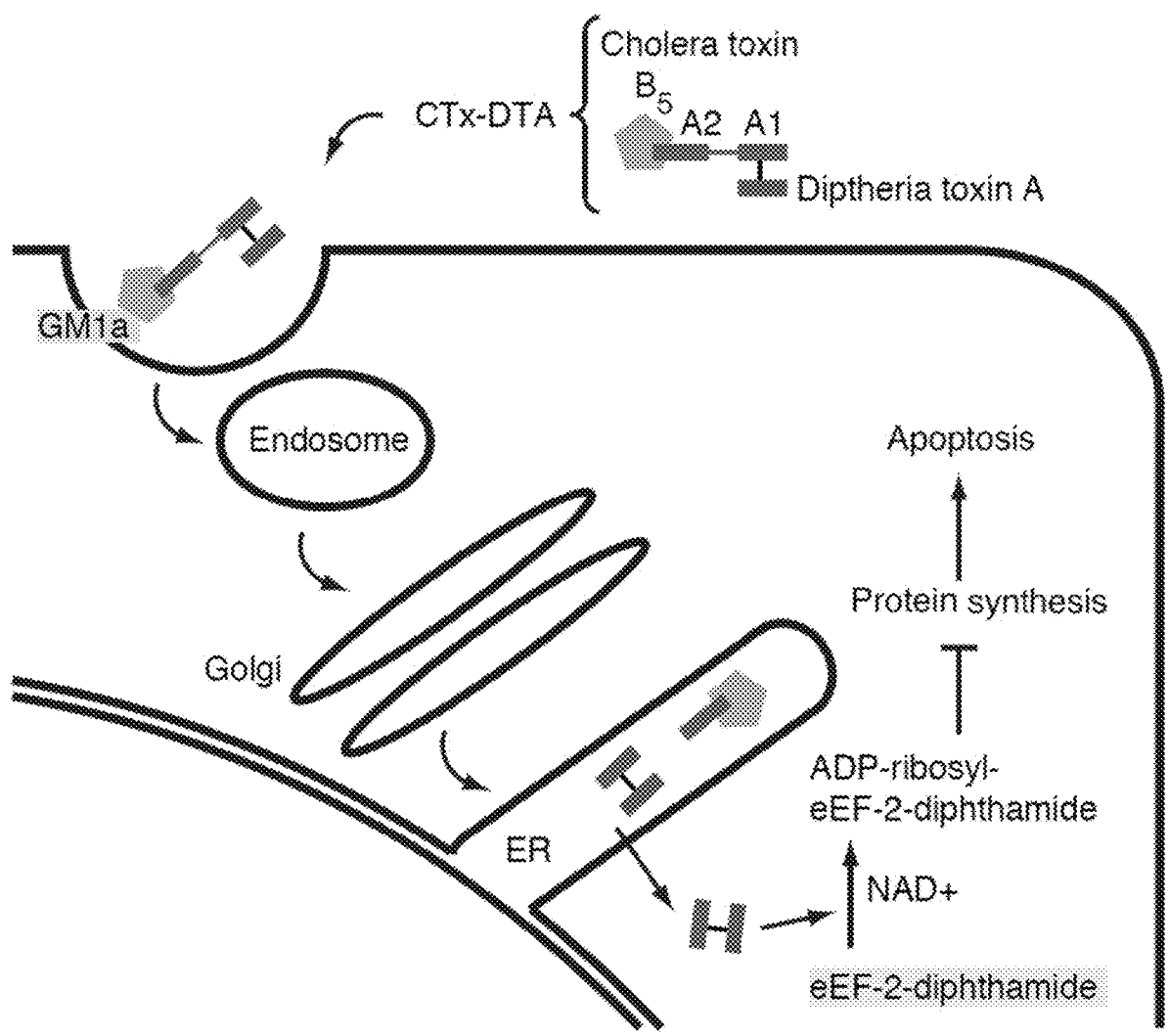
FIG. 6A-FIG. 6C: A Genome-Scale CRISPRi Screen Reveals Known and New Pathways and Complexes Governing the Response to a Choler-Diptheria Fusion Toxin.

H. A Genome-Scale CRISPRi Screen Reveals Pathways and Complexes that Govern Response to Cholera and Diptheria Toxin To test the performance of the CRISPRi approach for the detection of genes controlling a more complex cellular phenotype, a genome-scale CRISPRi screen was performed for genes that modulate sensitivity to a chimeric toxin composed of the diphtheria toxin catalytic A subunit covalently linked to cholera toxin (CTx-DTA, FIG. 6A). The mechanism of cellular entry and toxicity of both cholera toxin and diphtheria toxin are partially characterized. Furthermore, genes controlling CTx-DTA sensitivity have previously been identified using a haploid mutagenesis approach (Pubmed ID: 22123862). The B subunit of cholera toxin binds to GM1 gangliosides on the cell surface and this interaction is required for toxin internalization (FIG. 6A) (Pubmed ID: 22919642, 22069586, 7000782). After endocytosis, the B subunit mediates retrograde trafficking via the Golgi to the endoplasmic reticulum (ER), where a disulfide bond between the cholera toxin A1 and A2 moieties is reduced. The ER-associated degradation (ERAD) machinery is thought to mediate retro-translocation of the A1 subunit and the fused diphtheria toxin A subunit to the cytosol. Once the chimeric toxin is localized to the cytoplasm, the diphtheria catalytic subunit ADP-ribosylates the diphthamide residue in Elongation Factor 2, halting translation and killing the cell (FIG. 6A).

Figure 13A:
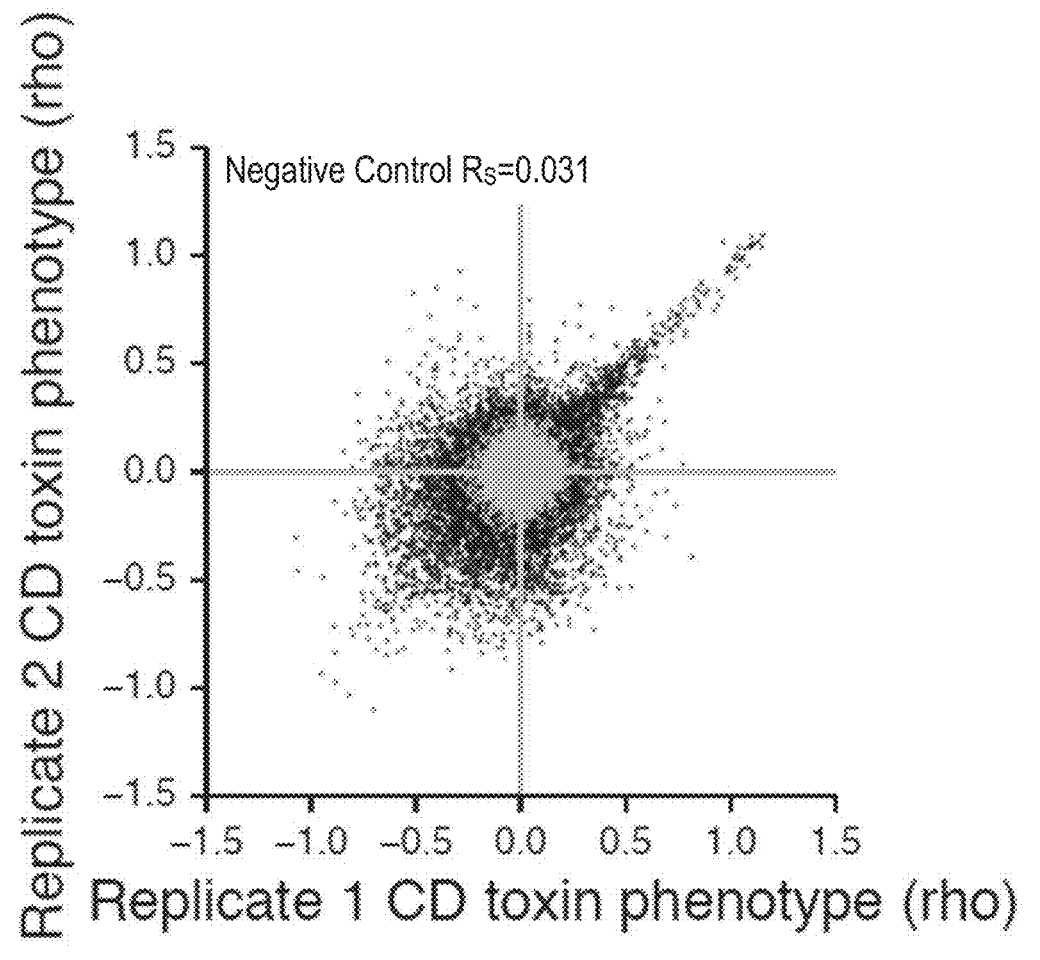

K562 cells stably expressing dCas9-KRAB were transduced with a genome-scale CRISPRi library. Cells expressing this library of sgRNAs were either grown under standard conditions or treated with several pulses of CTx-DTA over the course of 10 days. This screen was carried out in two biological replicates (FIG. 13A). Strong highly correlated enrichment and depletion of many sgRNAs was observed, indicating that CRISPRi can identify genes that modulate both resistance and sensitivity to a selective pressure. These results demonstrate that the screening approach yields reproducible results in screens in which a strong selective pressure is applied.

Figure 6B:
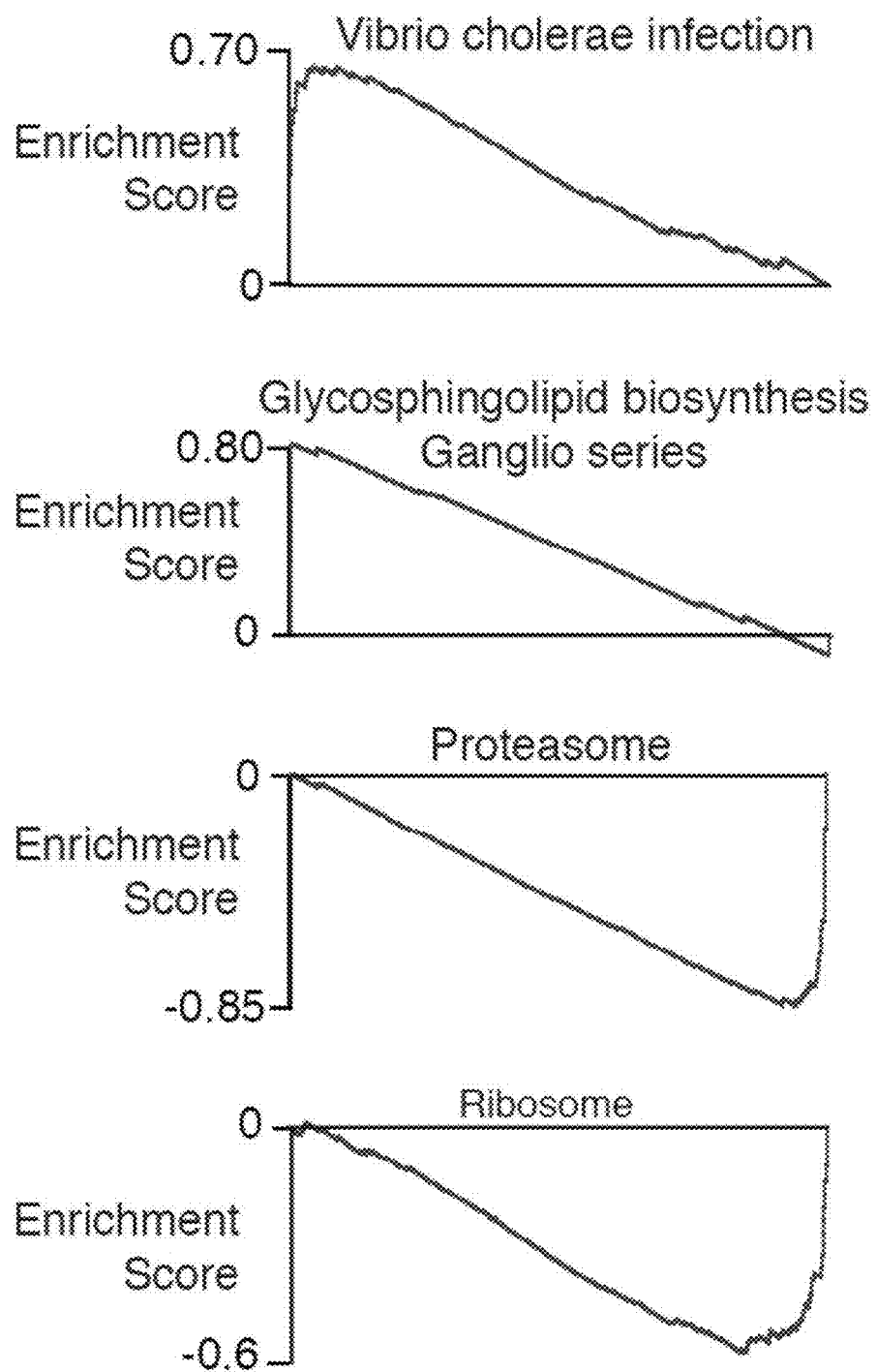

To evaluate the biological validity of the screen, genes were ranked by the average phenotype of their three strongest sgRNAs, and the 50 hits with the strongest protective effect and the 50 hits with the strongest sensitizing effect were defined as "top hits" (all of these are far outside of the range seen with otherwise matched negative control sgRNAs). Gene set enrichment analysis (GSEA) (Pubmed ID: 12808457) revealed that the two most significant KEGG pathways enriched for top protective hit genes were "Infection with *Vibrio cholerae*" and "Glycosphingolipid biosynthesis, ganglio series" (FIG. 6B) consistent with the requirement for the ganglioside receptor for cholera toxin uptake. Among the three KEGG pathways most enriched for top sensitizing genes were "ribosome" and "proteasome" (FIG. 6B). Since the diphtheria toxin catalytic subunit inhibits protein translation, depletion of the ribosome can be expected to sensitize cells to the toxin. Sensitization of cells by knockdown of the proteasome suggests that the proteasome counteracts CTx-DTA toxicity after it enters the cytosol. A similar function for the proteosome in degrading ricin, another retro-translocating toxin, was recently demonstrated (Pubmed ID: 23394947). Taken together, the unbiased GSEA analysis provides support for the high specificity in hit gene identification by our CRISPRi approach.

Figure 6C:
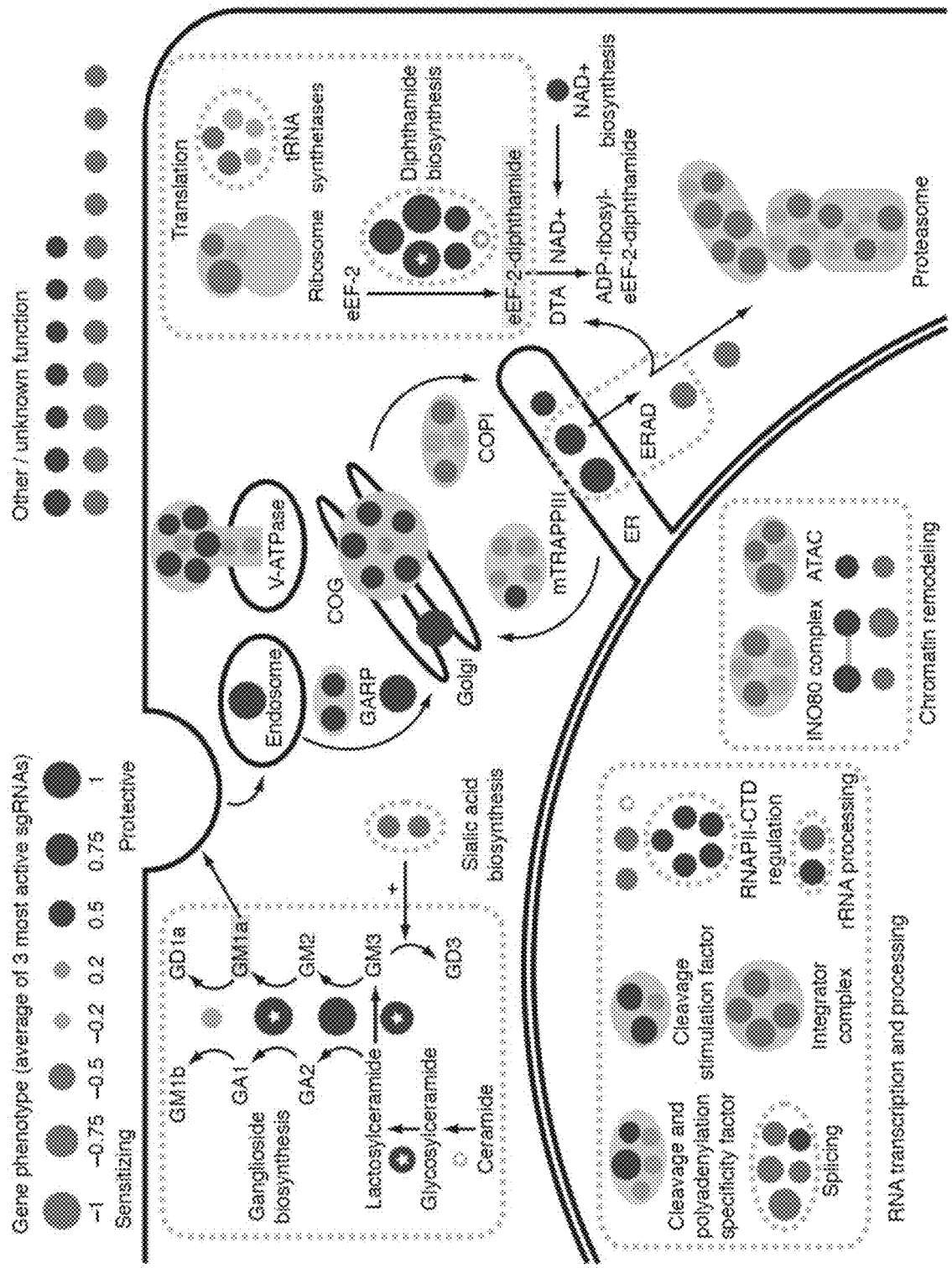
Figure 13B:
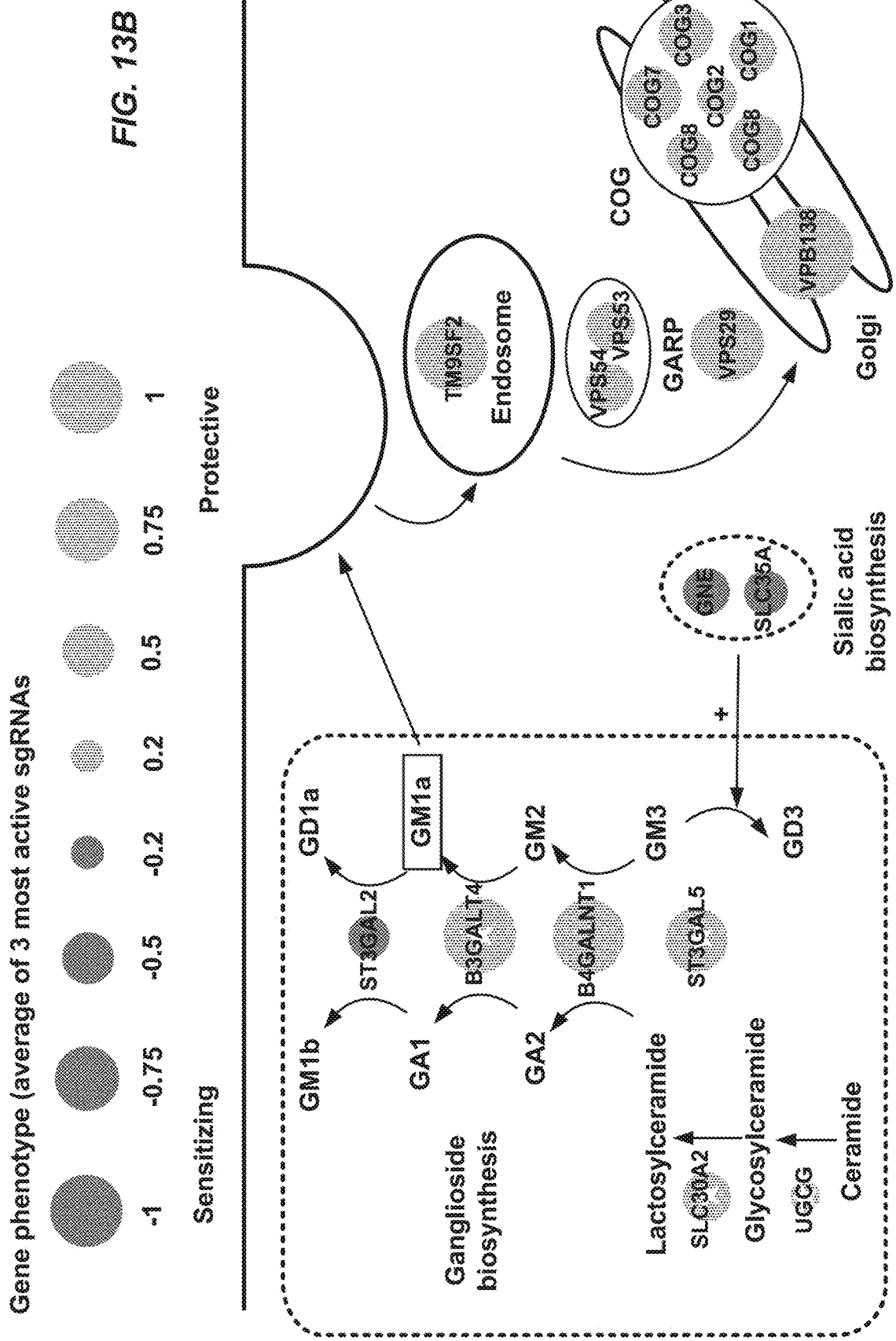
Figure 13C:
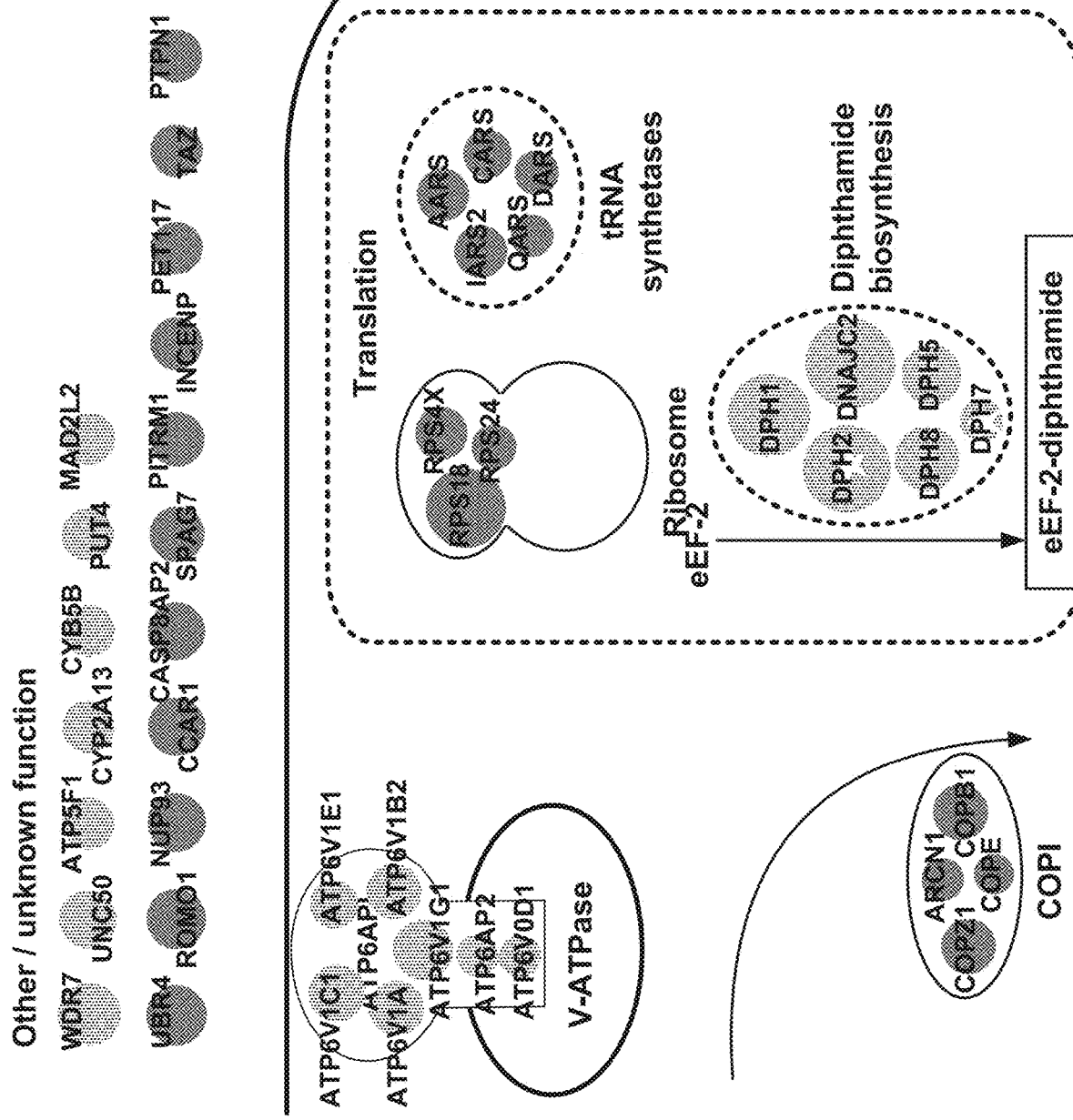
Figure 13D:
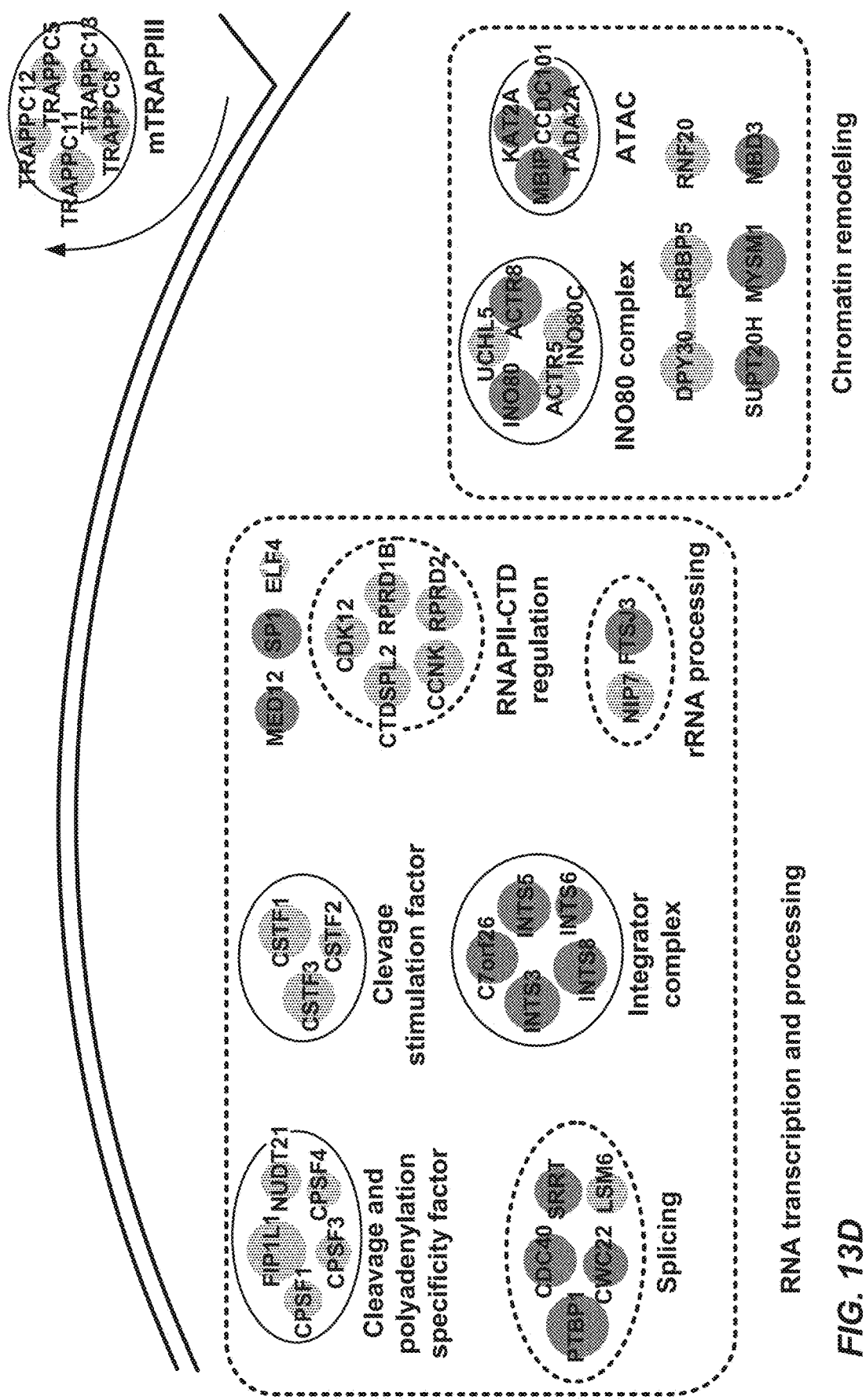
Figure 13E:
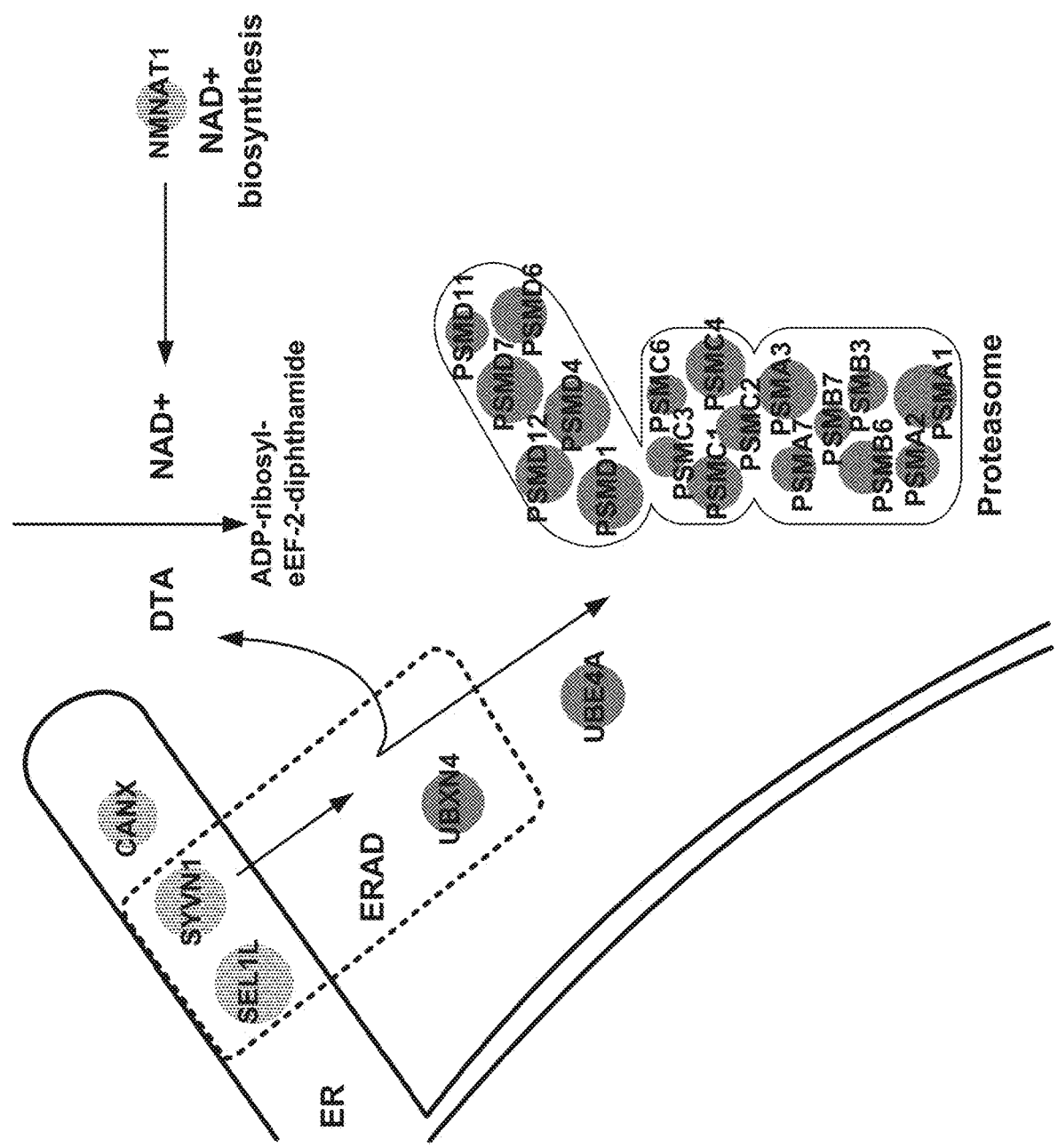

The top hit genes were further characterized by assigning them to cellular pathways and protein complexes according to their previously characterized roles (FIG. 6C and FIG. 13B). The CRISPRi screen identified a protective effect of knockdown for all of the top hits recovered in the previously published haploid mutagenesis screen (denoted with a white star). The two top pathways identified by haploid mutagenesis as modulating cellular sensitivity to CTx-DTA are the diphthamide biosynthesis pathway (required to generate eEF-2-diphthamide, the target of diphtheria toxin) and the ganglioside biosynthesis pathway (required to produce GM1, the cell-surface receptor for cholera toxin). The CRISPRi screen validated the top hits from the haploid mutagenesis screen and identified many additional core components of each pathway. While knockdown of all hits in the diphthamide biosynthesis pathway had a protective effect, the results for ganglioside biosynthesis genes showed a differentiated pattern: knockdown of enzymes involved in the production of GM1a were protective, whereas knockdown of enzymes that catalyze the production of other ganglioside species (including GM1b) was sensitizing. These results argue that GM1a is the relevant cell-surface receptor for CTx-DTA and more broadly illustrate the value of being able to reliably detect both sensitizing and protective genes to dissect biological pathways.

Many of the top hits are components of cellular pathways and protein complexes that were previously identified in targeted biochemical and cell biology experiments to be important for retrograde trafficking and retro-translocation of other toxins such as Ricin and Shiga toxin (Pubmed IDs: 19678899, 23394947). However, it remains unclear how Ctx is trafficked through the Golgi network (Pubmed ID: 22069586). The screen herein revealed a critical role for the COG and GARP complexes in CTx-DTA retrograde transport; targeting of the vast majority of the subunits of these complexes leads to strong resistance. These two complexes tether late endosomes to the trans-golgi network or modulate intra-Golgi retrograde transport (Pubmed ID: 16936697). Retro-translocation of the catalytic chain of CTx has been proposed to be mediated by the ER-associated degradation (ERAD) pathway although this pathway was not identified in previous genetic screens. Consistent with this proposed role for the ERAD machinery, knockdown of members of the ERAD E3 ubiquitin ligase complex, SYVN1 (encoding Hrd1) and SEL1L (the mammalian homolog of yeast Hrd3) rendered cells resistant to CTx-DTA. Factors mediating cytosolic degradation of ERAD substrates (in particular UBXN4, also known as UBXD2/erasin and the proteasome) were sensitizing hits, suggesting that they may reduce cytosolic levels of the catalytic toxin chains in WT cells.

Other top hit genes were tightly clustered in a number of protein complexes involved in gene expression, including the Integrator complex, factors involved in mRNA cleavage and adenylation, and chromatin remodeling. Repression of all canonical components of the cleavage stimulating factor complex and most of the core components of the cleavage and polyadenylation specificity factor complex protected cells from CtxDTA (see below for validation of one of these hit genes). This illustrates the ability of unbiased CRISPRi screens to identify complexes that modulate specific processes with very high saturation. These pathways had not previously been implicated in the control of cholera toxin or diphtheria toxin sensitivity. The ability to robustly identify novel pathways in a process as intensely studied as toxin entry highlights the potential of CRISPRi as a discovery platform.

Figure 7A:
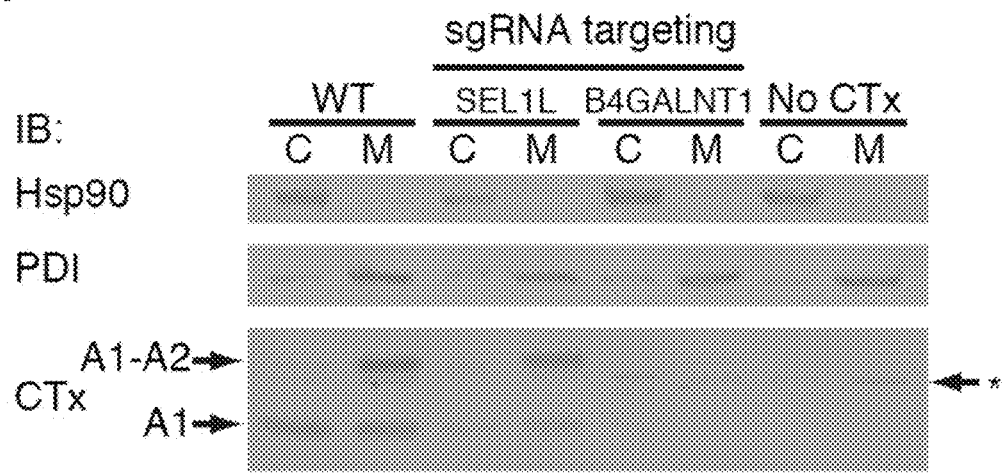
FIG. 7A-FIG. 7G: CRISPRi Strongly Represses Gene Expression Resulting in Robust Reproducible Phenotypes, which Enables Compaction of A Genome Wide Library.
Figure 7B:
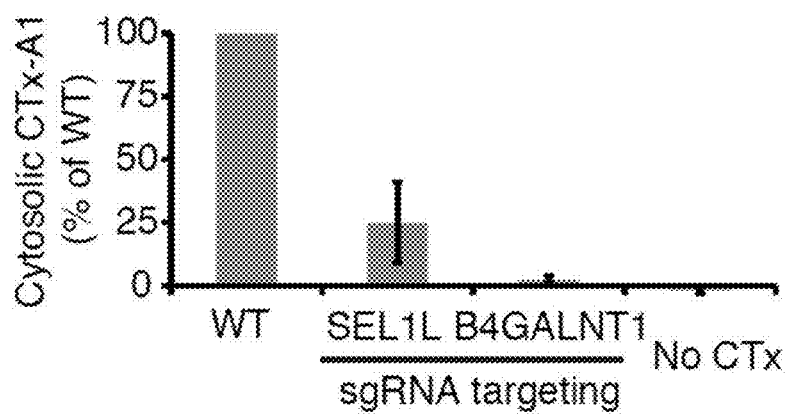
Figure 7C:
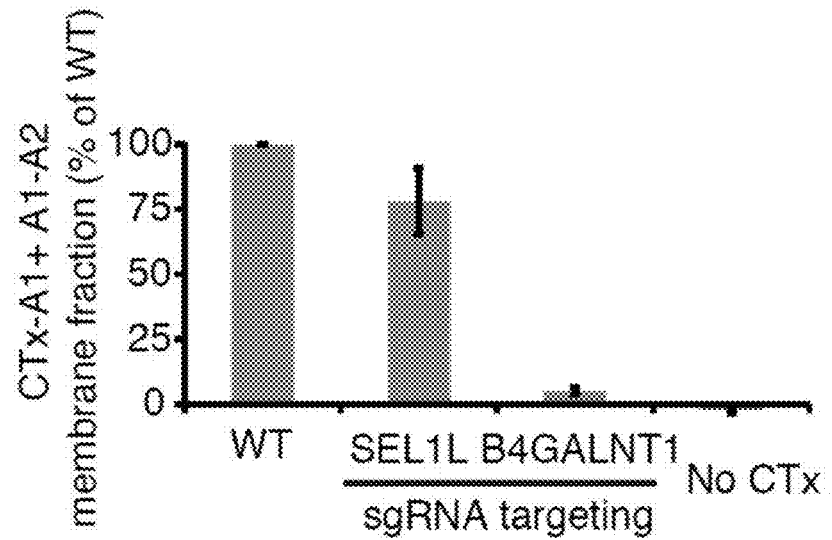

I. Potent Phenotypes and Knockdown Levels Achieved by the Genome-Scale CRISPRi Library To validate the suggested role of the identified ERAD factors in toxin retrotranslocation from the ER to the cytosol, incubated K562 cells were transiently (90 min) transfected with unmodified CTx and the amount of CTx chains in the cytosol and membrane fractions was quantified. SEL1L knockdown resulted in a dramatic reduction of cytosolic CTx-A1, whereas levels in the membrane fraction were much less affected (FIG. 7A-FIG. 7C). By contrast, knockdown of B4GALNT1, an enzyme required for the synthesis of the CTx receptor GM1a, resulted in a nearly complete absence of CTx chains from both the cytosolic and the membrane fraction (FIG. 7A-FIG. 7C). This highly efficient block of CTx binding and uptake by a single sgRNA, which is mirrored by the strong CTx-DTA resistance achieved by B4GALNT1 knockdown (FIG. 7D), underscores the ability of the CRISPRi library described herein to achieve potent loss-of-function phenotypes.

Figure 7D:
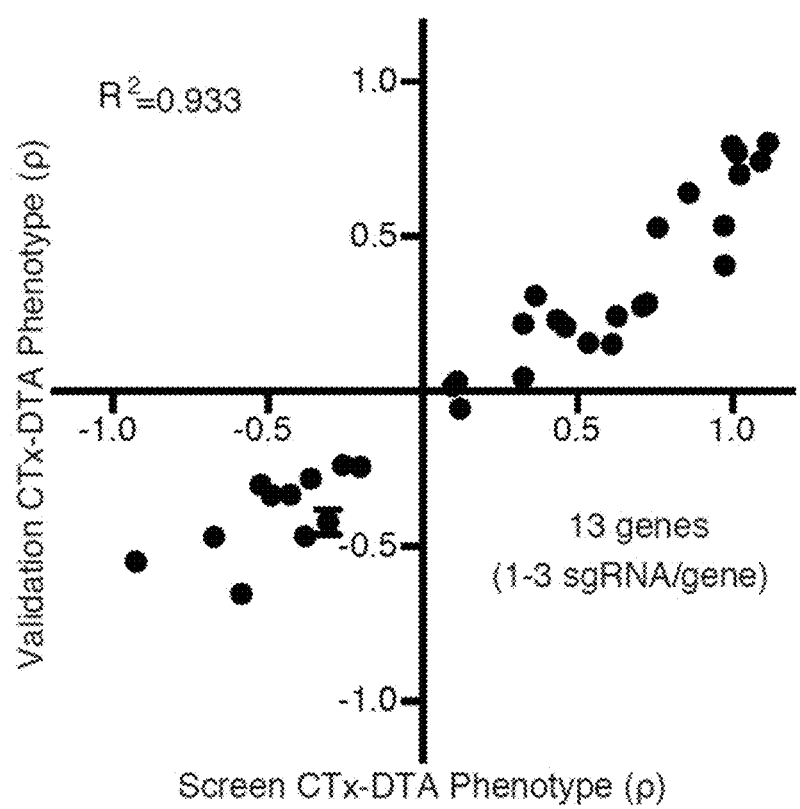
Figure 7E:
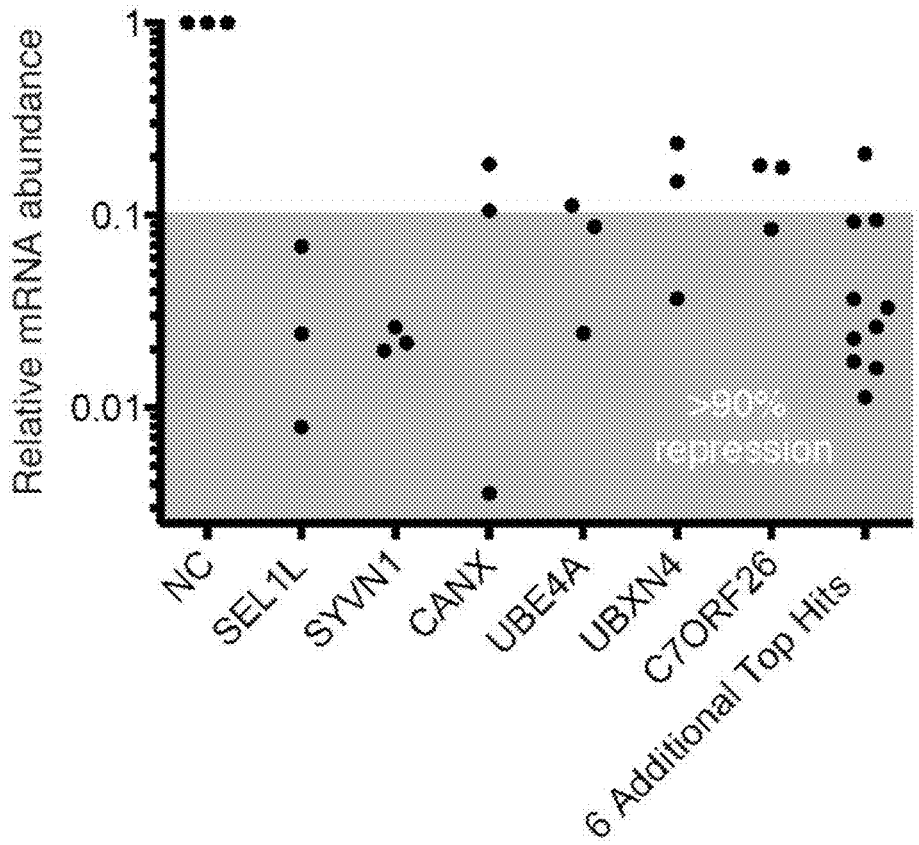

To technically validate the results from this screen sgRNAs which putatively modulate cellular response to CTx-DTA in mechanistically diverse ways were re-tested. For each sgRNA, the ricin phenotypes were quantified as well as the change in abundance of the targeted transcript by qPCR. The re-test experiments were highly correlated with data from the primary screen (FIG. 7D). In the validation experiments across 5 screens and 75 sgRNAs, the activities of 74 out of 75 sgRNAs robustly retested and were highly correlated (R^2=0.879) with the results obtained in the primary screen, demonstrating the reliability of phenotype scores obtained in the primary screens. qPCR data showed robust repression, with 80-99% knockdown for each sgRNA and at least 90% for every gene (FIG. 7E).

J. Refinement of sgRNA Rules Enables More Compact Design of Future CRISPRi Libraries The results of genome-scale CRISPRi for growth and CTx-DTA resistance provided a set of active and inactive sgRNAs for a larger group of genes. These data were used as a training set to discern further rules that would be predictive of sgRNA activity.

Figure 14A:
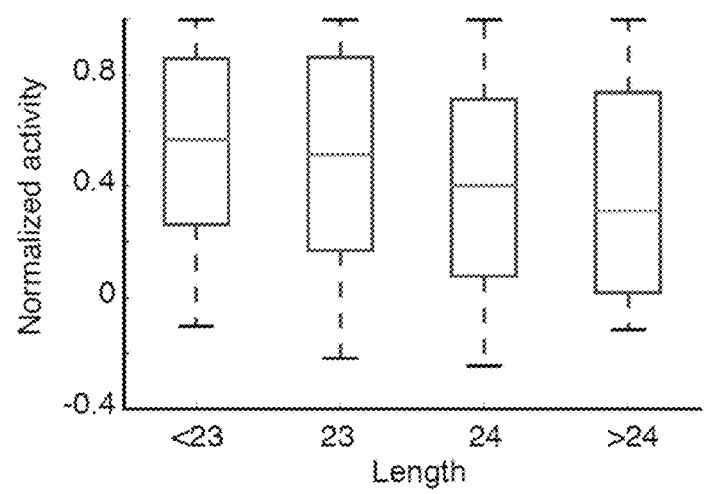
FIG. 14A-FIG. 14E: Exemplary rules for further improving CRISPRi library performance.
Figure 14B:
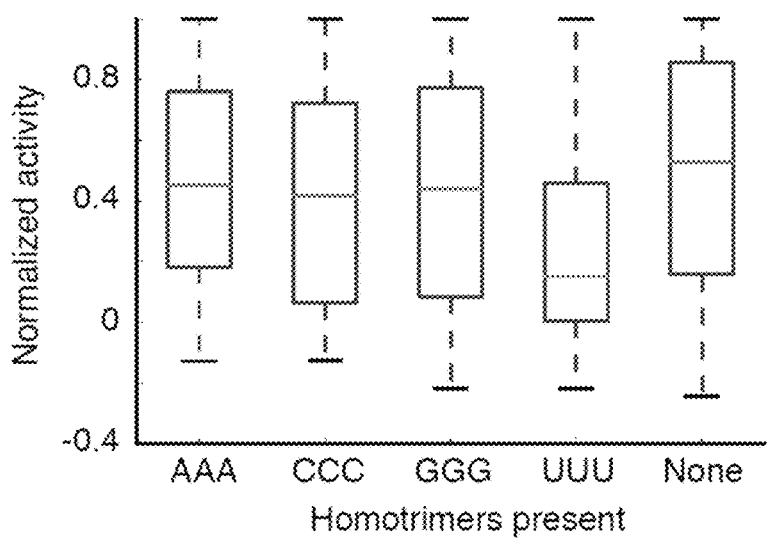
Figure 14C:
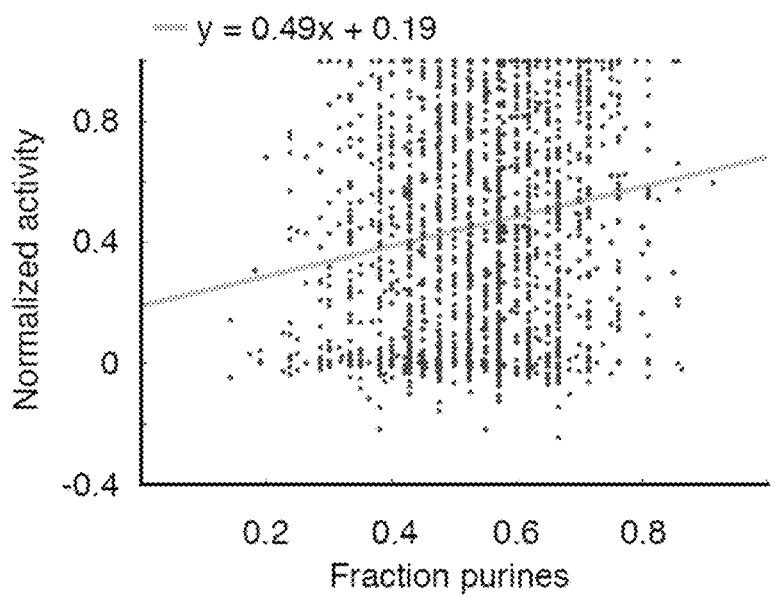
Figure 14D:
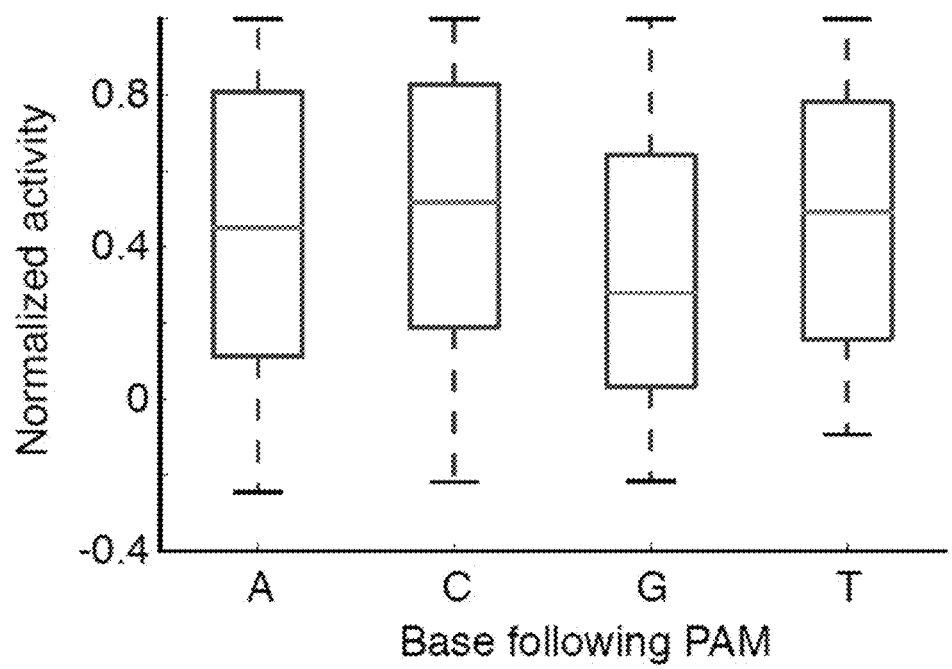
Figure 14E:
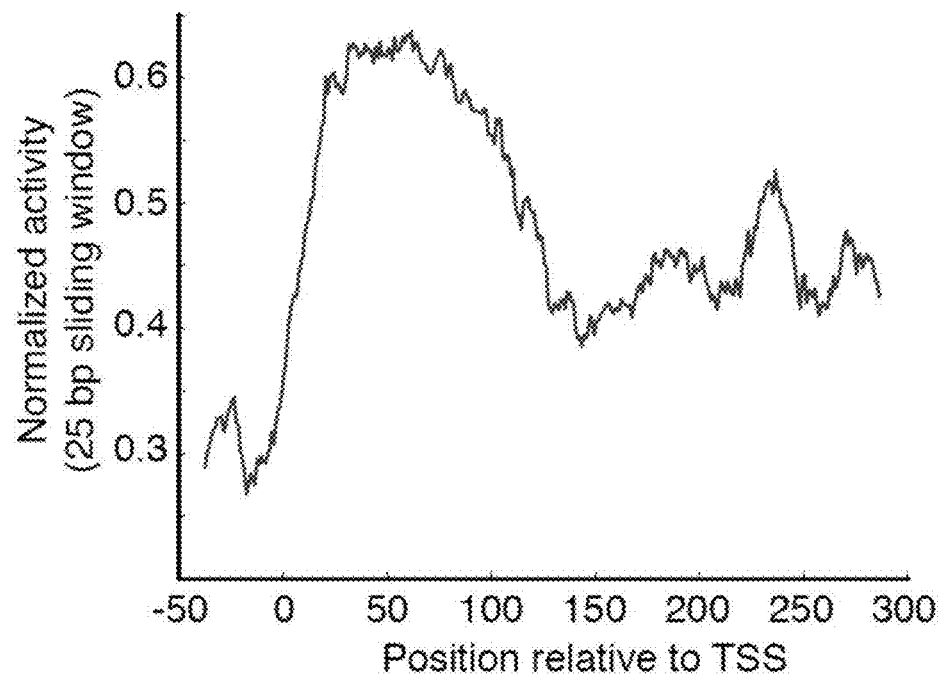

The trend for shorter sgRNAs to show higher activity was confirmed for sgRNAs in the genome-wide library (FIG. 14A). sgRNAs containing the UUU homotrimer resulted in less pronounced phenotypes than other sgRNAs (FIG. 14B). Overall higher purine content was predictive of higher sgRNA activity (FIG. 14C). The negative impact of pyrimidines specifically in the 3' end of the sgRNA that had been previously reported (Pubmed ID: 24336569) was not observed. Decreased activity for sgRNAs targeting genomic sites in which the PAM (NGG) was followed by a G was observed (FIG. 14D). Finally, a metagene analysis revealed maximum sgRNA activity in a window of +25 to +100 bp downstream of the TSS (FIG. 14E), consistent with earlier observations (FIG. 11B).

Figure 7F:
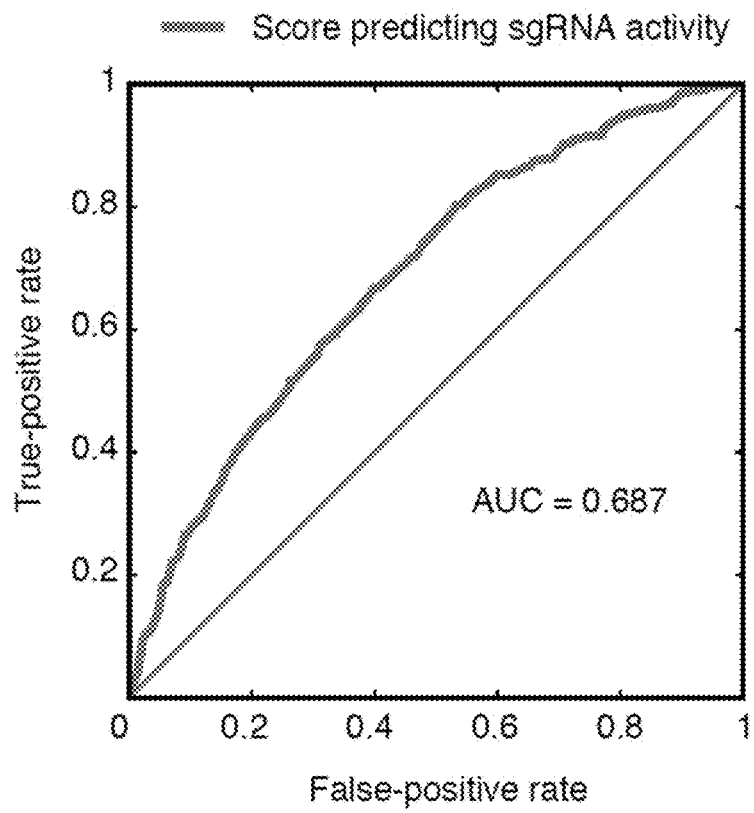
Figure 7G:
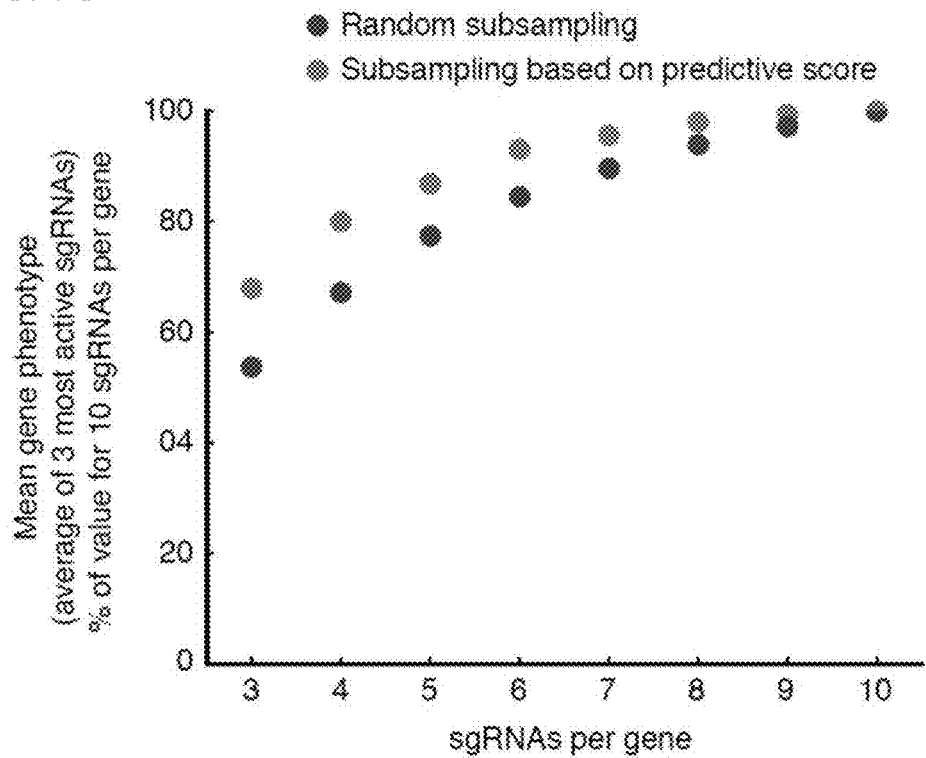
Figure 16B:
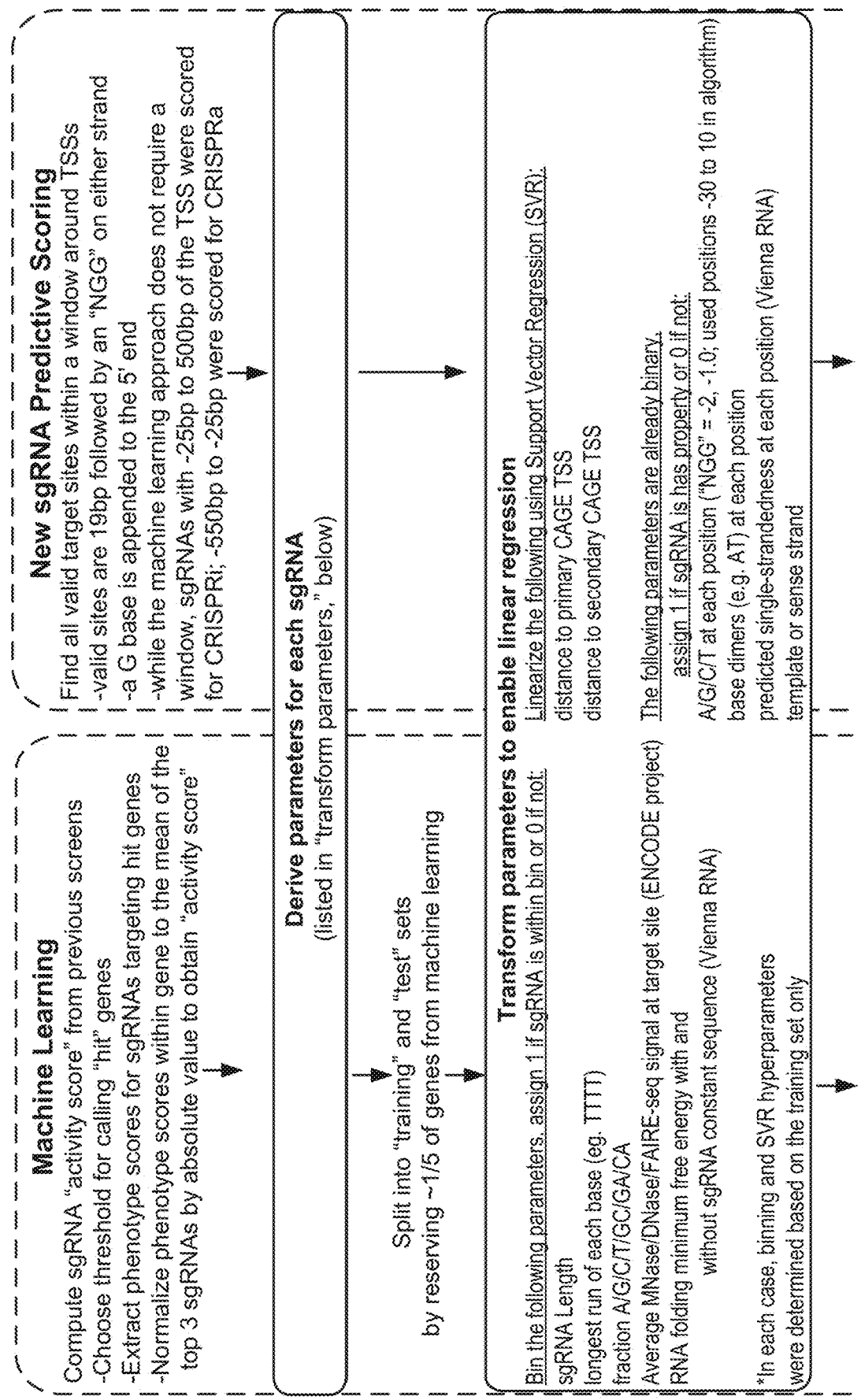
Figure 16C:
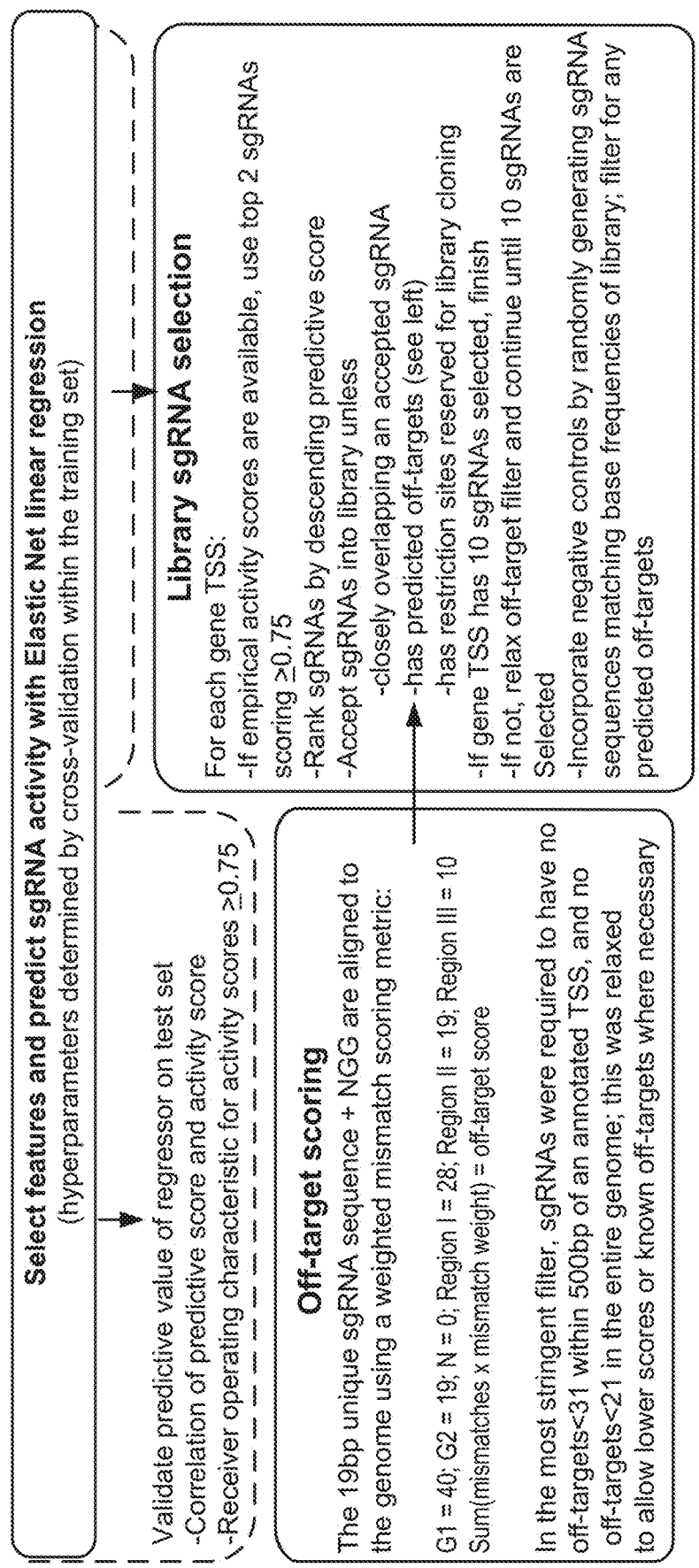

Using stepwise logistic regression, these rules were integrated into a quantitative score that predicted sgRNA activity with an ROC area under the curve of 0.687 (FIG. 7F, see Materials and Methods for details). To validate the hypothesis that this predictive score will enable the design of potent, compact CRISPRi libraries in the future, phenotypes from two genome-scale CRISPRi screens were computationally subsampled by either choosing random subsets of sgRNAs for each gene, or selecting subsets based on the refined algorithm (FIGS. 16A-16C). By selecting 6 out of 10 sgRNAs per gene based on the predictive score, >93% of the library activity, as quantified by the metric used to identify hit genes in the screens (average phenotype of the strongest 3 sgRNAs per gene) was maintained. Compaction of the genome-scale CRISPRi library by 40% further facilitates pooled screens by reducing the scale of the cell populations and the number of sequencing reads required for analysis.

IV. Discussion

CRISPRi and CRISPRa is established herein as robust methods for systematically turning on and off transcription of endogenous genes in human cells. CRISPRi/a can be used to screen for both loss-of-function and gain-of-function phenotypes rapidly in a pooled format. Thus known and unexpected genes required for growth or which modulate sensitivity to a toxin (CTx-DTA) can be identified. An allelic series of gene expression spanning a broad range, from ~100-fold repression to ~10-fold induction can also be created to examine and define how the abundance of a protein relates to function.

The experiments described herein demonstrate that a key feature of CRISPRi is the very low incidence of off-target effects, as evidenced by the near-absence of activity for three large and distinct classes of negative control sgRNAs in the genome-scale CRISPRi library. This feature simplifies validation and interpretation of screening results. The observed specificity stems from two distinct properties of the system. First, CRISPRi/a complexes bound outside a narrow window around the TSS largely fail to modulate transcription; this dramatically shrinks the sequence space across the genome where off-target binding will produce significant off-target activity. Additionally, CRISPRi activity is highly sensitive to mismatches between the sgRNA and target DNA suggesting that off-target binding seen in Chip-Seq experiments (Pubmed IDs: 24752079, 24837660, 24980957) is too transient to impact transcription. The combination of strict sequence requirements and positional rules renders CRISPRi activity exquisitely specific.

A current implementation of CRISPRa described herein uses the sunCas9 fusion protein to recruit multiple copies of one activation domain to directly engage basal transcription machinery. Many copies of a single or multiple effector domains can be recruited using similar approaches to create highly active artificial enhancers or silenced heterochromatin to modulate gene expression over an even broader range. The pooled phenotype-based screening approach provides a tool for the evaluation of on- and off-target activities of future variations on CRISPRi and CRISPRa.

CRISPRa screening provides a new approach for exploring the diversity of transcripts across complex genomes. Classically, gene activation has been used to dissect the limiting component of a biochemical process (Pubmed ID: 22419077). For example, overexpression screens have been used to identify the molecular target of a drug or to activate key rate-limiting steps in a pathway. Two early examples of such screens in eukaryotic cells are the identification of DPAGT1 as the target of tunicamycin and MyoD as the limiting component of fibroblast to myoblast differentiation (Pubmed IDs: 6316322, 3690668). More recently, a combinatorial activation screen identified four genes that when co-expressed reprogram fibroblasts into pluripotent stem cells (Pubmed ID: 16904174). CRISPRa should greatly accelerate similar searches for combinations of factors with emergent properties. In addition, CRISPRa will likely provide insight into cellular pathways where redundancy hampers loss of function genetic approaches. Allelic series of sgRNAs that quantitatively activate and repress gene expression may also provide deeper understanding of how genetic polymorphisms, copy number variation or mutations outside the exome contribute to disease susceptibility (Pubmed ID: 17597780).

The ability to control transcription with high specificity provided herein simplifies the analysis and validation of high-throughput screening data. The genome-scale CRISPRi library described herein contains 10sgRNAs/TSS; the resulting library size allows it to be screened in a cell population grown in a single spinner flask. However, the observed high specificity, and further understanding of rules governing sgRNA activity should enable the creation of more compact sgRNA libraries. By compacting the genome-wide libraries, larger numbers of cell lines, chemical compounds, time points or reporter constructs can be screened. Alternately, an sgRNA library designed to activate or repress a broader range of transcripts in the human genome can reveal the function of many non-canonical RNAs encoded in the human genome. As most non-coding transcripts are nuclear and lack an open reading frame, methods that directly modulate transcription are optimally suited for interrogating the function of these RNAs (Pubmed ID: 22955988).

Systematic genetic interaction (GI) maps have proven to be powerful tools for revealing gene functions within pathways or complexes (Pubmed IDs: 23394947, 14764870, 16487579, 20093466, 16269340, 17314980, 17510664, 24906158). A CRISPRa GI map or a combined CRISPRi/a GI map could yield rich novel biology elucidating how networks of proteins dictate cellular function (Pubmed ID: 21572441). More generally, quantitative methods of turning on and off one or multiple transcripts represents a critical tool for understanding how expression of the genes encoded in our genomes controls cell function and fate.

V. Methods

A. Plasmid Design and Construction

Previously described vectors were used to express dCas9, dCas9-KRAB and the sunCas9 CRISPRa system. Using Gibson cloning an optimized CRISPRi fusion protein was cloned. The protein is expressed from the inducible TRE3G promoter (Clontech) in a pHR lentiviral backbone (Addgene). Using this vector, an mRNA molecule encoding the CRISPRi fusion protein and mCherry separated by a viral T2A sequence was expressed. The CRISPRi fusion encodes mammalian codon optimized *Streptococcus pyogenes* dCas9 (DNA 2.0) fused at the N-terminus with the Kox1 KRAB domain and at the C-terminus with two SV40 nuclear localization sequences (NLS). To generate a Cas9 expression plasmid matched to a lentiviral dCas9-BFP fusion construct, residues 10 and 840 were reverted from alanine to aspartic acid and histidine using standard quick change mutagenesis (Agilent). The optimized sgRNA was previously described (Pubmed ID: 24360272). Briefly, the sgRNA was expressed using a lentiviral U6 based expression vector derived from pSico which co-expresses either BFP, GFP or mCherry and a puromycin resistance cassette separated by a T2A sequence from either the CMV or Ef1 Alpha promoter. The sgRNA constant region was modified to clone the genome scale CRISPRi library by altering one base pair in the sgRNA stem sequence that introduces a Blp1 restriction site. This change does not diminish sgRNA activity as tested using a GFP reporter as previously described (Data not shown) (Pubmed ID: 23849981). The sgRNA expression plasmids for validation experiments were cloned by PCR from an existing sgRNA template using a common 3' primer and a unique 5' primer containing the desired protospacer. The PCR product and the lentiviral U6 based expression vector were digested with BstXI and XhoI and the two pieces of DNA were ligated together.

B. CRISPRi TSS Library Specifications

Genes were selected from the entire set of protein coding genes. A subset of Unassigned genes and Membrane_Protein not likely to be expressed in most cells and with a RPKM of 0 in a K562 RNA-seq expression data were excluded. The final targeted gene total was 15,977. Transcription start sites were selected from GencodeV19/Ensembl release 74 transcripts, selecting all transcripts annotated by the appris pipeline when possible, or all transcripts of the same biotype ('protein_coding', 'processed_transcript', etc) as the corresponding gene. In all cases only 'KNOWN' or 'NOVEL' transcripts were used, unless none existed or the gene itself was 'PUTATIVE'. Where no transcripts matching this criteria were found, all Refseq (accessed Nov. 19, 2013) transcripts with NM accession numbers were used.

For 50 bp upstream and 300 bp downstream of each TSS, every guide adjacent to an NGG PAM, starting with a G, and having length 18-25 was computed. Guides were scored by uniqueness in the genome, as determined by an empirically derived (and CRISPRicin-verified) scoring metric: PAM G1=40, PAM G2=19, PAM N=0, Region I=28, Region II=19, Region III=10. If sum(mismatches*mismatch-score) <threshold, the mismatched site is considered an off-target. The threshold was systematically lowered to allow less unique guides to be considered where necessary. In some cases, threshold was held stringent and the number of allowed targets was increased to tolerate very similar gene families Each guide ID was given a uniqueness string corresponding to threshold (e flag of bowtie) and allowed targets (m flag). In decreasing order of stringency: e39m1, e30m1, e20m1, e11m1, e1m1, e39m2, e39m3, fail For each gene, a minimum of 10 guides were selected. The script attempted to target each TSS with 10 guides (with individual guides counted toward multiple TSSs where applicable), although in cases where this led to >25 guides for a gene, the script then defaulted to requiring only at least 3 guides for each TSS. Guides were ranked as follows: 1. uniqueness according to off-target score, 2. the number of TSSs the guide is in range to target (high to low), 3. the number genes the guide targets (low to high; for the vast majority of guides this was 1, but in cases guides were close to 2 genes those guides were avoided), 4. guides of length 18-21 were considered 'short' and ranked first, while guides of length 22-25 were considered 'long' and ranked according to their length (low to high), 5. a random ranking was applied to choose among guides equivalent in criteria 1-4. Guides were not selected if they are separated from another accepted guide by fewer than 5 bases as defined by the 'left side' of the sequence (5' end for +strand oligos, 3' end for −strand). Only ~40 genes did not completely meet this standard.

As GC content increases at transcription start sites and sgRNA placement depends on the 3' NGG motif, the sgRNA set was particularly enriched for sgRNAs in this region. To buffer against incorrectly annotated transcription start sites sgRNAs were picked for the genome wide library in a window from −50 to +350 bp relative to the transcription start site of each gene. This window is broader than the absolute maximum peak of CRISPRi activity from +50 to +100 but safeguards against closely spaced alternate TSS or incorrectly annotated TSS.

Negative control guides were designed on randomized human essential gene TSS regions and afterwards selected using the same rules as above.

Exemplary CRISPR target sequences identified using one or more of the rules described herein for activation or repression are provided in the co-filed sequence listing as Table 2 for human CRSPRa sgRNA targets, Table 3 for human CRISPRi sgRNA targets and Table 4 for mouse CRISPRi sgRNA targets.

C. CRISPRi/a Library Cloning

CRISPRi/a libraries were prepared by methods similar to those previously described for shRNA libraries (Pubmed IDs: 19448642, 24992097). Complex oligonucleotide pools were synthesized by Agilent or Custom Array. Each library was amplified by PCR, digested with either BstX1 and XhoI or BstX1 and Blp1 and cloned into an sgRNA expression vector.

D. Cell Culture, DNA Transfections, and Viral Production and Construction of CRISPRi/a Cell Lines HEK293 cells were maintained in Dulbecco's modified eagle medium (DMEM) in 10% FBS, 2 mM glutamine, 100 units/mL streptomycin and 100 μg/mL penicillin. K562 cells were grown in RPMI-1640 with 25 mM HEPES and 2.0 g/L NaHCo3 in 10% FBS, 2 mM glutamine, 100 units/mL streptomycin and 100 μg/mL penicillin. Lentivirus was produced by transfecting HEK293 with standard packaging vectors using TransIT®-LTI Transfection Reagent (Mirus, MIR 2306). Viral supernatant was harvested 72 hours following transfection and filtered through a 0.45 μm PVDF syringe filter.

To construct CRISPRi/a cell lines, K562 cells were lentivirally transduced to express Cas9, dCas9, dCas9-KRAB, scFV-sfGFP-VP64 or the rtTA from the SFFV promoter, or dCas9-GCN4-10× from the TRE3G promoter. Pure polyclonal populations of each CRISPRi/a cell line were sorted by flow cytometry using a BD FACS Aria2 for stable GFP, BFP or mCherry expression. For CRISPRa, single cell clones were then isolated and analyzed as described previously.

To construct the inducible CRISPRi K562 cell line, a clonal K562 cell line that constitutively expresses a standard doxycycline inducible transactivator was generated without a selection marker by lentiviral transduction and identified using western blot analysis. These cells were then transduced with an inducible KRAB-dCas9 fusion protein marked by P2A-mCherry (pHR-Tre3G-KRAB-dCas9-P2A-mCherry). Doxycycline was added following infection and flow cytometry was used to sort cells that expressed mCherry. These cells were then grown in the absence of doxcycycline until mCherry returned to uninduced levels.

E. High Throughput Pooled CRISPRi/a Screening

CRISPRi/a K562 cell lines were infected with sgRNA libraries as previously described (Pubmed ID: 23394947). The infection was scaled to achieve a multiplicity of infection of one sgRNA per cell. Two days after infection, cells were selected with 0.65-0.75 μg/mL puromycin (Tocris) for 3 days, and then washed into fresh medium for ~24-48 hour recovery. Each growth or toxin screen was carried out until untreated cells had undergone 12 population doublings and we achieved at least 6 population doublings difference between untreated and toxin treated cells. For the CRISPRi/a tiling ricin screens, cells were passaged or treated with 3 or 4 pulses of 0.5 ng/mL ricin over 16 days. For the CRISPRi genome-scale growth and CTx-DTA screen, cells were passaged or treated with two pulses of 0.4 nM CTx-DTA over 10 days. For both toxins, we spun cells out of the toxin at 24 hours and re-suspended cells in fresh media. Cells were maintained at a density of between 500,000 and 1,000,000 cells/mL continually maintaining a library coverage of at least 1000 cells per sgRNA. Cells were collected for genomic DNA extraction immediately populations of cells expressing this library of sgRNAs were either harvested at the outset of the experiment (the t0 time point), grown under standard conditions (untreated), or treated with toxin. Genomic DNA was harvested from all samples; the sgRNA-encoding regions were then amplified by PCR and sequenced on an Illumina HiSeq-2500 using custom primers with previously described protocols at high coverage. Two biological replicates of each screen were performed. From this data, the frequencies of cells expressing different sgRNAs were quantified in each sample. From this data the phenotype of each sgRNA, which was previously defined for growth ("gamma") or resistance to treatment ("rho") was quantified. To calculate a normalized z-score for these phenotypes, gamma or rho were divided by the standard deviation of negative-control sgRNA phenotypes.

F. Bioinformatic Analysis of Hit Genes

Hit genes were ranked based on average phenotype of the 3 most extreme sgRNAs targeting them. Pathways and gene sets enriched among hit genes were identified using GSEA and DAVID software. In the sgRNA tiling experiment it was observed that half of the sgRNAs in the window of maximum activity had a Z-score over 2 suggesting the large majority genes have three active or more active sgRNAs in the CRISPRi library. The genome scale data was analyzed using the metric of average phenotype of the top 3 sgRNAs. Using more sgRNAs can dilute the signal with inactive sgRNA whereas using fewer could fail to take advantage of the full set of active sgRNAs. Statistical significance of the average phenotype can then be evaluated based on clear differentiation from the signal seen for non targeting control sgRNAs.

G. Individual Re-Test of sgRNA Phenotypes and CRISPRi/a Transcript Repression and Activation Individual phenotype re-test experiments for sgRNAs from the CRISPRi/a ricin tiling screens, the CRISPRi genome scale cholera screens, and sub-library screen of essential genes were performed as competitive growth experiments on a partially transduced populations of K562 cells. Briefly, cells were partially transduced ~25-60%. Three or four days following infection, cells were counted and seeded in 24 well plates at 0.25-0.5 million cells/mL. Triplicate samples for each sgRNA were grown under standard conditions or, for toxin challenge experiments, were treated with 0.5 ng/mL of ricin or 0.4 nM CTx-DTA. Each population of cells was allowed to grow or recover for 6 days. For both toxins, cells were spun cells out of the toxin at 24 hours and re-suspended cells in fresh media. The absolute cell number and percentage of cells that express BFP (indicating sgRNA expression) was measured for each sample at the beginning and end of the experiment. Rho scores were calculated as described. For cell proliferation re-test experiments, cells were grown under standard conditions in the presence and absence of doxycycline. Doxycycline concentration was daily adjusted to 50 ng/mL assuming a half-life of 24 hours. Relative cell proliferation was determined by the percentage of cells that maintained expression of mCherry (as a surrogate for induced KRAB-dCas9) and BFP (indicating sgRNA expression).

To determine the amount of gene knockdown or activation for individual sgRNAs, partially transduced cells expressing individual sgRNAs, which were used for re-test experiments, were selected with a maximum of 3 ug/mL puromycin for 4-5 days. Cells were allowed to recover from selection and then were harvested for RT-qPCR directly or were treated with doxycycline (to induced KRAB-dCas9) prior to collection.

H. Negative Selection Screening of Essential Gene Sub-Library

Lentivirus was prepared by cotransfection of library plasmid DNA with lentiviral packaging vectors (expressing Gag, Pol, Rev, and Tat) into 293T cells using TransIT®-LTI Transfection Reagent (Mirus, MIR 2306). Media was changed the following day. Viral supernatant was harvested the second day post transfection, filtered through a 0.45 µm PVDF syringe filter, and processed for storage at −80° C. in two ways: (screen replicate 1) direct flash freezing in liquid nitrogen, (screen replicate 2) concentration using Alstem Precipitation Solution (Alstem, VC100), according to manufacturer instructions, followed by treatment with 50 U/mL Benzonase Nuclease (Sigma, E1014-25KU) for 30 minutes at 37° C. prior to flash freezing.

Inducible KRAB-dCas9 K562 cells were infected with screen virus as previously described (Pubmed ID: 23394947). The infection was scaled to achieve a target multiplicity of infection of (% infection) at representation of the 5776-element sub-library. Two days after infection, cells were selected with 0.65 µg/mL PURO for 3 days, and then washed into fresh medium for ~24 hour recovery. Cells were grown for 13 days, maintained at a density of ~500,000 to 1,000,000 cells/mL with a representation of >1,000-fold, in the presence or absence of doxycycline. Throughout the screen doxycycline was daily adjusted to 50 ng/mL assuming a half-life of 24 hours. Cells were collected for genomic DNA extraction immediately prior to doxycycline addition and again 13 days later. Replicate infections were screened in duplicate, and data from these duplicate end points were averaged.

I. Quantitative RT-PCR

Cells were harvested and total RNA was isolated using the NucleoSpin RNA II (Macherey-Nagel), according to manufacturer's instructions. RNA was converted to cDNA using AMV reverse transcriptase under standard conditions with oligo dT primers and RNasin (Promega). Quantitative PCR reactions were prepared with a 2× master mix according to the manufacturer's instructions (Quanta Biosciences). Reactions were run on a LightCycler thermal cycler (Roche).

J. Western Blot

Cells were lysed in TBS (20 mM Tris, 150 mM NaCl) supplemented with 0.5% Igepal, 1× protease inhibitor (Roche), and 500 U/mL Benzonase Nuclease (Sigma, E1014-25KU). Whole cell lysates were run on a pre-cast 4-12% Bis-Tris polyacrylamide gel (Life Technologies) under denaturing conditions and transferred to PVDF membrane. Antibodies against human influenza hemagglutinin (HA) and alpha-Tubulin (Sigma, T5168) were used to detect proteins. Blots were imaged using the LI-COR Odyssey Imaging System.

K. Cholera Toxin Uptake and Retrotranslocation Assay

A previously described assay (Pubmed ID: 18094046) was adapted. Briefly, aliquots of 2 million K562 cells expressing dCas9-KRAB and sgRNAs targeting genes of interest were resuspended in 3 ml Hank's Balanced Salt Solution (HBSS) and 10 nM CTx (Millipore, 227036) was added. Cells were incubated with the toxin for 90 min at 37° C. After 3 washes in HBSS, cells were lysed in HCN buffer (50 mM HEPES, pH 7.5, 150 mM NaCl, 2 mM CaCl2, and 10 mM N-ethyl maleimide [NEM], and protease inhibitors) containing 0.02% digitonin. After incubation on ice for 10 mM, lysates were subjected to centrifugation (16,000 g for 10 min at 4° C.). The supernatant was removed and represents the cytosolic fraction. The pellet was washed once in PBS and then resuspended in RIPA buffer (150 mM NaCl, 1% Triton X-100, 0.5% sodium deoxycholate, 0.1% SDS, 50 mM Tris-HCl pH 8.0, protease inhibitors). After incubation on ice for 10 min, the samples were subjected to centrifugation. (16,000 g for 10 min at 4° C.). The supernatant was removed and represents the membrane fraction. The cytosolic and membrane fractions were subjected to non-reducing SDS-PAGE and Western Blotting. CTx chains were detected using a polyclonal anti-CTx antibody (Abcam ab123129). As fractionation controls and for normalization of samples, the following antibodies were used: anti-PDI (Santa Cruz Biotechnology, sc-20132) for normalization of membrane fraction signal, and anti-Hsp90 (One World Lab ADI-SPA-846-D) for normalization of cytosolic fraction signal.

L. Machine Learning

Figure 15:
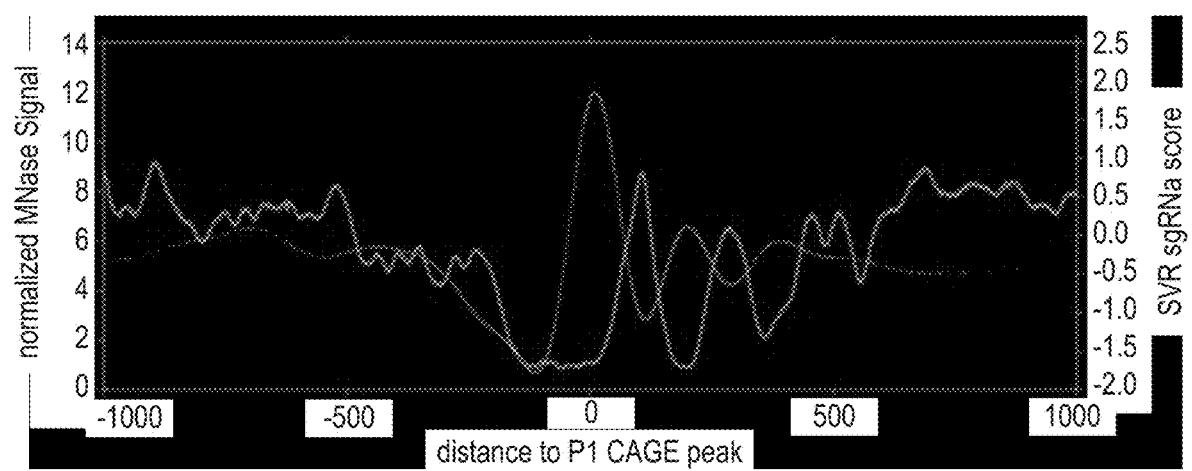
FIG. 15: Depicts sgRNA activity and micrococcal nuclease (MNase-seq) signal as a function of distance to the transcription start site (TSS) as indicated by FANTOM CAGE data. sgRNA activity (light line; arbitrary units) was generated by fitting a Support Vector Regressor to sgRNA phenotypes in genome-wide screens. MNase-seq signal (dark line) for K562 was obtained from the ENCODE project and was normalized and summed over 50 representative genes.

Defined sets of bona fide hit genes were identified for the CRISPRi growth and CTx-DTA sensitivity screens. For each of these genes, sgRNA phenotypes were normalized by dividing each by the phenotype of the strongest sgRNA. A variety of sgRNA features were then investigated for whether the feature was correlated with higher (or lower) sgRNA activity. To combine relevant features into a single quantitative score predictive of sgRNA activity, a forward stepwise logistic regression, in which an sgRNA with a normalized phenotype of 0.75 or greater was classified as active, was used. The final score was incorporated the following features positively correlated with sgRNA activity: shorter length of the sgRNA, fraction purines in the sgRNA, sgRNA targeting the region +25 bp to +100 bp relative to the TSS, absence of UUU homotrimers in the sgRNA, the base following the PAM in the genomic DNA is not a G. An alternative method for library design and/or sgRNA target identification incorporates micrococcal nuclease signal information. sgRNAs targeted to regions having low micrococcal nuclease signal are predicted to have a higher activity than sgRNAs targeted to regions having a high micrococcal nuclease signal. See, FIG. 15. An alternative method for predicting sgRNA activity that utilizes both machine learning and empirical activity data, and incorporates additional features positively correlated with sgRNA activity, is depicted in FIGS. 16A-16C.

Machine learning and empirical validation are utilized to predict the following highly active sgRNA binding region encoding sequences: SEQ ID NOs:26-205,305 are predicted to encode sgRNA binding regions that provide highly active CRISPRi targeting of human genomic loci; SEQ ID NOs:

205,306-410,595 are predicted to encode sgRNA binding regions that provide highly active CRISPRa targeting of human genomic loci; SEQ ID NOs:410,596-633,445 are predicted to encode sgRNA binding regions that provide highly active CRISPRi targeting of mouse genomic loci; SEQ ID NOs:633,446-857,995 are predicted to encode sgRNA binding regions that provide highly active CRISPRa targeting of mouse genomic loci. In some cases, sgRNAs predicted to be highly active in inhibiting or activating a target locus comprise binding regions comprising or consisting of the 19 nucleotides at the 3' end of any one of SEQ ID NOs:26-857,995. A library of such highly active sgRNAs, or a subset or combination thereof, can be constructed by or utilized in the methods described herein.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11254933B2). An electronic copy of the "Sequence Listing" will also be available from the USPTO upon request and payment of the fee set forth in 37 CFR 1.19(b)(3).

What is claimed is:

1. A method of screening for one or more genes that modulate a phenotype, the method comprising:
    contacting a plurality of cells with a library of structurally distinct small guide RNAs (sgRNAs) that target at least $10^4$ genes, thereby generating a plurality of test cells, the plurality of test cells each comprising:
        a small guide RNA (sgRNA); and
        a nuclease deficient sgRNA-mediated nuclease (dCas9) that recognizes a PAM site having the sequence NGG,
    wherein the dCas9 comprises
        a dCas9 domain fused to a transcriptional modulator;
    selecting the test cells on the basis of the phenotype;
    quantitating a frequency of the structurally distinct sgRNAs within the population of selected test cells, wherein the sgRNAs that target the at least $10^4$ genes that modulate the phenotype are overrepresented or underrepresented in the selected test cells, wherein:
    i) the sgRNAs that target the genes are overrepresented or underrepresented within the selected test cells relative to the frequency of the corresponding sgRNAs in the sgRNA library; or
    ii) the method further comprises contacting a plurality of control cells with the sgRNA library, wherein the plurality of control cells are not subject to the selecting on the basis of the phenotype, and the sgRNAs that target the genes are overrepresented or underrepresented in the selected test cells relative to a corresponding frequency in the plurality of control cells; or
    iii) wherein the sgRNAs that target the genes are overrepresented or underrepresented in the selected test cells relative to the corresponding frequency in the test cells at an earlier time point in a culturing of the test cells;
    wherein at least a majority of the library of structurally distinct sgRNAs are targeted to a region between −50 to +350 relative to a transcription start site of the targeted genes if the transcriptional modulator is a transcriptional repressor; and −400 to −50 bp relative to the transcription start site of the targeted genes if the transcriptional modulator is a transcriptional activator;
    wherein a majority of the at least $10^4$ genes are targeted with no more than 25 structurally distinct sgRNAs and wherein the structurally distinct sgRNAs of the library comprise binding regions:
        (i) beginning at the 5' end with a guanosine nucleotide;
        (ii) having a length of between 19 and 21 nucleotides;
        (iii) lacking a UUU sequence; and
        (iv) targeting a genomic site in which the PAM site having the sequence NGG is not followed by a G.

2. The method of claim 1, wherein the library of sgRNAs contains at least 50,000 structurally distinct sgRNAs.

3. The method of claim 1, wherein the selecting the test cells on the basis of the phenotype comprises selecting the test cells on the basis of protein expression, RNA expression, or protein activity, or wherein the selecting the test cells on the basis of the phenotype comprises fluorescence activated cell sorting, affinity purification of cells, selection based on cell motility or culturing the cells, thereby selecting the test cells on the basis of cellular proliferation.

4. The method of claim 1, wherein the sgRNA is encoded by an expression cassette in the test cell, the expression cassette comprising a promoter operably linked to a polynucleotide encoding the sgRNA.

5. A method of identifying a lead compound for treatment of a phenotype, the method comprising:
    performing a method according to claim 1, thereby identifying a gene that modulates the phenotype; and
    identifying or screening for a lead compound that modulates
    expression of the gene or activity of a peptide encoded by the gene.

6. A method of identifying interacting genes, the method comprising:
    (i) performing a method according to claim 1, thereby identifying a plurality of structurally distinct sgRNAs that target genes that modulate the phenotype;
    (ii) contacting a plurality of test cells with a library comprising a plurality of pairwise combinations of the structurally distinct sgRNAs identified in (i);
    (iii) selecting the test cells based on the phenotype; and
    (iv) quantitating frequency of the pairwise combinations of structurally distinct sgRNAs within the population of selected cells, wherein the pairwise combinations of structurally distinct sgRNAs that are overrepresented or underrepresented in the selected cells are predicted to target interacting genes.

7. The method of claim 6, wherein the pair wise combinations of structurally distinct sgRNAs comprise a first member and a second member of the pair, and wherein the first member and second member target unlinked genes.

8. The method of claim 6, wherein the pairwise combinations of structurally distinct sgRNAs that are overrepresented or underrepresented in the selected cells are overrepresented or underrepresented relative to the frequency of first and second members of each pairwise combination in (ii).

9. A method of optimizing an sgRNA, the method comprising:
performing a method according to claim 1,
wherein the plurality of structurally distinct sgRNAs target different regions within or next to a single gene,
wherein the most overrepresented or underrepresented sgRNAs in the selected test cells are identified as optimized sgRNAs that target the gene.

10. The method of claim 1, wherein a majority of the library of structurally distinct sgRNAs comprise binding regions having at least one of the following:
(i) a binding region that targets a gene that is at least 1 bp apart from a gene targeted by another sgRNA of the library;
(ii) a GC percentage of between about 40% and about 60%; and
(iii) a methylated or fluorescent nucleotide.

11. The method of claim 1, wherein a majority of the library of structurally distinct sgRNAs do not contain a nucleotide sequence of three or more repeated nucleotides, excluding a 3' transcription termination sequence of the structurally distinct sgRNAs.

12. The method of claim 1, wherein a majority of the library of structurally distinct sgRNAs lack a binding region having three or more nucleotide mismatches between the binding region and the targeted gene.

13. The method of claim 1, wherein a majority of the library of structurally distinct sgRNAs are targeted to non-overlapping genes.

14. The method of claim 1, wherein a majority of the targeted genes are targeted with 10 or fewer structurally distinct sgRNAs.

15. The method of claim 1, wherein a majority of the library of structurally distinct sgRNAs are targeted to a region of between 0 and 350 base pairs downstream of a transcription start site of the targeted genes; and wherein the transcriptional modulator is a transcriptional repressor.

16. The method of claim 15, wherein a majority of the library of structurally distinct sgRNAs are targeted to a region of between 25 and 100 base pairs downstream of the transcription start site of the targeted genes.

17. The method of claim 1, wherein the library of sgRNAs contains fewer than $5 \times 10^4$ structurally distinct sgRNAs and wherein the at least $10^4$ genes are targeted with less than 25 sgRNAs per targeted gene.

* * * * *